(12) United States Patent
Gifford et al.

(10) Patent No.: US 12,290,554 B2
(45) Date of Patent: *May 6, 2025

(54) COMPOSITIONS FOR OPTIMIZED BCR-ABL PEPTIDE VACCINES

(71) Applicant: Think Therapeutics, Inc., Newton, MA (US)

(72) Inventors: David Kenneth Gifford, Newton, MA (US); Brandon Carter, Cambridge, MA (US)

(73) Assignee: Think Therapeutics, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,067

(22) Filed: Sep. 21, 2022

(65) Prior Publication Data

US 2023/0099121 A1  Mar. 30, 2023

Related U.S. Application Data

(60) Provisional application No. 63/249,235, filed on Sep. 28, 2021.

(51) Int. Cl.
*A61K 38/00* (2006.01)
*A61K 39/00* (2006.01)
*C12N 15/85* (2006.01)

(52) U.S. Cl.
CPC ...... *A61K 39/001197* (2018.08); *A61K 39/00* (2013.01); *C12N 15/85* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,443,956 A | 8/1995 | Carney | |
| 5,961,978 A | 10/1999 | Gaudernack et al. | |
| 6,602,510 B1 | 8/2003 | Fikes et al. | |
| 7,488,718 B2 | 2/2009 | Scheinberg et al. | |
| 7,756,644 B2 | 7/2010 | Fridman et al. | |
| 7,973,128 B2 | 7/2011 | Kosmatopoulos et al. | |
| 8,007,810 B2 | 8/2011 | Fikes et al. | |
| 8,465,747 B2 | 6/2013 | Kosmatopoulos et al. | |
| 8,653,237 B2 | 2/2014 | Liu et al. | |
| 8,741,576 B2 | 6/2014 | Tangri et al. | |
| 8,765,687 B2 | 7/2014 | Scheinberg et al. | |
| 8,900,600 B2 | 12/2014 | Kosmatopoulos et al. | |
| 9,340,577 B2 | 5/2016 | Grey et al. | |
| 9,913,884 B2 | 3/2018 | Fikes et al. | |
| 10,024,868 B2 | 7/2018 | Kosmatopoulos et al. | |
| 10,238,741 B2 | 3/2019 | Creusot | |
| 10,335,473 B2 | 7/2019 | Eriksen | |
| 10,456,457 B2 | 10/2019 | Eriksen | |
| 10,556,943 B2 | 2/2020 | Knutson et al. | |
| 10,596,239 B2 | 3/2020 | Eriksen | |
| 10,738,355 B2 | 8/2020 | Sahin et al. | |
| 10,835,585 B2 | 11/2020 | Fritsch et al. | |
| 11,058,751 B1 | 7/2021 | Gifford et al. | |
| 11,161,892 B1 | 11/2021 | Gifford et al. | |
| 11,222,711 B2 | 1/2022 | Sahin et al. | |
| 11,235,039 B1 | 2/2022 | Gifford et al. | |
| 11,464,842 B1 | 10/2022 | Gifford et al. | |
| 11,466,053 B2 | 10/2022 | Tang et al. | |
| 11,672,850 B2 | 6/2023 | Gifford et al. | |
| 2002/0155093 A1 | 10/2002 | Houghton et al. | |
| 2002/0164346 A1 | 11/2002 | Nicolette | |
| 2003/0220239 A1 | 11/2003 | Simard et al. | |
| 2003/0224036 A1 | 12/2003 | Fikes et al. | |
| 2004/0037843 A1 | 2/2004 | Fikes et al. | |
| 2004/0072240 A1 | 4/2004 | Kosmatopoulos et al. | |
| 2006/0018915 A1 | 1/2006 | Ishioka et al. | |
| 2006/0093617 A1 | 5/2006 | Buyse et al. | |
| 2007/0054262 A1 | 3/2007 | Baker et al. | |

(Continued)

FOREIGN PATENT DOCUMENTS

WO WO-97/33602 A1 9/1997
WO WO-99/63945 A2 12/1999

(Continued)

OTHER PUBLICATIONS

Betts et al., "Amino Acid Properties and Consequences of Substitutions," Chapter 14 in Bioinformatics for Geneticists, Wiley & Sons, Ltd., Apr. 18, 2003, pp. 289-316.
Carter et al., "A pan-variant mRNA-LNP T cell vaccine protects HLA transgenic mice from mortality after infection with SARS-CoV-2 Beta," bioRxiv preprint, posted Sep. 26, 2022. 38 pages. (https://www.biorxiv.org/content/10.1101/2022.09.23.509206v1).
Carter et al., "A pan-variant mRNA-LNP T cell vaccine protects HLA transgenic mice from mortality after infection with SARS-CoV-2 Beta," Frontiers in Immunology, Mar. 9, 2023, vol. 14:1135815, pp. 1-9.

(Continued)

*Primary Examiner* — Aradhana Sasan
*Assistant Examiner* — Mercy H Sabila
(74) *Attorney, Agent, or Firm* — Wilmer Cutler Pickering Hale and Dorr LLP

(57) ABSTRACT

The present disclosure provides for methods, systems, and compositions of nucleic acid and peptide sequences. The present disclosure provides for a nucleic acid sequence encoding two or more amino acid sequences selected from the group consisting of SEQ ID NOs: 1 to 44. The present disclosure also provides for an immunogenic peptide composition comprising two or more peptides selected from the group consisting of SEQ ID NOs: 1 to 44. The present disclosure further provides for a nucleic acid sequence encoding one or more amino acid sequences selected from the group consisting of SEQ ID NOs: 46 to 112. The present disclosure additionally provides for an immunogenic peptide composition comprising one or more peptides selected from the group consisting of SEQ ID NOs: 46 to 112.

16 Claims, 10 Drawing Sheets

Specification includes a Sequence Listing.

(56) References Cited

U.S. PATENT DOCUMENTS

| | | | |
|---|---|---|---|
| 2007/0098776 | A1 | 5/2007 | Fikes et al. |
| 2007/0224201 | A1 | 9/2007 | Wu et al. |
| 2011/0002963 | A1 | 1/2011 | Weinschenk et al. |
| 2011/0182926 | A1 | 7/2011 | La Monica et al. |
| 2011/0257890 | A1 | 10/2011 | Weinschenk et al. |
| 2014/0178421 | A1 | 6/2014 | Kosmatopoulos |
| 2016/0101170 | A1 | 4/2016 | Hacohen et al. |
| 2016/0125129 | A1 | 5/2016 | Sahin et al. |
| 2018/0066017 | A1 | 3/2018 | Hunt et al. |
| 2018/0102585 | A1 | 4/2018 | Forster |
| 2018/0117133 | A1 | 5/2018 | Chaplin et al. |
| 2018/0134804 | A1 | 5/2018 | Scheinberg et al. |
| 2018/0141998 | A1 | 5/2018 | Nguyen et al. |
| 2019/0175727 | A1 | 6/2019 | Huang et al. |
| 2019/0307868 | A1 | 10/2019 | Rooney |
| 2019/0322714 | A1 | 10/2019 | Petit et al. |
| 2020/0061166 | A1 | 2/2020 | Sahin et al. |
| 2020/0069782 | A1 | 3/2020 | Biskup et al. |
| 2020/0078454 | A1 | 3/2020 | Kosmatopoulos et al. |
| 2020/0105378 | A1 | 4/2020 | Abelin et al. |
| 2020/0237885 | A1 | 7/2020 | Levey et al. |
| 2021/0154280 | A1 | 5/2021 | Martin et al. |
| 2021/0177954 | A1 | 6/2021 | Juneja |
| 2021/0177955 | A1 | 6/2021 | Petit et al. |
| 2021/0196806 | A1 | 7/2021 | Yelensky et al. |
| 2021/0196809 | A1 | 7/2021 | Maianti et al. |
| 2021/0268086 | A1 | 9/2021 | Zhong et al. |
| 2021/0268091 | A1 | 9/2021 | Juneja |
| 2021/0275657 | A1 | 9/2021 | Juneja et al. |
| 2021/0290746 | A1 | 9/2021 | Sahin et al. |
| 2021/0389280 | A1 | 12/2021 | Wang |
| 2022/0160848 | A1 | 5/2022 | Gifford et al. |
| 2022/0194999 | A1 | 6/2022 | Krishna et al. |

FOREIGN PATENT DOCUMENTS

| | | |
|---|---|---|
| WO | WO-2005/042698 A2 | 5/2005 |
| WO | WO-2009/002418 A2 | 12/2008 |
| WO | WO-2013/177214 A2 | 11/2013 |
| WO | WO-2016/172722 A1 | 10/2016 |
| WO | WO-2016/187508 | 11/2016 |
| WO | WO-2017/075531 A1 | 5/2017 |
| WO | WO-2018/081459 A1 | 5/2018 |
| WO | WO-2018/081480 A1 | 5/2018 |
| WO | WO-2018/102585 A1 | 6/2018 |
| WO | WO-2018/187356 A2 | 10/2018 |
| WO | WO-2019/246286 | 12/2019 |
| WO | WO-2020/037239 A1 | 2/2020 |
| WO | WO-2020/123300 A2 | 6/2020 |
| WO | WO-2020/154617 A1 | 7/2020 |
| WO | WO-2020/252039 A1 | 12/2020 |
| WO | WO-2020/253643 A1 | 12/2020 |
| WO | WO-2021/055594 | 3/2021 |
| WO | WO-2021/087840 A1 | 5/2021 |
| WO | WO-2021/207152 A1 | 10/2021 |
| WO | WO-2022/036142 A2 | 2/2022 |
| WO | WO-2022/132596 A2 | 6/2022 |
| WO | WO-2022/171032 A1 | 8/2022 |
| WO | WO-2022/180219 A1 | 9/2022 |
| WO | WO-2023/170535 A2 | 9/2023 |
| WO | WO-2023/230014 A1 | 11/2023 |

OTHER PUBLICATIONS

Chu et al., "A transformer-based model to predict peptide-HLA class I binding and optimize mutated peptides for vaccine design," Nature Machine Intelligence, vol. 4(3), Mar. 23, 2022, pp. 300-311 and figures. 15 pages.

Chu et al., "TransMut: a program to predict HLA-I peptide binding and optimize mutated peptides for vaccine design by the Transformer-derived self-attention model," Research Square, Sep. 30, 2021. 47 pages. (https://doi.org/10.21203/rs.3.rs-785618/v1).

Getentry Accession No. CU234118, DNA Data Bank of Japan. (Year 2015). 1,543 pages.

NCBI Database, GenBank Accession No. AB051004. (Year 2016). 1 page.

NCBI Database, GenBank Accession No. FRAP01000011. (Year 2016). 73 pages.

NCBI Database, GenBank Accession No. PYDT01000009. (Year 2019). 983 pages.

Racle et al., "Robust prediction of HLA class II epitopes by deep motif deconvolution of immunopeptidomes," Nature Biotechnology, Nov. 2019, vol. 37(11), pp. 1283-1286, Methods and Reporting Summary. 12 pages.

UniProt Accession No. A0A1M6V319-A0A1M6V319_PSETH. (Year 2017). 5 pages.

UniProt Accession No. A0A4S8INI8-A0A4S8INI8_MUSBA. (Year 2019). 6 pages.

UniProt Accession No. A4YTR3-A4YTR3_BRASO. (Year 2007). 5 pages.

Aurisicchio et al., "A novel minigene scaffold for therapeutic cancer vaccines," OncoImmunology, published online Jan. 16, 2014, vol. 3, e27529, pp. 1-13. 14 pages.

Fikes et al., "Design of multi-epitope, analogue-based cancer vaccines," Expert Opinion on Biological Therapy, published online Mar. 3, 2005, vol. 3:6, pp. 985-993. 10 pages.

Fridman et al., "An efficient T-cell epitope discovery strategy using in silico prediction and the iTopia assay platform," OncoImmunology, published online Nov. 30, 2012, vol. 1:8, pp. 1258-1270 and Supplemental Material. 21 pages.

Zhang et al., "Epitope-based minigene vaccine targeting fibroblast activation protein α induces specific immune responses and anti-tumor effects in 4 T1 murine breast cancer model," International Immunopharmacology, available online Sep. 21, 2022, vol. 112, 109237, pp. 1-10.

Antunes et al., "General Prediction of Peptide-MHC Binding Modes Using Incremental Docking: A Proof of Concept," Scientific Reports, published online Mar. 12, 2018, vol. 8(1):4327-4339. 13 pages.

Badrinath et al., "A vaccine targeting resistant tumours by dual T cell plus NK cell attack," Nature, Jun. 30, 2022, vol. 606, pp. 992-998 and Methods. 31 pages.

Bai et al., "Immune-based mutation classification enables neoantigen prioritization and immune feature discovery in cancer immunotherapy," Oncoimmunology, Jan. 15, 2021, vol. 10(1), e1868130. 13 pages.

Bear et al., "Biochemical and functional characterization of mutant KRAS epitopes validates this oncoprotein for immunological targeting," Nature Communications, published online Jul. 16, 2021, vol. 12(1):4365-4380. 16 pages.

Brito et al., "A cationic nanoemulsion for the delivery of next-generation RNA vaccines," Molecular Therapy, Dec. 2014, vol. 22(12), pp. 2118-2129.

Bulik-Sullivan et al., "Deep learning using tumor HLA peptide mass spectrometry datasets improves neoantigen identification," Nature Biotechnology (2019), published online Dec. 17, 2018, vol. 37, pp. 55-63 and Online Methods. 13 pages.

Dai et al., "Constrained Submodular Optimization for Vaccine Design," arXiv preprint, arXiv:2206.08336v2. https://arxiv.org/abs/2206.08336, version 2, Jan. 27, 2023. 24 pages.

Geall et al., "Nonviral delivery of self-amplifying RNA vaccines," Proc. Natl. Acad. Sci., Sep. 4, 2012, vol. 109(36), pp. 14604-14609.

Hie et al., "Learning the language of viral evolution and escape," Science, Jan. 15, 2021, vol. 371(6526):284-288. 5 pages.

Kreiner et al., "Current state of antigen-specific immunotherapy for type 1 diabetes," Curr. Opin. Endocrinol. Diabetes Obes., Aug. 2021, vol. 28(4), pp. 411-418.

Li et al., "Circular RNA cancer vaccines drive immunity in hard-to-treat malignancies," Theranostics, Aug. 29, 2022, vol. 12(14), pp. 6422-6436.

London et al., "Rosetta FlexPepDock web server—high resolution modeling of peptide-protein interactions," Nucleic Acids Research, published online May 27, 2011, vol. 39, Web Server issue: W249-253.

Parkhurst et al., "Improved induction of melanoma-reactive CTL with peptides from the melanoma antigen gp100 modified at HLA-

(56) References Cited

OTHER PUBLICATIONS

A*0201-binding residues," The Journal of Immunology, Sep. 15, 1996, vol. 157(6), pp. 2539-2548.
Postigo-Fernandez et al., "A multi-epitope DNA vaccine enables a broad engagement of diabetogenic T cells for tolerance in Type 1 diabetes," Journal of Autoimmunity (2019), available online Nov. 17, 2018, vol. 98, pp. 13-23.
Robinson et al., "Potential for Antigen-Specific Tolerizing Immunotherapy in Systematic Lupus Erythematosus," Frontiers in Immunology, Jul. 16, 2021, vol. 12:654701, pp. 1-13.
Slingluff et al., "Immunologic and clinical outcomes of a randomized phase II trial of two multipeptide vaccines for melanoma in the adjuvant setting," Clin. Cancer Res., Nov. 2007, vol. 13(21), pp. 6386-6395.
Wang et al., "A benchmark study of sequence alignment methods for protein clustering," BMC Bioinformatics, Dec. 31, 2018, vol. 19(Suppl 19):529, pp. 95-104.
Wang et al., "Direct Detection and Quantification of Neoantigens," Cancer Immunology Research, published online Sep. 16, 2019, vol. 7(11), pp. 1748-1754.
U.S. Appl. No. 17/243,096, Gifford et al.
U.S. Appl. No. 17/551,679, Gifford et al.
U.S. Appl. No. 17/815,086, Gifford et al.
Abelin et al., "Defining HLA-II Ligand Processing and Binding Rules with Mass Spectrometry Enhances Cancer Epitope Prediction," Immunity, Oct. 15, 2019, vol. 51(4), pp. 766-779; e1-e17, and Update (Feb. 9, 2021, 54(2):388). 34 pages.
Alhadj-Ali et al., "Metabolic and immune effects of immunotherapy with proinsulin peptide in human new-onset type 1 diabetes," Science Translation Medicine, Aug. 9, 2017, vol. 9;9(402):eaaf7779. 9 pages.
Alvarez, B. et al., "NNAlign_MA; MHC Peptidome Deconvolution for Accurate MHC Binding Motif Characterization and Improved T-cell Epitope Predictions", Molecular & Cellular Proteomics, Dec. 2019, vol. 18(12), pp. cover, 2459-2477 (20 pages).
Asahara et al., "Phase I/II clinical trial using HLA-A24-restricted peptide vaccine derived from KIF20A for patients with advanced pancreatic cancer," Journal of Translational Medicine, Nov. 16, 2013, vol. 11:291. 13 pages.
Bae et al., "Myeloma-Specific Multiple Peptides Able to Generate Cytotoxic T Lymphocytes: A Potential Therapeutic Application in Muliple Myeloma and other Plasma Cell Disorders," Clinical Cancer Research, published online Jul. 2, 2012, vol. 18(17), pp. 4850-4860.
Berzofsky et al., "Progress on new vaccine strategies for the immunotherapy and prevention of cancer," The Journal of Clinical Investigation, Jun. 2004, vol. 113(11), pp. 1515-1525.
Berzofsky et al., "Strategies for designing and optimizing new generation vaccines," Nature Reviews: Immunology, vol. 1(3), Dec. 2001, pp. 209-219.
Berzofsky, "Epitope selection and design of synthetic vaccines. Molecular approaches to enhancing immunogenicity and cross-reactivity of engineered vaccines," Annals of the New York Academy of Sciences, Aug. 12, 1993, vol. 690(1), pp. 256-264.
Bhasin, M. and Raghava, G.P.S., "Prediction of Promiscuous and High-Affinity Mutated MHC Binders", Hybridoma and Hybridomics, Nov. 4, 2003, vol. 22, 229-234, (8 pages).
Candia et al., "On Peptides and Altered Peptide Ligands: From Origin, Mode of Action and Design to Clinical Application (Immunotherapy)," International Archives of Allergy and Immunology, published online Sep. 20, 2016; vol. 170(4), pp. 211-233.
Chicz et al., "Predominant naturally processed peptides bound to HLA-DR1 are derived from MHC-related molecules and are heterogeneous in size," Nature, Aug. 27, 1992, vol. 358(6389), pp. 764-768.
Cleveland et al., "Routine large-scale production of monoclonal antibodies in a protein-free culture medium," Journal of Immunological Methods, Jan. 28, 1983, vol. 56, Issue 2, pp. 221-234.

Croft et al., "Most viral peptides displayed by class I MHC on infected cells are immunogenic," Proceedings of the National Academy of Sciences, Feb. 19, 2019, vol. 116(8), pp. 3112-3117.
Dai et al., "Machine learning optimization of peptides for presentation by class II MHCs," bioRxiv, posted Aug. 18, 2020 (https://doi.org/10.1101/2020.08.18.256081). 35 pages.
Dastagir et al., "Efficient Presentation of Multiple Endogenous Epitopes to Both CD4+ and CD8+ Diabetogenic T Cells for Tolerance," Molecular Therapy: Methods & Clinical Development, Mar. 2017, vol. 4, pp. 27-38.
Dey et al., "A Bioinformatics approach to designing a Zika virus vaccine," Computational Biology and Chemistry, available online Mar. 10, 2017, vol. 68, pp. 143-152.
Dyall et al., "Heteroclitic Immunization Induces Tumor Immunity," J. Exp. Med., Nov. 2, 1998, vol. 188(9), pp. 1553-1561.
Fong et al., "Altered peptide ligand vaccination with Flt3 ligand expanded dendritic cells for tumor immunotherapy," PNAS, Jul. 17, 2001, vol. 98(15), pp. 8809-8814.
Gibson et al., "Proinsulin multi-peptide immunotherapy induces antigen-specific regulatory T cells and limits autoimmunity in a humanized model," Clinical and Experimental Immunology, Dec. 2015, vol. 182(3), pp. 251-260.
Guevara-Patino et al., "Optimization of a self antigen for presentation of multiple epitopes in cancer immunity," The Journal of Clinical Investigation, May 2006, vol. 116(5), pages: cover, 1382-1390.
Hollingsworth et al., "Turning the corner on therapeutic cancer vaccines," npj Vaccines, published online Feb. 8, 2019, vol. 4(7), pp. 1-10.
Hong et al., "Epitope-optimized alpha-fetoprotein genetic vaccines prevent carcinogen-induced murine autochthonous hepatocellular carcinoma," Hepatology, Apr. 2014, vol. 59(4), pp. 1448-1458.
Hoppes et al., "Altered Peptide Ligands Revisited: Vaccine Design through Chemically Modified HLA-A2-Restricted T Cell Epitopes," Journal of Immunology, published online Oct. 13, 2014, vol. 193, pp. 4803-4813. (12 pages).
Houghton et al., "Immunological validation of the EpitOptimizer program for streamlined design of heteroclitic epitopes," Vaccine, available online Jun. 4, 2007, vol. 25(29), pp. 5330-5342.
International Search Report and Written Opinion mailed Mar. 28, 2022, in the International Application No. PCT/US2021/060013. 14 pages.
International Search Report and Written Opinion mailed Oct. 14, 2022, in the International Application No. PCT/US22/26354. 21 pages.
Jain et al., "Synthetic Tumor-Specific Breakpoint Peptide Vaccine in Patients With Chronic Myeloid Leukemia and Minimal Residual Disease," Cancer, Sep. 1, 2009, vol. 115, pp. 3924-3934.
Jaravine et al., "Assessment of cancer and virus antigens for cross-reactivity in human tissues," Bioinformatics, Jan. 1, 2017, vol. 33, No. 1, pp. 104-111.
Jaravine et al., "Expitope 2.0: a tool to assess immunotherapeutic antigens for their potential cross-reactivity against naturally expressed proteins in human tissues," BMC Cancer, Dec. 28, 2017, vol. 17:892. 9 pages.
Jurtz, V. et al., "NetMHCpan-4.0: Improved Peptide-MHC Class I Interaction Predictions Integrating Eluted Ligand and Peptide Binding Affinity Data", The Journal of Immunology, prepublished online Oct. 4, 2017, vol. 199, pp. 3360-3368 (9 pages).
Keogh et al., "Identification of new epitopes from four different tumor-associated antigens: Recognition of naturally processed epitopes correlates with HLA-A*0201-binding affinity," The Journal of Immunology, Jul. 15, 2001, vol. 167(2), pp. 787-796. 11 pages.
Klinger et al., "Multiplex identification of antigen-specific T cell receptors using a combination of immune assays and immune receptor sequencing," PLOS One, Oct. 28, 2015, vol. 10(10), e0141561. 21 pages.
Kranz et al., "Systemic RNA delivery to dendritic cells exploits antiviral defence for cancer immunotherapy," Nature, Jun. 16, 2016, vol. 534(7607), pp. 396-401, and Methods. 16 pages.

(56) References Cited

OTHER PUBLICATIONS

Kreiter, et al., "Increased antigen presentation efficiency by coupling antigens to MHC class I trafficking signals," The Journal of Immunology, Jan. 2008, vol. 180(1), pp. 309-318, and Corrections. 12 pages.

Krienke, C. et al., "A noninflammatory mRNA vaccine for treatment of experimental autoimmune encephalomyelitis", Science, Jan. 8, 2021, vol. 371, pp. 145-153 (10 pages).

Liu et al. "Computationally Optimized SARS-CoV-2 MHC Class I and II Vaccine Formulations Predicted to Target Human Haplotype Distributions," Cell Systems, Aug. 26, 2020, vol. 11(2), pp. 131-144, e1-e6, Supplementary Table. 23 pages.

Liu et al., "Maximum n-times Coverage for COVID-19 Vaccine Design," arXiv (arXiv:2101.10902v1), submitted Jan. 24, 2021. 13 pages.

Liu et al., "Predicted Cellular Immunity Population Coverage Gaps for SARS-CoV-2 Subunit Vaccines and their Augmentation by Compact Peptide Sets," bioRxiv, posted Oct. 21, 2020, 29 pages. (https://www.biorxiv.org/content/10.1101/2020.08.04.200691v2).

Liu et al., "Predicted Cellular Immunity Population Coverage Gaps for SARS-CoV-2 Subunit Vaccines and their Augmentation by Compact Peptide Sets," Cell Systems, Journal Pre-proof, Nov. 26, 2020. (https://doi.org/10.1016/j.cels.2020.11.010). 36 pages.

Longmate et al., "Population coverage by HLA class-I restricted cytotoxic T-lymphocyte epitopes," Immunogenetics (2001), published online Dec. 19, 2000, vol. 52, pp. 165-173.

Maa et al., "Biopharmaceutical Powders: Particle Formation and Formulation Considerations," Current Pharmaceutical Biotechnology, Nov. 2000, vol. 1, No. 3, pp. 283-302.

Mahanty et al., "Immunogenicity of infectious pathogens and vaccine antigens," BMC Immunology, published online May 29, 2015, vol. 16(31), pp. 1-6.

Mashiba et al., "Identification of CTL epitopes in hepatitis C virus by a genome-wide computational scanning and a rational design of peptide vaccine," Immunogenetics, published online Jan. 16, 2007, vol. 59, pp. 197-209.

Merriam-Webster, "Prevent", available online at https://www.merriam-webster.com/dictionary/prevent. 10 pages. Accessed on Sep. 24, 2021.

Mösch et al., "Machine Learning for Cancer Immunotherapies Based on Epitope Recognition by T Cell Receptors," Frontiers in Genetics, Nov. 19, 2019, vol. 10, Article 1141. 17 pages.

Nair et al., "A simple practice guide for dose conversion between animals and human," Journal of Basic and Clinical Pharmacy, Article Review, Mar.-May 2016, vol. 7, Issue 2, pp. 27-31.

Ng et al., "In silico-guided sequence modifications of K-ras epitopes improve immunological outcome against G12V and G13D mutant KRAS antigens," PeerJ, published Jul. 20, 2018, 6:e5056. doi: 10.7717/peerj.5056. 21 pages.

Nielsen et al., "NNAlign: a platform to construct and evaluate artificial neural network models of receptor-ligand interactions," Nucleic Acids Research, published online Apr. 12, 2017, vol. 45, pp. W344-W349.

Nielsen et al., "The role of the proteasome in generating cytotoxic T-cell epitopes: insights obtained from improved predictions of proteasomal cleavage," Immunogenetics, published online Mar. 3, 2005, vol. 57, pp. 33-41.

Nielsen, M. and Lund, O., "NN-align. An artificial neural network-based alignment algorithm for MHC class II peptide binding prediction", BMC Bioinformatics, Sep. 18, 2009, vol. 10:296, pp. 1-10 (10 pages).

Nielsen, M. et al., "Quantitative Predictions of Peptide Binding to Any HLA-DR Molecule of Known Sequence: NetMHCIIpan", PLoS Computational Biology, Jul. 4, 2008, vol. 4(7):e1000107, pp. 1-10 (10 pages).

O'Donnell, T.J. et al., "MHCflurry 2.0: Improved Pan-Allele Prediction of MHC Class I-Presented Peptides by Incorporating Antigen Processing", Cell Systems, Jul. 22, 2020, vol. 11, pp. cover, 42-48 (15 pages).

O'Donnell, T.J. et al., "MHCflurry: Open-Source Class I MHC Binding Affinity Prediction", Cell Systems, Jul. 25, 2018, vol. 7, pp. cover, 129-132 (9 pages).

Ogishi et al., "Quantitative Prediction of the Landscape of T Cell Epitope Immunogenicity in Sequence Space," Frontiers in Immunology, Apr. 16, 2019, vol. 10, Article 827. 20 pages.

Park et al., "Accurate structure prediction of peptide-MHC complexes for identifying highly immunogenic antigens," Mol. Immunol., Nov. 2013, vol. 56(0):81-90. NIH Author Manuscript. 25 pages.

Reynisson et al., "NetMHCpan-4.1 and NetMHCIIpan-4.0: improved predictions of MHC antigen presentation by concurrent motif deconvolution and integration of MS MHC eluted ligand data," Nucleic Acids Research, published online May 14, 2020; vol. 48(W1), pp. W449-W454.

Rist et al., "HLA peptide length preferences control CD8+ T cell responses," The Journal of Immunology, published online Jun. 7, 2013, vol. 191(2), pp. 561-571. 12 pages.

Rosenberg et al., "Immunologic and therapeutic evaluation of a synthetic peptide vaccine for the treatment of patients with metastatic melanoma," Nature Medicine, Mar. 1998, vol. 4(3), pp. 321-327.

Sahin et al., "Personalized RNA mutanome vaccines mobilize poly-specific therapeutic immunity against cancer," Nature, Jul. 13, 2017, vol. 547(7662), pp. 222-226, and Methods. 19 pages.

Schipper et al., "Minimal Phenotype Panels, A Method for Achieving Maximum Population Coverage with a Minimum of HLA Antigens," Human Immunology, vol. 51, Dec. 1996, pp. 95-98.

Sette et al., "Peptides and Methods for Creating Synthetic Peptides With Modulated Binding Affinity for HLA Molecules," Application for utility U.S. Appl. No. 09/226,775, filed Jan. 6, 1999—not published, abandoned. 133 pages.

Sette et al., "The Relationship Between Class I Binding Affinity and Immunogenicity of Potential Cytotoxic T Cell Epitopes," The Journal of Immunology, Dec. 15, 1994, vol. 153, pp. 5586-5592.

Shimokawa, C et al., "CD8+ regulatory T cells are critical in prevention of autoimmune-mediated diabetes", Nature Communications, Apr. 22, 2020, vol. 11:1922, pp. 1-9 (9 pages).

Sim et al., "Correction—High-affinity oligoclonal TCRs define effective adoptive T cell therapy targeting mutant KRAS-G12D," Proc. Natl. Acad. Sci. USA, Nov. 3, 2020, vol. 117(44), pp. 27743-27744.

Sim et al., "High-affinity oligoclonal TCRs define effective adoptive T cell therapy targeting mutant KRAS-G12D," Proc. Natl. Acad. Sci. USA, first published May 27, 2020, vol. 117(23), pp. 12826-12835.

Slansky et al., "Enhanced antigen-specific antitumor immunity with altered peptide ligands that stabilize the MHC-peptide-TCR complex," Immunity, Oct. 2000, vol. 13(4), pp. 529-538.

Slota et al., "ELISpot for measuring human immune responses to vaccines," Expert Review of Vaccines, Mar. 2011, vol. 10(3), pp. 299-306. NIH Author Manuscript. 14 pages.

Soria-Guerra et al., "An overview of bioinformatics tools for epitope prediction: implications on vaccine development," Journal of Biomedical Informatics (2015), available online Nov. 10, 2014, vol. 53, pp. 405-414.

Takahashi et al., "Induction of Broadly Cross-Reactive Cytotoxic T Cells Recognizing an HIV-1 Envelope Determinant," Science, Jan. 17, 1992, vol. 255(5042), pp. 333-336.

Tangri et al., "Structural Features of Peptide Analogs of Human Histocompatibility Leukocyte Antigen Class I Epitopes That Are More Potent and Immunogenic than Wild-Type Peptide," Journal of Experimental Medicine, Sep. 17, 2001, vol. 194(6), pp. 833-846.

Tapia-Calle et al., "A PBMC-Based System to Assess Human T Cell Responses to Influenza Vaccine Candidates In Vitro," Vaccines, Nov. 13, 2019, vol. 7(4):181. 26 pages.

Toussaint, N.C et al., "A Mathematical Framework for the Selection of an Optimal Set of Peptides for Epitope-Based Vaccines", PLoS Computational Biology, Dec. 26, 2008, vol. 4(12):e1000246, pp. 1-10 (10 pages).

Trolle et al., "The length distribution of class I-restricted T cell epitopes is determined by both peptide supply and MHC allele-specific binding preference," The Journal of Immunology, Feb. 15, 2016, vol. 196(4), 1480-1487. HSS Author Manuscript. 21 pages.

(56) References Cited

OTHER PUBLICATIONS

Vita et al., "The Immune Epitope Database (IEDB): 2018 update," Nucleic Acids Research (2019), published online Oct. 24, 2018, vol. 47, database issue D339-D343. 5 pages.

Woodham et al., "Nanobody-Antigen Conjugates Elicit HPV-Specific Antitumor Immune Responses," Cancer Immunology Research, Jul. 2018, vol. 6(7); pp. 870-880.

Zaremba et al., "Identification of an enhancer agonist cytotoxic T lymphocyte peptide from human carcinoembryonic antigen," Cancer Research, Oct. 15, 1997, vol. 57(20), pp. 4570-4577.

Zhang et al., "Cancer vaccines: Targeting KRAS-driven cancers," Expert Review of Vaccines, published online Mar. 14, 2020, vol. 19(2), pp. 163-173. 12 pages.

Zirlik et al., "Cytotoxic T cells generated against heteroclitic peptides kill primary tumor cells independent of the binding affinity of the native tumor antigen peptide," Blood, Dec. 1, 2006, vol. 108, No. 12, pp. 3865-3870.

Bakker et al., "Analogues of CTL epitopes with improved MHC class-I binding capacity elicit anti-melanoma CTL recognizing the wild-type epitope," Int. J. Cancer, Jan. 27, 1997, vol. 70(3), pp. 302-309.

Gross et al., "High vaccination efficiency of low-affinity epitopes in antitumor immunotherapy," The Journal of Clinical Investigation, Feb. 2004, vol. 113(3), pp. 425-433.

International Search Report and Written Opinion mailed Apr. 2, 2024, in the International Application No. PCT/US23/74984. 11 pages.

Menez-Jamet et al., "Optimized tumor cryptic peptides: the basis for universal neo-antigen-like tumor vaccines," Ann. Transl. Med., Jul. 2016, 4(14):266, Review Article pp. 1-11.

Scardino et al., "HER-2/neu and hTERT cryptic epitopes as novel targets for broad spectrum tumor immunotherapy," The Journal of Immunology, Jun. 2002, 168(11):5900-6. 8 pages.

Tourdot et al., "A general strategy to enhance immunogenicity of low-affinity HLA-A2.1-associated peptides: implication in the identification of cryptic tumor epitopes," Eur. J. Immunol., Dec. 2000, vol. 30(12), pp. 3411-3421.

Valmori et al., "Enhanced generation of specific tumor-reactive CTL in vitro by selected Melan-A/MART-1 immunodominant peptide analogues," The Journal of Immunology, Feb. 15, 1998, 160(4):1750-8. 10 pages.

Bell et al., "Dynamics-Based Peptide—MHC Binding Optimization by a Convolutional Variational Autoencoder: A Use-Case Model for CASTELO," Journal of Chemical Theory and Computation, Nov. 18, 2021, vol. 17, pp. 7962-7971.

Xiao et al., "In silico design of MHC class I high binding affinity peptides through motifs activation map," BMC Bioinformatics, published Dec. 31, 2018, vol. 19(Suppl 19):516. 12 pages.

Factoring of disease presentation type probabilities and for each
presentation, probability of targets presented

| | Brain Cancer | Bronchus and Lung Cancer | Colorectal Cancer | Pancreatic Cancer | Skin Cancer | Thyroid Cancer | Breast Cancer | Ovarian Cancer |
|---|---|---|---|---|---|---|---|---|
| BRAF_V600E | - | - | 0.1029 | - | 0.4392 | 0.5854 | - | - |
| BRAF_V600M | - | - | - | - | 0.0853 | - | - | - |
| EGFR_A289V | 0.0230 | - | - | - | - | - | - | - |
| EGFR_G598V | 0.0208 | - | - | - | - | - | - | - |
| EGFR_L858R | - | 0.0216 | - | - | - | - | - | - |
| HRAS_Q61K | - | - | - | - | - | 0.0061 | - | - |
| HRAS_Q61R | - | - | - | - | - | 0.0285 | - | - |
| IDH1_R132C | 0.0197 | - | - | - | - | - | - | - |
| IDH1_R132H | 0.4178 | - | - | - | - | - | - | - |
| KRAS_G12A | - | 0.0169 | - | - | - | - | - | - |
| KRAS_G12C | - | 0.0583 | - | - | - | - | - | - |
| KRAS_G12D | - | 0.0188 | 0.1235 | 0.3280 | - | - | - | - |
| KRAS_G12R | - | - | - | 0.1505 | - | - | - | - |
| KRAS_G12V | - | 0.0376 | 0.0947 | 0.2258 | - | - | - | 0.0092 |
| KRAS_G13D | - | - | 0.0700 | - | - | - | - | - |
| NRAS_Q61K | - | - | - | - | 0.0832 | 0.0163 | - | - |
| NRAS_Q61L | - | - | - | - | 0.0384 | - | - | - |
| NRAS_Q61R | - | - | - | - | 0.1215 | 0.0630 | - | 0.0069 |
| PIK3CA_E542K | - | 0.0169 | - | - | - | - | 0.0435 | - |
| PIK3CA_E545K | - | 0.0197 | 0.0700 | - | - | - | 0.0638 | - |
| PIK3CA_H1047R | - | - | - | - | - | - | 0.1225 | - |
| TP53_R158L | - | 0.0188 | - | - | - | - | - | - |
| TP53_R175H | 0.0186 | - | 0.0679 | - | - | - | 0.0202 | 0.0343 |
| TP53_R248Q | - | - | - | - | - | - | - | 0.0252 |
| TP53_R273C | 0.0581 | - | - | - | - | - | 0.0051 | 0.0137 |
| TP53_R273H | - | - | - | - | - | - | 0.0121 | 0.0206 |

FIG. 8

```
def merge_multi(lists):
    values = []

# While any list in lists has elements remaining
    while max(map(lambda l: len(l), lists)) > 0:
        # Find list with largest value at its head.
        cur_max = None
        cur_max_idx = None
        for idx, l in enumerate(lists):
            if not l:  # List is empty.
                continue
            if cur_max is None or l[0] > cur_max:
                cur_max = l[0]
                cur_max_idx = idx
        # Pop that value from list l.
        values.append((lists[cur_max_idx].pop(0), cur_max_idx))

return values
```

FIG. 10

COMPOSITIONS FOR OPTIMIZED BCR-ABL PEPTIDE VACCINES

This application claims the benefit under 35 U.S.C. § 119(e) of provisional application U.S. Ser. No. 63/249,235, filed Sep. 28, 2021, the entire contents of which is incorporated by reference herein.

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entireties.

Sequence Listing

The instant application contains a Sequence Listing which has been submitted electronically in XML format and is hereby incorporated by reference in its entirety. The XML copy, created on Sep. 13, 2022, is named 2215269_00129US2_Sequence_Listing_as_filed.xml and is 55,022 kilobytes in size.

TECHNICAL FIELD

The present invention relates generally to compositions, systems, and methods of peptide vaccines. More particularly, the present invention relates to compositions, systems, and methods of designing peptide vaccines to treat or prevent disease optimized based on predicted population immunogenicity.

BACKGROUND

The goal of a peptide vaccine is to train the immune system to recognize and expand its capacity to engage cells that display target peptides to improve the immune response to cancerous cells or pathogens. A peptide vaccine can also be administered to someone who is already diseased to increase their immune response to a causal cancer, other diseases, or pathogen. Alternatively, a peptide vaccine can be administered to induce the immune system to have therapeutic tolerance to one or more peptides. There exists a need for compositions, systems, and methods of peptide vaccines based on prediction of the target peptides that will be displayed to protect a host from cancer, other disease, or pathogen infection. We introduce novel prophylactic and therapeutic vaccines for cancer based upon neoantigens introduced by the BCR-ABL gene fusion that occurs in cases of chronic myelogenous leukemia (CML), acute lymphoblastic leukemia (ALL), and acute myelogenous leukemia (AML), breast invasive ductal carcinoma, and other cancers.

SUMMARY OF THE INVENTION

In one aspect, described herein is a composition comprising nucleic acid sequences encoding at least two amino acid sequences selected from the group consisting of SEQ ID NOs: 1 to 8, SEQ ID NOs: 10 to 17, and SEQ ID NOs: 19 to 44.

In some embodiments, the nucleic acid sequences are contained in a construct for in vivo expression of the nucleic acid sequences.

In some embodiments, an administration of the nucleic acid sequences causes one or more peptides encoded by the nucleic acid sequences to be displayed by an HLA class I molecule in a subject.

In some embodiments, the nucleic acid sequences are contained in a construct for in vivo expression of at least two peptides encoded by the nucleic acid sequences, wherein an administration of the nucleic acid sequences causes: a first peptide of the at least two peptides to be displayed by a first plurality of HLA class I alleles in the subject; and a second peptide of the at least two peptides to be displayed by a second plurality of HLA class I alleles in the subject, wherein the first plurality of HLA class I alleles and the second plurality of HLA class I alleles differ by at least one HLA class I allele.

In some embodiments, the one or more peptides is a modified or an unmodified fragment of a BCL-ABL gene fusion. In some embodiments, the BCR-ABL gene fusion is b3a2 or b2a2. In some embodiments, the two or more amino acid sequences are selected based on a prevalence of the BCR-ABL gene fusion in a risk group that the subject belongs to, and wherein the composition is administered in an effective amount to the subject to promote an immune response against cancer or to treat cancer, and wherein the cancer is associated with the BCR-ABL gene fusion.

In some embodiments, the nucleic acid sequences are configured for administration in an effective amount to the subject to treat cancer.

In another aspect, described herein is a peptide composition comprising at least two peptides selected from the group consisting of SEQ ID NOs: 1 to 8, SEQ ID NOs: 10 to 17, and SEQ ID NOs: 19 to 44.

In some embodiments, a peptide in the peptide composition is configured for display by a HLA class I molecule in a subject.

In some embodiments, an administration of a first peptide of the at least two peptides causes: the first peptide to be displayed by a first plurality of HLA class I alleles in a subject; and a second peptide of the at least two peptides to be displayed by a second plurality of HLA class I alleles in a subject, wherein the first plurality of HLA class I alleles and the second plurality of HLA class I alleles differ by at least one HLA class I allele.

In some embodiments, a peptide in the peptide composition is a modified or an unmodified fragment of a BCL-ABL gene fusion. In some embodiments, the BCR-ABL gene fusion is b3a2 or b2a2. In some embodiments, the at least two peptides are selected based on a prevalence of the BCR-ABL gene fusion in a risk group that the subject belongs to, and wherein the peptide composition is administered in an effective amount to the subject to promote an immune response against cancer or to treat cancer, and wherein the cancer is associated with the BCR-ABL gene fusion.

In some embodiments, the peptide composition is configured for administration in an effective amount to a subject to treat cancer.

In another aspect, described herein are nucleic acid sequences encoding one or more amino acid sequences selected from the group consisting of SEQ ID NOs: 46 to 112.

In some embodiments, the nucleic acid sequence are contained in a construct for in vivo expression of the nucleic acid sequences.

In some embodiments, an administration of the nucleic acid sequences causes one or more peptides encoded by the nucleic acid sequences to be displayed by an HLA class II molecule in a subject.

In some embodiments, the one or more amino acid sequences are derived from a modified or an unmodified fragment of a BCL-ABL gene fusion. In some embodiments, the BCR-ABL gene fusion is b3a2 or b2a2. In some embodiments, the one or more amino acid sequences are selected based on a prevalence of the BCR-ABL gene fusion in a risk group that the subject belongs to, and wherein the composition is administered in an effective amount to the subject to promote an immune response against cancer or to treat cancer, and wherein the cancer is associated with the BCR-ABL gene fusion.

In some embodiments, the composition is configured for administration in an effective amount to a subject to treat cancer.

In some embodiments, the nucleic acid sequences encode at least two amino acid sequences selected from the group consisting of SEQ ID NOs: 46 to 112.

In another aspect, described herein is a peptide composition comprising one or more peptides selected from the group consisting of SEQ ID NOs: 46 to 112.

In some embodiments, a peptide in the peptide composition is configured for display by an HLA class II molecule in a subject.

In some embodiments, a peptide in the peptide composition is a modified or an unmodified fragment of a BCL-ABL gene fusion. In some embodiments, the BCR-ABL gene fusion is b3a2 or b2a2. In some embodiments, the one or more peptides are selected based on a prevalence of the BCR-ABL gene fusion in a risk group that the subject belongs to, and wherein the peptide composition is administered in an effective amount to the subject to promote an immune response against cancer or to treat cancer, and wherein the cancer is associated with the BCR-ABL gene fusion.

In some embodiments, the peptide composition is configured for administration in an effective amount to a subject to treat cancer.

In one aspect, described herein are nucleic acid sequences encoding one or more amino acid sequences selected from the group consisting of SEQ ID NOs: 1 to 45.

In some embodiments, the nucleic acid sequences encode two or more amino acid sequences selected from the group consisting of SEQ ID NOs: 1 to 45.

In some embodiments, the invention provides for an immunogenic composition comprising nucleic acid sequences encoding one or more amino acid sequences selected from the group consisting of SEQ ID NOs: 1 to 45.

In some embodiments, the immunogenic composition is administered to a subject. In some embodiments, the immunogenic composition comprises nucleic acid sequences encoding two or more amino acid sequences selected from the group consisting of SEQ ID NOs: 1 to 45. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or an unmodified fragment of a BCR-ABL gene fusion. In some embodiments, the BCR-ABL gene fusion is b3a2 or b2a2. In some embodiments, the immunogenic composition is administered in an effective amount to a subject to prevent cancer. In some embodiments, the immunogenic composition is administered in an effective amount to a subject to treat cancer. In some embodiments, the immunogenic composition is administered in an effective amount to a subject to prevent chronic myelogenous leukemia (CML), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CML), acute lymphoblastic leukemia (ALL), acute myelogenous leukemia (AML), or breast invasive ductal carcinoma.

In some embodiments, the immunogenic composition comprises nucleic acid sequences encoding at least three amino acid sequences selected from the group consisting of SEQ ID NOs: 1 to 45.

In another aspect, described herein is a peptide composition comprising one or more amino acid sequences selected from the group consisting of SEQ ID NOs: 1 to 45.

In some embodiments, the invention provides for an immunogenic peptide composition comprising one or more peptides selected from the group consisting of SEQ ID NOs: 1 to 45.

In some embodiments, the immunogenic peptide composition comprises two or more peptides selected from the group consisting of SEQ ID NOs: 1 to 45. In some embodiments, the immunogenic composition is administered to a subject. In some embodiments a peptide in the immunogenic peptide composition is displayed by an HLA class I molecule. In some embodiments, a peptide in the immunogenic peptide composition is a modified or an unmodified fragment of a BCR-ABL gene fusion. In some embodiments, the BCR-ABL gene fusion is b3a2 or b2a2. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic composition is administered in an effective amount to a subject to prevent chronic myelogenous leukemia (CIVIL), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CIVIL), acute lymphoblastic leukemia (ALL), acute myelogenous leukemia (AML), or breast invasive ductal carcinoma.

In some embodiments, the immunogenic peptide composition comprises three or more peptides selected from the group consisting of SEQ ID NOs: 1 to 45.

In another aspect, described herein are nucleic acid sequences encoding one or more amino acid sequences selected from the group consisting of SEQ ID NOs: 1 to 44.

In some embodiments, the invention provides for an immunogenic composition comprising nucleic acid sequences encoding one or more amino acid sequences selected from the group consisting of SEQ ID NOs: 1 to 44.

In some embodiments, the immunogenic composition is administered to a subject. In some embodiments, the immunogenic composition comprises nucleic acid sequences encoding two or more amino acid sequences selected from the group consisting of SEQ ID NOs: 1 to 44. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or an unmodified fragment of a BCR-ABL gene fusion. In some embodiments, the BCR-ABL gene fusion is b3a2 or b2a2. In some embodiments, the immunogenic composition is administered in an effective amount to a subject to prevent cancer. In some embodiments, the immunogenic composition is administered in an effective amount to a subject to treat cancer. In some embodiments, the immunogenic composition is administered in an effective amount to a subject to prevent chronic myelogenous leukemia (CML), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CML), acute lymphoblastic leukemia (ALL), acute myelogenous leukemia (AML), or breast invasive ductal carcinoma.

In some embodiments, the immunogenic composition comprises nucleic acid sequences encoding at least three amino acid sequences selected from the group consisting of SEQ ID NOs: 1 to 44.

In another aspect, described herein is a method of treating or preventing cancer by administering to a subject an immunogenic composition comprising nucleic acid sequences encoding one or more amino acid sequences selected from the group consisting of SEQ ID NOs: 1 to 44.

In some embodiments, the immunogenic composition comprises nucleic acid sequences encoding two or more amino acid sequences selected from the group consisting of SEQ ID NOs: 1 to 44.

In another aspect, described herein is a peptide composition comprising one or more amino acid sequences selected from the group consisting of SEQ ID NOs: 1 to 44.

In some embodiments, the invention provides for an immunogenic peptide composition comprising one or more peptides selected from the group consisting of SEQ ID NOs: 1 to 44.

In some embodiments, the immunogenic peptide composition comprises two or more peptides selected from the group consisting of SEQ ID NOs: 1 to 44. In some embodiments a peptide in the immunogenic peptide composition is displayed by an HLA class I molecule. In some embodiments, a peptide in the immunogenic peptide composition is a modified or an unmodified fragment of a BCR-ABL gene fusion. In some embodiments, the BCR-ABL gene fusion is b3a2 or b2a2. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic composition is administered in an effective amount to a subject to prevent chronic myelogenous leukemia (CIVIL), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CIVIL), acute lymphoblastic leukemia (ALL), acute myelogenous leukemia (AML), or breast invasive ductal carcinoma.

In some embodiments, the immunogenic peptide composition comprises three or more peptides selected from the group consisting of SEQ ID NOs: 1 to 44.

In another aspect, described herein is a method of treating or preventing cancer in a subject comprising administering to the subject an immunogenic peptide composition comprising one or more peptides selected from the group consisting of SEQ ID NOs: 1 to 44.

In some embodiments, the immunogenic peptide composition comprises two or more peptides selected from the group consisting of SEQ ID NOs: 1 to 44.

In another aspect, described herein are nucleic acid sequences encoding one or more amino acid sequences selected from the group consisting of SEQ ID NOs: 46 to 112.

In some embodiments, the nucleic acid sequences encode two or more amino acid sequences selected from the group consisting of SEQ ID NOs: 46 to 112.

In some embodiments, the invention provides for an immunogenic composition comprising nucleic acid sequences encoding one or more amino acid sequences selected from the group consisting of SEQ ID NOs: 46 to 112.

In some embodiments, the immunogenic composition comprises nucleic acid sequences encoding two or more amino acid sequences selected from the group consisting of SEQ ID NOs: 46 to 112. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or an unmodified fragment of a BCR-ABL gene fusion. In some embodiments, the BCR-ABL gene fusion is b3a2 or b2a2. In some embodiments, the immunogenic composition is administered in an effective amount to a subject to prevent cancer. In some embodiments, the immunogenic composition is administered in an effective amount to a subject to treat cancer. In some embodiments, the immunogenic composition comprises nucleic acid sequences encoding at least three amino acid sequences selected from the group consisting of SEQ ID NOs: 46 to 112. In some embodiments, the immunogenic composition is administered in an effective amount to a subject to prevent chronic myelogenous leukemia (CIVIL), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CIVIL), acute lymphoblastic leukemia (ALL), acute myelogenous leukemia (AML), or breast invasive ductal carcinoma.

In another aspect, described herein is a method of treating or preventing cancer by administering to a subject an immunogenic composition comprising nucleic acid sequences encoding one or more amino acid sequences selected from the group consisting of SEQ ID NOs: 46 to 112.

In some embodiments, the immunogenic composition comprises nucleic acid sequences encoding two or more amino acid sequences selected from the group consisting of SEQ ID NOs: 46 to 112.

In another aspect, described herein is a peptide composition comprising one or more amino acid sequences selected from the group consisting of SEQ ID NOs: 46 to 112.

In some embodiments, the invention provides for an immunogenic peptide composition comprising one or more peptides selected from the group consisting of SEQ ID NOs: 46 to 112.

In some embodiments, the immunogenic peptide composition comprises two or more peptides selected from the group consisting of SEQ ID NOs: 46 to 112. In some embodiments a peptide in the immunogenic peptide composition is displayed by an HLA class II molecule. In some embodiments, a peptide in the immunogenic peptide composition is a modified or an unmodified fragment of a BCR-ABL gene fusion. In some embodiments, the BCR-ABL gene fusion is b3a2 or b2a2. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic composition is administered in an effective amount to a subject to prevent chronic myelogenous leukemia (CIVIL), acute lymphoblastic leukemia (ALL), acute myelogenous leukemia (AML), or breast invasive ductal carcinoma. In some embodiments, the immunogenic composition is administered in an effective amount to a subject to treat chronic myelogenous leukemia (CIVIL), acute lymphoblastic leukemia (ALL), acute myelogenous leukemia (AML), or breast invasive ductal carcinoma.

In another aspect, described herein is a method of treating or preventing cancer in a subject comprising administering to the subject an immunogenic peptide composition comprising one or more peptides selected from the group consisting of SEQ ID NOs: 46 to 112.

In some embodiments, the immunogenic peptide composition comprises two or more peptides selected from the group consisting of SEQ ID NOs: 46 to 112.

BRIEF DESCRIPTION OF THE DRAWINGS

The following figures depict illustrative embodiments of the invention.

FIG. 8 is a table showing the respective probabilities of target presentations for various mutated protein targets across different cancers.

FIG. 10 is a script showing an example Python implementation of the M$_{\text{ERGE}}$M$_{\text{ULTI}}$ function for combined vaccine design procedures.

DETAILED DESCRIPTION

Figure 1:
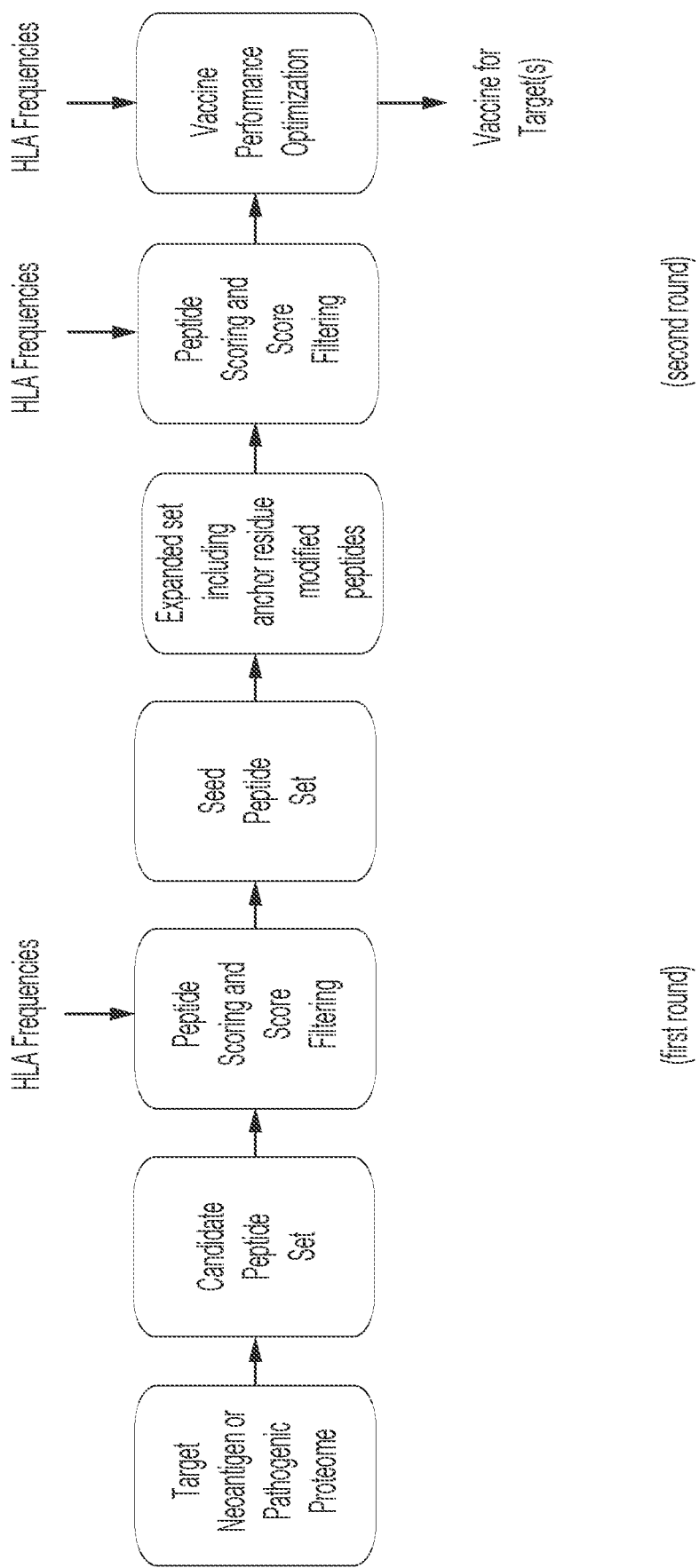
FIG. 1 is a flow chart of a vaccine optimization method.

In some embodiments, the disclosure provides for peptide vaccines that incorporate peptide sequences that will be displayed by Major Histocompatibility Complex (MHC) molecules on cells and train the immune system to recognize cancer or pathogen diseased cells. In some embodiments, the disclosure provides for peptide vaccines that that incorporate peptide sequences that will be displayed by Major Histocompatibility Complex (MHC) molecules on cells to induce therapeutic tolerance in antigen-specific immunotherapy for autoimmune diseases (Alhadj Ali et al., 2017, Gibson, et al. 2015). In some embodiments, a peptide vaccine is a composition that consists of one or more peptides. In some embodiments, a peptide vaccine is an mRNA or DNA construct administered for expression in vivo that encodes for one or more peptides.

Peptide display by an MHC molecule is necessary, but not sufficient, for a peptide to be immunogenic and cause the recognition of the resulting peptide-MHC complex by an individual's T cells to trigger T cell activation, expansion, and immune memory. In some embodiments, ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) are used to scoring peptide display (e.g., a peptide immunogenicity that requires peptide binding) by an MHC molecule (e.g., HLA allele) (e.g., measured as a peptide-HLA binding score). In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be used to produce a peptide-HLA immunogenicity metric with respect to a peptide and an HLA allele in a given experimental context or individual. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be combined with machine learning based predictions for scoring peptide display (e.g., binding affinity) by an MHC molecule (e.g., HLA allele) (e.g., measured as a peptide-HLA binding score) or for determining a peptide-HLA immunogenicity metric. In some embodiments, MHCflurry or NetMHCpan (Reynisson et al., 2020) computational methods (as known in the art) are used to predict MHC class I display of a peptide by an HLA allele (see Table 1). In some embodiments, the NetMHCIIpan computational method (Reynisson et al., 2020) is used to predict MHC class II display of a peptide by an HLA allele (see Table 2).

In some embodiments, computational methods such as MHCflurry (Odonnell et al., 2018, Odonnell et al., 2020, incorporated by reference in their entireties herein), NetMHCpan (Reynisson et al., 2020, incorporated by reference in its entirety herein), and NetMHCIIpan (Reynisson et al., 2020) are used to predict either MHC class I (MHCflurry, NetMHCpan) or class II (NetMHCIIpan) display of peptides by an HLA allele. In other embodiments, other methods of determining peptide-HLA binding are used as disclosed in International Publication No. WO 2005/042698, incorporated by reference in its entirety herein. NetMHCpan-4.1 and NetMHCIIpan-4.0 utilize the NNAlign_MA algorithm (Alvarez et al., 2019, incorporated by reference in its entirety herein) for predicting peptide-HLA binding. NNAlign_MA is in turn based upon the NNAlign (Nielsen et al., 2009, Nielsen et al., 2017, incorporated by reference in their entireties herein) neural network. NetMHCpan-4.1 (Reynisson et al., 2020) uses NNAlign_MA networks with at least 180 inputs that describe the peptide sequence (9×20=180 inputs). Networks with both 56 and 66 hidden neurons and two outputs are utilized (Alvarez et al., 2019). Each network architecture (56 or 66 hidden neurons) is trained with 5 different random parameter initializations and 5-fold cross-validation resulting in a total of 50 individual trained networks (2 architectures×5 initializations×5 cross-validation). These 50 trained networks are used as an ensemble with 25 networks having at least 10,800 parameters (180 inputs×56 neurons) and 25 networks consist of at least 11,880 parameters (180 inputs×66 neurons). Thus, the ensemble of 50 networks in NetMHCpan-4.1 consists of at least 567,000 parameters that must be evaluated with at least 567,000 arithmetic operations for computing peptide-MHC binding. NetMHCIIpan-4.1 (Reynisson et al., 2020) uses NNAlign_MA networks with at least 180 inputs that describe the peptide sequence (9×20=180 inputs). Networks with 2, 10, 20, 40, and 60 hidden neurons and two outputs are utilized (Alvarez et al., 2019). Each network architecture (2, 10, 20, 40, or 60 hidden neurons) is trained with 10 different random parameter initializations and 5-fold cross-validation resulting in a total of 250 individual trained networks (5 architectures×10 initializations×5 cross-validation). These 250 trained networks are used as an ensemble with 50 networks having at least 360 parameters (180 inputs×2 neurons), 50 networks having at least 1800 parameters (180 inputs×10 neurons), 50 networks having at least 3600 parameters (180 inputs×20 neurons), 50 networks having at least 7200 parameters (180 inputs×40 neurons), and 50 networks having at least 10,800 parameters (180 inputs×60 neurons). Thus, the ensemble of 250 networks in NetMHCIIpan-4.0 consists of at least 1,188,000 parameters that must be evaluated with at least 1,188,000 arithmetic operations for computing peptide-MHC binding.

A peptide is displayed by an MHC molecule when it binds within the groove of the MHC molecule and is transported to the cell surface where it can be recognized by a T cell receptor. A target peptide refers to a foreign peptide or a self-peptide. In some embodiments, a peptide that is part of the normal proteome in a healthy individual is a self-peptide, and a peptide that is not part of the normal proteome is a foreign peptide. In some embodiments, target peptides can be part of the normal proteome that exhibit aberrant expression (e.g., cancer-testis antigens such as NY-ESO-1). Foreign peptides can be generated by mutations in normal self-proteins in tumor cells that create epitopes called neoantigens, or by pathogenic infections. In some embodiments, a neoantigen is any subsequence of a human protein, where the subsequence contains one or more altered amino acids or protein modifications that do not appear in a healthy individual. Therefore, in this disclosure, foreign peptide refers to an amino acid sequence encoding a fragment of a target protein/peptide (or a full-length protein/peptide), the target protein/peptide consisting of: a neoantigen protein, a pathogen proteome, or any other undesired protein that is non-self and is expected to be bound and displayed by an HLA allele.

The BCR-ABL mutation is the result of the abnormal joining of the BCR gene from chromosome 22 with the ABL gene from chromosome 9 that results in a fusion of the two genes on chromosome 22. Differences in the fusion product formed result in different BCR-ABL transcripts, with b3a2 (also known as e14a2) and b2a2 (also known as e13a2) being the most prevalent. In a study of two hundred BCR-ABL affected patients 42% expressed b2a2, 41% expressed b3a2, and 18% expressed both transcripts (Jain et al., 2016). The abnormal b2a2 and b3a2 BCR-ABL fusions create novel protein sequences that contain foreign peptides at the junction of BCL and ABL. Disclosed herein is how these foreign peptides and their derivatives are used as neoantigen epitopes for vaccine design.

A challenge for the design of peptide vaccines is the diversity of human MHC alleles (HLA alleles) that each have specific preferences for the peptide sequences they will display. The Human Leukocyte Antigen (HLA) loci, located within the MHC, encode the HLA class I and class II molecules. There are three classical class I loci (HLA-A, HLA-B, and HLA-C) and three loci that encode class II molecules (HLA-DR, HLA-DQ, and HLA-DP). An individual's HLA type describes the alleles they carry at each of these loci. Peptides of length of between about 8 and about 11 residues can bind to HLA class I (or MHC class I) molecules whereas those peptides of length of between about 13 and about 25 residues bind to HLA class II (or MHC class II) molecules (Rist et al., 2013; Chicz et al., 1992). Human populations that originate from different geographies have differing frequencies of HLA alleles, and these populations exhibit linkage disequilibrium between HLA loci that result in population specific haplotype frequencies. In some embodiments, methods are disclosed for creating effective vaccines that include consideration of the HLA allelic frequency in the target population, as well as linkage disequilibrium between HLA genes to achieve a set of peptides that is likely to be robustly displayed.

The present disclosure provides for compositions, systems, and methods of vaccine designs that produce immunity to single or multiple targets. In some embodiments, a target is a neoantigen protein sequence, a pathogen proteome, or any other undesired protein sequence that is non-self and is expected to be bound and displayed by an HLA molecule (also referred to herein as an HLA allele). When a target is present in an individual, it may result in multiple peptide sequences that are displayed by a variety of HLA alleles. In some embodiments, it may be desirable to create a vaccine that includes selected self-peptides, and thus these selected self-peptides are considered to be the target peptides for this purpose.

The term peptide-HLA binding is defined to be the binding of a peptide to an HLA allele, and can either be computationally predicted, experimentally observed, or computationally predicted using experimental observations. The metric of peptide-HLA binding can be expressed as affinity, percentile rank, binary at a predetermined threshold, probability, or other metrics as are known in the art. The term peptide-HLA immunogenicity metric is defined as the activation of T cells based upon their recognition of a peptide when bound by an HLA allele. The term peptide-HLA immunogenicity score is another term for a peptide-HLA immunogenicity metric, and the terms are interchangeable. A peptide-HLA immunogenicity metric can vary from individual to individual, and the metric for peptide-HLA immunogenicity can be expressed as a probability, a binary indicator, or other metric that relates to the likelihood that a peptide-HLA combination will be immunogenic. In some embodiments, peptide-HLA immunogenicity is defined as the induction of immune tolerance based upon the recognition of a peptide when bound by an HLA allele. A peptide-HLA immunogenicity metric can be computationally predicted, experimentally observed, or computationally predicted using experimental observations. In some embodiments, a peptide-HLA immunogenicity metric is based only upon peptide-HLA binding, since peptide-HLA binding is necessary for peptide-HLA immunogenicity. In some embodiments, peptide-HLA immunogenicity data or computational predictions of peptide-HLA immunogenicity can be included and combined with scores for peptide display in the methods disclosed herein. One way of combining the scores is using immunogenicity data for peptides assayed for immunogenicity in diseased or vaccinated individuals and assigning peptides to the HLA allele that displayed them in the individual by choosing the HLA allele that computational methods predict has the highest likelihood of display. For peptides that are not experimentally assayed, computational predictions of display can be used. In some embodiments, different computational methods of predicting peptide-HLA immunogenicity or peptide-HLA binding can be combined (Liu et al., 2020b). For a given set of peptides and a set of HLA alleles, the term peptide-HLA hits is the number of unique combinations of peptides and HLA alleles that exhibit peptide-HLA immunogenicity or binding at a predetermined threshold. For example, a peptide-HLA hit of 2 can mean that one peptide is predicted to be bound (or trigger T cell activation) by two different HLA alleles, two peptides are predicted to be bound (or trigger T cell activation) by two different HLA alleles, or two peptides are predicted to be bound (or trigger T cell activation) by the same HLA allele. For a given set of peptides and HLA frequencies, HLA haplotype frequencies, or HLA diplotype frequencies, the expected number of peptide-HLA hits is the average number of peptide-HLA hits in each set of HLAs that represent an individual, weighted by their frequency of occurrence.

Because immunogenicity may vary from individual to individual, one method to increase the probability of vaccine efficacy is to use a diverse set of target peptides (e.g., at least two peptides) to increase the chances that some subset of them will be immunogenic in a given individual. Prior research using mouse models has shown that most MHC displayed peptides are immunogenic, but immunogenicity varies from individual to individual as described in Croft et al. (2019). In some embodiments, experimental peptide-HLA immunogenicity data are used to determine which target peptides and their modifications will be effective immunogens in a vaccine.

Considerations for the design of peptide vaccines, are outlined in Liu et al., Cell Systems 11, Issue 2, p. 131-146 (Liu et al., 2020) and (Liu et al., 2020b) and U.S. Pat. No. 11,058,751 which are incorporated by reference in their entireties herein.

Certain target peptides may not bind with high affinity to a wide range of HLA molecules. To increase the binding of target peptides to HLA molecules, their amino acid composition can be altered to change one or more anchor residues or other residues. In some embodiments, to increase the immunogenicity of a target peptide when displayed by HLA molecules, a target peptide's amino acid composition can be altered to change one or more residues. Anchor residues are amino acids that interact with an HLA molecule and have the largest influence on the affinity of a peptide for an HLA molecule. Peptides with one or more altered amino acid residues are called heteroclitic peptides. In some embodiments, heteroclitic peptides include target peptides with residue modifications at anchor positions. In some embodiments, heteroclitic peptides include target peptides with residue modifications at non-anchor positions. In some embodiments, heteroclitic peptides include target peptides with residue modifications that include unnatural amino acids and/or amino acid derivatives. Modifications to create heteroclitic peptides can improve the binding of peptides to both MHC class I and MHC class II molecules, and the modifications required can be both peptide and MHC class specific. Since peptide anchor residues face the MHC molecule groove, they are less visible than other peptide residues to T cell receptors. Thus, heteroclitic peptides with anchor residue modifications have been observed to induce a T cell response where the stimulated T cells also respond to unmodified peptides. It has been observed that the use of heteroclitic peptides in a vaccine can improve a vaccine's effectiveness (Zirlik et al., 2006). In some embodiments, the immunogenicity of heteroclitic peptides are experimentally determined and their ability to activate T cells that also recognize the corresponding base (also called seed) peptide of the heteroclitic peptide is determined, as is known in the art (Houghton et al., 2007). In some embodiments, these assays of the immunogenicity and cross-reactivity of heteroclitic peptides are performed when the heteroclitic peptides are displayed by specific HLA alleles.

Peptide Vaccines to Induce Immunity to One or More Targets

In some embodiments, a method is provided for formulating peptide vaccines using a single vaccine design for one or more targets. In some embodiments, a single target is a foreign protein with a specific mutation (e.g., KRAS G12D). In some embodiments, a single target is a self-protein (e.g., a protein that is overexpressed in tumor cells such as cancer/testis antigens). In some embodiments, a single target is a pathogen protein (e.g., a protein contained in a viral proteome). In some embodiments, multiple targets can be used (e.g., foreign peptides derived from BCL-ABL transcripts b2a2 and b3a2).

In some embodiments, the method includes extracting peptides to construct a candidate set from all target proteome sequences (e.g., entire KRAS G12D protein) as described in Liu et al. (2020).

Figure 2:
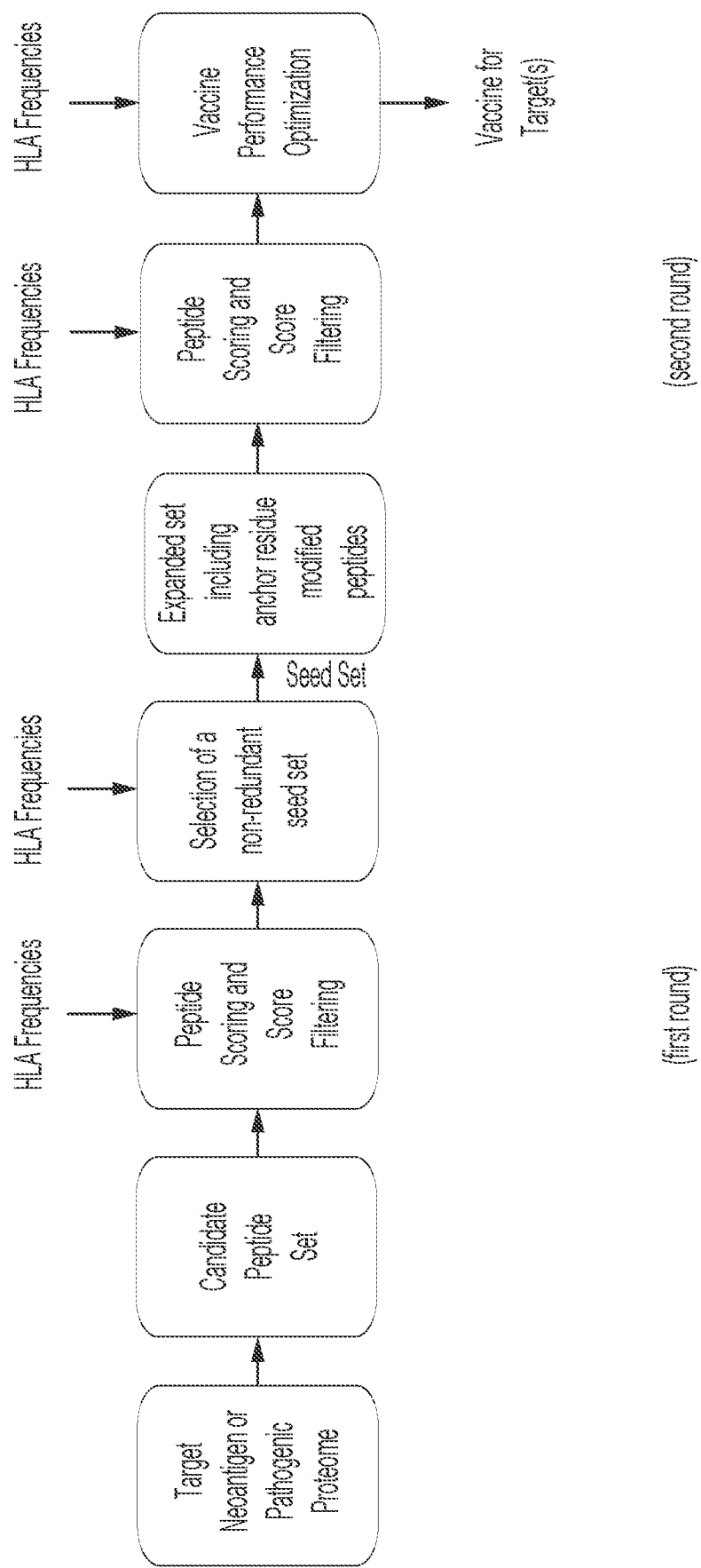
FIG. 2 is a flow chart of a vaccine optimization method with seed set compression.

FIGS. 1 and 2 depict flow charts for example vaccine design methods that can be used for MHC class I or MHC class II vaccine design. A Candidate Peptide Set (see FIGS. 1 and 2) is comprised of target peptides extracted by windowing an input protein sequence. In some embodiments, extracted target peptides are of amino acid length of between about 8 and about 10 (e.g., for MHC class I binding (Rist et al., 2013)). In some embodiments, the extracted target peptides presented by MHC class I molecules are longer than 10 amino acid residues, such as 11 residues (Trolle et al., 2016). In some embodiments, extracted target peptides are of length between about 13 and about 25 (e.g., for class II binding (Chicz et al., 1992)). In some embodiments, sliding windows of various size ranges described herein are used over the entire proteome. In some embodiments, other target peptide lengths for MHC class I and class II sliding windows can be utilized. In some embodiments, computational predictions of proteasomal cleavage are used to filter or select peptides in the candidate set. One computational method for predicting proteasomal cleavage is described by Nielsen et al. (2005). In some embodiments, peptide mutation rates, glycosylation, cleavage sites, or other criteria can be used to filter peptides as described in Liu et al. (2020). In some embodiments, peptides can be filtered based upon evolutionary sequence variation above a predetermined threshold. Evolutionary sequence variation can be computed with respect to other species, other pathogens, other pathogen strains, or other related organisms. In some embodiments, a first peptide set is the candidate set.

In some embodiments, for the design of vaccines for foreign peptides that are generated by abnormal gene fusions, target peptides are extracted for inclusion in the Candidate Peptide Set from the gene fusion product where each extracted target peptide includes the breakpoint between the two genes. For example, in some embodiments for the design of the BCR-ABL vaccines, the BCR-ABL b3a2 (e14a2) and b2a2 (e13a2) chimeric protein sequences were obtained from NCBI (GenBank ID CAA10376.1 and CAA10377.1, respectively). For each isoform, sliding windows of length 8-11 (MHC class I) and 13-25 (MHC class II) were extracted around the BCR-ABL breakpoint. Sliding windows can be extracted using the procedures described herein in "MHC Class I Vaccine Design Procedure" and "MHC Class II Vaccine Design Procedure" where $P_{1 \ldots n}$ contains the chimeric protein sequence, t specifies the position of the breakpoint in the chimeric protein sequence, and s=true. For b3a2, the BCR-ABL junction disrupts a triplet codon, yielding a novel lysine ("K") at the breakpoint (Clark et al., 2001). For b2a2, a codon disruption at the junction causes Asp to be altered to Glu, but this novel amino acid is also present at the normal a1a2 junction (Clark et al., 2001). Thus, for b3a2, all resulting windows spanning the "K" breakpoint were retained. For b2a2, only windows containing the sequence "KEE" were retained, eliminating windows that are found solely in BCR or ABL protein sequences. This procedure can be applied to generating vaccines for other abnormal gene fusions by identifying the breakpoint between the fused genes and utilizing the described windowing strategy.

As shown in FIGS. 1-2, in some embodiments, the next step of the method includes scoring the target peptides in the candidate set for peptide-HLA binding to all considered HLA alleles as described in Liu et al. (2020) and Liu et al. (2020b). In some embodiments, a first peptide set is the candidate set after scoring the target peptides. Scoring can be accomplished for human HLA molecules, mouse H-2 molecules, swine SLA molecules, or MHC molecules of any species for which prediction algorithms are available or can be developed. Thus, vaccines targeted at non-human species can be designed with the method. Scoring metrics can include the affinity for a target peptide to an HLA allele in nanomolar, eluted ligand, presentation, and other scores that can be expressed as percentile rank or any other metric. The candidate set may be further filtered to exclude peptides whose predicted binding cores do not contain a particular pathogenic or neoantigen target residue of interest or whose predicted binding cores contain the target residue in an anchor position. The candidate set may also be filtered for target peptides of specific lengths, such as length 9 for MHC class I, for example. In some embodiments, scoring of target peptides is accomplished with experimental data or a combination of experimental data and computational prediction methods. When computational models are unavailable to make peptide-HLA binding predictions for particular (peptide, HLA) pairs, the binding value for such pairs can be defined by the mean, median, minimum, or maximum immunogenicity value taken over supported pairs, a fixed value (such as zero), or inferred using other techniques, including a function of the prediction of the most similar (peptide, HLA) pair available in the scoring model.

In some embodiments, foreign peptides created by abnormal gene fusions are not eliminated when they contain a fusion breakpoint that falls on an MHC Class I or Class II anchor position for an HLA allele. For example, for the design of the BCL-ABL vaccines for MHC class I, no windows are eliminated when the BCR-ABL breakpoint falls within a peptide anchor position. For MHC class II, the scoring model requires the breakpoint to lie within the predicted 9-mer binding core for a given HLA (in any position), and scores for peptide-HLA pairs not meeting this criterion are eliminated. In some embodiments, for the design of BCR-ABL vaccines for MHC class I, windows are eliminated if the BCR-ABL breakpoint falls within a peptide anchor position. In some embodiments, for the design of BCR-ABL vaccines for MHC class II, peptide-HLA scores are eliminated if the BCR-ABL breakpoint lies within an anchor position of the predicted 9-mer binding core for a given peptide-HLA pair. In some embodiments, for the design of MHC class II vaccines, the gene fusion breakpoint can lie in any position either inside or outside of the predicted 9-mer binding core for a given peptide-HLA pair.

In some embodiments, a base set (also referred to as seed set herein) is constructed by selecting peptides from the scored candidate set using individual peptide-HLA binding or immunogenicity criteria (e.g., first peptide set) (FIG. 1). In some embodiments, since a given peptide has multiple peptide-HLA scores, the selection can be based on the peptide-HLA binding score or peptide-HLA immunogenicity metric with the best affinity or highest immunogenicity (e.g., predicted to bind the strongest or activate T cells the most for a given HLA allele). The criteria used for scoring peptide-HLA binding during the scoring procedure can accommodate different goals during the base set selection and vaccine design phases. For example, a target peptide with peptide-HLA binding affinities of 500 nM may be displayed by an individual that is diseased, but at a lower frequency than a target peptide with a 50 nM peptide-HLA binding affinity. During the combinatorial design phase of a vaccine, a more constrained affinity criteria may be used (e.g., when selecting a third peptide set, the Vaccine for Target(s) in FIGS. 1 and 2), such a 50 nM, to increase the probability that a vaccine peptide will be found and displayed by HLA molecules. In some embodiments, a relatively less constrained threshold (e.g., less than about 1000 nM or less than about 500 nM) of peptide-HLA immunogenicity or peptide-HLA binding is used as a first threshold for filtering candidate peptide-HLA scores (the first Peptide Scoring and Score Filtering step in FIGS. 1 and 2) and a relatively more constrained second threshold (e.g., less than about 50 nM) is used for filtering expanded set peptide-HLA scores (the second Peptide Filtering and Scoring step in FIGS. 1 and 2) for their scores for specific HLA alleles. In some embodiments, specific peptide-HLA scores are not used for modified peptides for a given HLA for vaccine design when their unmodified counterpart peptide does not pass the first less constrained threshold. This filtering of peptide-HLA scores is based on the observation that peptides that are not immunogenic enough for vaccine inclusion may be antigenic (meet the first threshold) and thus recognized by T cell clonotypes expanded by a vaccine. A peptide is antigenic when it is recognized by a T cell receptor and results in a response such as CD8+ T cell cytotoxicity or CD4+ cell activation. Derivatives of an antigenic peptide may be strongly immunogenic, included in a vaccine, and thus activate and expand T cells that recognize the antigenic peptide. The expansion of T cells that recognize an unmodified antigenic peptide can provide an immune response that contributes to disease control. In some embodiments, peptides are scored for third peptide set (Vaccine for Target(s) in FIGS. 1 and 2) potential inclusion that have peptide-HLA binding affinities less than about 500 nM. In some embodiments, peptides are selected for the base set that have peptide-HLA binding affinities less than about 1000 nM for at least one HLA allele. Alternatively, predictions of peptide-HLA immunogenicity can be used to qualify target peptides for base set inclusion. In some embodiments, experimental observations of the immunogenicity of peptides in the context of their display by HLA alleles or experimental observation of the binding of peptides to HLA alleles can be used to score peptides for binding to HLA alleles or peptide-HLA immunogenicity.

In some embodiments, experimental observations of the display of peptides by specific HLA alleles in tumor cells can be used to score peptides for peptide-HLA binding or peptide-HLA immunogenicity. In some embodiments, experimental observations of the display of peptides tumor cells by a specific HLA allele can be used to score peptides for peptide-HLA binding or peptide-HLA immunogenicity for that HLA allele. In some embodiments, experimental observations of the display of peptides tumor cells can be used to score peptides for peptide-HLA binding or peptide-HLA immunogenicity, with the HLA allele(s) for a specific observed peptide selected from the HLA alleles present in the tumor that meet a predicted peptide-HLA binding or immunogenicity threshold. In some embodiments, mass spectrometry is used to experimentally determine the display of peptides by tumor cells as described by Bear et al. (2021) or Wang et al. (2019) and these data are used to score for peptide-HLA binding or peptide-HLA immunogenicity. In some embodiments, mass spectrometry is used to experimentally determine the display of peptides by tumor cells, and these experimental data are used to qualify the inclusion of base set (seed set) peptides for one or more HLA alleles for a vaccine. In some embodiments, mass spectrometry is used to experimentally determine the display of a peptide by tumor cells, and these experimental data are used to exclude peptide-HLA binding scores or peptide-HLA immunogenicity scores for the peptide when the peptide is not observed to be displayed by an HLA allele by mass spectrometry. In some embodiments, mass spectrometry is used to experimentally determine the display of peptides by tumor cells in an individual, and these experimental data are used to qualify the inclusion of base set (seed set) peptides for that individual for one or more HLA alleles. In some embodiments, mass spectrometry is used to experimentally determine the display of a peptide by tumor cells in an individual, and these experimental data are used to exclude peptide-HLA binding scores or peptide-HLA immunogenicity scores for the peptide when the peptide is not observed to be displayed by an HLA allele by mass spectrometry. In some embodiments, computational predictions of the immunogenicity of a peptide in the context of display by HLA alleles can used for scoring such as the methods of Ogishi et al. (2019) or Bulik-Sullivan et al. (2019).

In some embodiments, a peptide-HLA score or a peptide-HLA immunogenicity score for a first peptide in the base set (seed set) for a given HLA allele is eliminated and not considered during vaccine design if the wild-type peptide corresponding to the first peptide (e.g. the unmutated naturally occurring form for the peptide or a peptide in the respective species within a defined sequence edit distance) has a peptide-HLA score or a peptide-HLA immunogenicity score for the same HLA allele within a defined threshold. The threshold can be based upon the difference of the scores of the first peptide and the wild-type peptide, the ratio of the scores of the first peptide and the wild-type peptide, the score of the wild-type peptide, or other metrics. The defined threshold can be either greater than or less than a specified value. In some embodiments, the threshold is defined so that the wild-type peptide is not predicted to be presented. In some embodiments, when a peptide-HLA score or peptide-HLA immunogenicity score is eliminated for a first peptide during vaccine design, then peptide-HLA scores or peptide-HLA immunogenicity scores for all of its derivatives (e.g., heteroclitic peptide derivatives) for the same HLA allele are also eliminated and not considered during vaccine design.

In some embodiments, the method further includes running the OptiVax-Robust algorithm as described in Liu et al. (2020) using the HLA haplotype frequencies of a population on the scored candidate set to construct a base set (also referred to as seed set herein) of target peptides (FIG. 2). In some embodiments, HLA diplotype frequencies can be provided to OptiVax. OptiVax-Robust includes algorithms to eliminate peptide redundancy that arises from the sliding window approach with varying window sizes, but other redundancy elimination measures can be used to enforce minimum edit distance constraints between target peptides in the candidate set. The size of the seed set is determined by a point of diminishing returns of population coverage as a function of the number of target peptides in the seed set. Other criteria can also be used, including a minimum number of vaccine target peptides, maximum number of vaccine target peptides, and desired predicted population coverage. In some embodiments, a predetermined population coverage is less than about 0.4, between about 0.4 and 0.5, between about 0.5 and 0.6, between about 0.6 and 0.7, between about 0.7 and 0.8, between about 0.8 and 0.9, or greater than about 0.9. Another possible criterion is a minimum number of expected peptide-HLA binding hits in each individual. In alternate embodiments, the method further includes running the OptiVax-Unlinked algorithm as described in Liu et al. (2020) instead of OptiVax-Robust.

The OptiVax-Robust method uses binary predictions of peptide-HLA immunogenicity, and these binary predictions can be generated as described in Liu et al. (2020b). The OptiVax-Unlinked method uses the probability of target peptide binding to HLA alleles and can be generated as described in Liu et al. (2020). In some embodiments, OptiVax-Unlinked and EvalVax-Unlinked are used with the probabilities of peptide-HLA immunogenicity. Either method can be used for the purposes described herein, and thus the term "OptiVax" refers to either the Robust or Unlinked method. In some embodiments, the HLA haplotype or HLA allele frequencies of a population provided to OptiVax for vaccine design describe the world's population. In alternative embodiments, the HLA haplotype or HLA allele frequencies of a population provided to OptiVax for vaccine design are specific to a geographic region. In alternative embodiments, the HLA haplotype or HLA allele frequencies of a population provided to OptiVax for vaccine design are specific to an ancestry. In alternative embodiments, the HLA haplotype or HLA allele frequencies of a population provided to OptiVax for vaccine design are specific to a race. In alternative embodiments, the HLA haplotype or HLA allele frequencies of a population provided to OptiVax for vaccine design are specific to individuals with risk factors such as genetic indicators of risk, age, exposure to chemicals, alcohol use, chronic inflammation, diet, hormones, immunosuppression, infectious agents, obesity, radiation, sunlight, or tobacco use. In alternative embodiments, the HLA haplotype or HLA allele frequencies of a population provided to OptiVax for vaccine design are specific to individuals that carry certain HLA alleles. In alternative embodiments, the HLA diplotypes provided to OptiVax for vaccine design describe a single individual and are used to design an individualized vaccine.

In some embodiments, the base (or seed) set of target peptides (e.g., first peptide set) that results from OptiVax application to the candidate set of target peptides describes a set of unmodified target peptides that represent a possible compact vaccine design (Seed Set in FIG. 2). A base peptide is a target peptide that is included in the base or seed peptide set (e.g., first peptide set). In some embodiments, the seed set (e.g., first peptide set) is based upon filtering candidate peptide scores by predicted or observed affinity or immunogenicity with respect to HLA molecules (Seed Set in FIG. 1). However, to improve the display of the target peptides in a wide range of HLA haplotypes as possible, some embodiments include modifications of the seed (or base) set. In some embodiments, experimental assays can be used to ensure that a modified seed (or base) peptide activates T cells that also recognize the base/seed peptide.

For a given target peptide, the optimal anchor residue selection may depend upon the HLA allele that is binding to and displaying the target peptide and the class of the HLA allele (MHC class I or class II). A seed peptide set (e.g., first peptide set) can become an expanded set by including anchor residue modified peptides of either MEW class I or II peptides (FIGS. 1-2). Thus, one aspect of vaccine design is considering how to select a limited set of heteroclitic peptides that derive from the same target peptide for vaccine inclusion given that different heteroclitic peptides will have different and potentially overlapping population coverages.

In some embodiments, all possible anchor modifications for each base set of target peptide are considered. There are typically two anchor residues in peptides bound by MHC class I molecules, typically at positions 2 and 9 for 9-mer peptides. In some embodiments, anchors for 8-mers, 10-mers, and 11-mers are found at positions 2 and n, where n is the last position (8, 10, and 11, respectively). For MHC class I molecules, the last position n is called the "C" position herein for carboxyl terminus. In some embodiments, at each anchor position, 20 possible amino acids are attempted in order to select the best heteroclitic peptides. Thus, for MEW class I binding, 400 (i.e., 20 amino acids by 2 positions=$20^2$) minus 1 heteroclitic peptides are generated for each base target peptide. There are typically four anchor residues in peptides bound by MHC class II molecules, typically at positions 1, 4, 6, and 9 of the 9-mer binding core. Thus, for MHC class II binding there are 160,000 (i.e., 20 amino acids by 4 positions=$20^4$) minus 1 heteroclitic peptides generated for each base target peptide. In some embodiments, more than two (MHC class I) or four (MEW class II) positions are considered as anchors. Other methods, including Bayesian optimization, can be used to select optimal anchor residues to create heteroclitic peptides from each seed (or base) set peptide. Other methods of selecting optimal anchor residues are presented in "Machine learning optimization of peptides for presentation by class II MHCs" by Dai et al. (2020), incorporated in its entirety herein. In some embodiments, the anchor positions are determined by the HLA allele that presents a peptide, and thus the set of heteroclitic peptides includes for each set of HLA specific anchor positions, all possible anchor modifications.

In some embodiments, for all of the target peptides in the base/seed set, new peptide sequences with all possible anchor residue modifications (e.g., MHC class I or class II) are created resulting in a new heteroclitic base set (Expanded set in FIGS. 1-2) that includes all of the modifications. In some embodiments, anchor residue modifications of a peptide are not included in the heteroclitic base set if one or more of the peptide's anchor residue positions contains a substitution mutation that distinguishes the peptide from a self-peptide. In some embodiments, anchor residue modifications of a base/seed peptide are only included in the heteroclitic base set for peptide positions that do not contain a substitution mutation that distinguishes the base/seed peptide from a self-peptide. In some embodiments, anchor residue modifications of a peptide are not included in the heteroclitic base set when one or more of the peptide's mutations does not occur between a pair of its adjacent anchor residues. In some embodiments, for all of the target peptides in the base/seed set, new peptide sequences with anchor residue modifications (e.g., MEW class I or class II) at selected anchor locations are created resulting in a new heteroclitic base set (Expanded set in FIGS. 1-2) that includes the selected modifications. In some embodiments, the anchor residue positions used for modifying peptides are selected from anchor residue positions determined by the HLA alleles considered during vaccine evaluation. In some embodiments, the heteroclitic base set (Expanded set in FIGS. 1-2) also includes the original seed (or base) set (Seed Peptide Set in FIGS. 1-2). In some embodiments, the heteroclitic base set includes amino acid substitutions at non-anchor residues. In some embodiments, modifications of base peptide residues is accomplished to alter binding to T cell receptors to improve therapeutic efficacy (Candia, et al. 2016). In some embodiments, the heteroclitic base set includes amino acid substitutions of non-natural amino acid analogs. The heteroclitic base set is scored for HLA affinity, peptide-HLA immunogenicity, or other metrics as described herein (another round of Peptide Scoring and Score Filtering as shown in FIGS. 1-2). In some embodiments, the scoring predictions may be further updated for pairs of heteroclitic peptide and HLA allele, eliminating pairs where a heteroclitic peptide has a seed (or base) peptide from which it was derived that is not predicted to be displayed by the HLA allele at a specified threshold of peptide-HLA binding score or a specified peptide-HLA immunogenicity metric. In some embodiments, the peptide-HLA scores may also be filtered to ensure that predicted binding cores of the heteroclitic peptide displayed by a particular HLA allele align exactly in position with the binding cores of the respective seed (or base) set target peptide for that HLA allele. In some embodiments, the scoring predictions are filtered for an HLA allele to ensure that the heteroclitic peptides considered for that HLA allele are only modified at anchor positions determined by that HLA allele. Scoring produces a metric of peptide-HLA immunogenicity for peptides and HLA alleles that can be either binary, a probability of immunogenicity, or other metric of immunogenicity such as peptide-HLA affinity or percent rank, and can be based on computational predictions, experimental observations, or a combination of both computational predictions and experimental observations. In some embodiments, probabilities of peptide-HLA immunogenicity are utilized by OptiVax-Unlinked. In some embodiments, heteroclitic peptides are included in experimental assays such as MIRA (Klinger et al., 2015) or ELISPOT to determine their peptide-HLA immunogenicity metric with respect to specific HLA alleles. In some embodiments, the methods of Liu et al. (2020b), can be used to incorporate MIRA data for heteroclitic peptides into a model of peptide-HLA immunogenicity. In some embodiments, peptide-HLA immunogenicity metrics of heteroclitic peptides are experimentally determined and their ability to activate T cells that also recognize the corresponding seed (or base) peptide of the heteroclitic peptide is performed as is known in the art to qualify the heteroclitic peptide for vaccine inclusion (e.g. Houghton et al., 2007). In some embodiments, these assays of the immunogenicity and cross-reactivity of heteroclitic peptides are performed when the heteroclitic peptides are displayed by specific HLA alleles.

In some embodiments, experimental observations of the display of heteroclitic peptides by specific HLA alleles in cells can be used to score peptides for peptide-HLA binding or peptide-HLA immunogenicity. In some embodiments, mass spectrometry is used to experimentally determine the display of heteroclitic peptides by cells as described by Bear et al. (2021) or Wang et al. (2019) and these data are used to score for peptide-HLA binding or peptide-HLA immunogenicity. In some embodiments, mass spectrometry is used to experimentally determine the display of heteroclitic peptides by cells, and these experimental data are used to qualify the inclusion of heteroclitic peptides for inclusion in a vaccine. In some embodiments, mass spectrometry is used to experimentally determine the display of a peptide by tumor cells, and these experimental data are used to exclude peptide-HLA binding scores or peptide-HLA immunogenicity scores for the peptide when the peptide is not observed to be displayed by an HLA allele by mass spectrometry. In some embodiments, mass spectrometry is used to experimentally determine the display of a heteroclitic peptide by cells with an HLA allele found in an individual, and these experimental data are used to qualify the inclusion of the heteroclitic peptide for inclusion in a vaccine for the individual. In some embodiments, mass spectrometry is used to experimentally determine the display of a peptide by tumor cells in an individual, and these experimental data are used to exclude peptide-HLA binding scores or peptide-HLA immunogenicity scores for the peptide when the peptide is not observed to be displayed by an HLA allele by mass spectrometry. In some embodiments, computational predictions of the immunogenicity of a heteroclitic peptide in the context of display by HLA alleles can used for scoring such as the methods of Ogishi et al. (2019) or Bulik-Sullivan et al. (2019).

In some embodiments, a peptide in the heteroclitic base set is removed if (1) one of its anchor positions for an HLA allele corresponds to the location of a mutation in the base/seed peptide from which it was derived that distinguishes the base/seed peptide from a self-peptide, and (2) if the peptide-HLA binding or peptide-HLA immunogenicity of the self-peptide is stronger than a specified threshold for self-peptide binding or immunogenicity. This eliminates peptides in the heteroclitic base set that may cross-react with self-peptides as a result of sharing TCR facing residues with self-peptides. In some embodiments, the threshold for self-peptide binding is between approximately 500 nM to 1000 nM.

In some embodiments, redundant peptides in the heteroclitic base set are removed. In some embodiments, a redundant peptide is a first heteroclitic peptide that has peptide-HLA immunogenicity scores or peptide-HLA binding scores that are less immunogenic for all scored HLAs than a second heteroclitic peptide in the heteroclitic base set, where both the first and second heteroclitic peptides are derived from the same base (or seed) peptide. In some embodiments, peptide redundancy is determined by only comparing peptide-HLA immunogenicity scores or peptide-HLA binding scores for HLA alleles where the peptide-HLA immunogenicity scores or peptide-HLA binding scores for both peptides for an HLA allele are more immunogenic than a given threshold (e.g., 50 nM for binding). In some embodiments, a redundant peptide is a first heteroclitic peptide that has an average peptide-HLA immunogenicity score or peptide-HLA binding score that is less immunogenic than the average peptide-HLA immunogenicity score or peptide-HLA binding score of a second heteroclitic peptide in the heteroclitic base set, where both the first and second heteroclitic peptides are derived from the same base (or seed) peptide, and the average scores are computed for HLA alleles where the peptide-HLA immunogenicity scores or peptide-HLA binding scores for both peptides for an HLA allele are more immunogenic than a given threshold (e.g., 50 nM for binding). In some embodiments, a redundant peptide is a first heteroclitic peptide that has a weighted peptide-HLA immunogenicity score or peptide-HLA binding score that is less immunogenic than the weighted peptide-HLA immunogenicity score or peptide-HLA binding score of a second heteroclitic peptide in the heteroclitic base set, where both the first and second heteroclitic peptides are derived from the same base (or seed) peptide, and where the weighting is determined by the frequency of the HLA allele in a human population, and the weighted scores are computed for HLA alleles where the peptide-HLA immunogenicity scores or peptide-HLA binding scores for both peptides for an HLA allele are more immunogenic that a given threshold (e.g., 50 nM for binding).

In some embodiments, the next step involves scoring the heteroclitic base set (the second peptide set) and filtering the resulting scores to create a second peptide set by comparing the peptide-HLA immunogenicity scores or peptide-HLA binding scores of the peptides for one or more HLA alleles to a threshold. In some embodiments, an affinity criterion of about 50 nM is used to increase the probability that a vaccine peptide will be found and displayed by HLA molecules. In some embodiments, the affinity criteria is more constrained than 50 nM (i.e., <50 nM). In some embodiments, the affinity criteria is more constrained than about 500 nM (i.e., <500 nM). In some embodiments, individual peptide-HLA binding scores or immunogenicity metrics are determined and thus a peptide may be retained as long as it meets the criteria for at least one HLA allele, and only peptide-HLA scores that meet the criteria are considered for vaccine design.

In some embodiments, the next step involves inputting the second peptide set to OptiVax to select a compact set of vaccine peptides that maximizes predicted vaccine performance (Vaccine Performance Optimization; FIGS. 1-2). In some embodiments, predicted vaccine performance is a function of expected peptide-HLA binding affinity (e.g., a function of the distribution of peptide-HLA binding affinities across all peptide-HLA combinations for a given peptide set, or weighted by the occurrence of the HLA alleles in a population or individual). In some embodiments, predicted vaccine performance is the expected population coverage of a vaccine. In some embodiments, predicted vaccine performance is the expected number peptide-HLA hits produced by a vaccine in a population or individual. In some embodiments, predicted vaccine performance requires a minimum expected number of peptide-HLA hits (e.g., 1, 2, 3, 4, 5, 6, 7, 8, or more) produced by a vaccine. In some embodiments, predicted vaccine performance is a function of population coverage and expected number of peptide-HLA hits desired produced by a vaccine. In some embodiments, predicted vaccine performance is a metric that describes the overall immunogenic properties of a vaccine where all of the peptides in the vaccine are scored for peptide-HLA immunogenicity for two or more HLA alleles (e.g., three or more HLA alleles). In some embodiments, predicted vaccine performance excludes immunogenicity contributions by selected HLA alleles above a maximum number of peptide-HLA hits (e.g., 1, 2, 3, 4, 5, 6, 7, 8, or more). In some embodiments, predicted vaccine performance excludes immunogenicity contributions of individual HLA diplotypes above a maximum number of peptide-HLA hits (e.g., 1, 2, 3, 4, 5, 6, 7, 8, or more). In some embodiments, predicted vaccine performance is the fraction of covered HLA alleles, which is the expected fraction of HLA alleles in each individual that have a minimum number of peptides (e.g., 1, 2, 3, 4, 5, 6, 7, 8, or more) with predicted peptide-HLA immunogenicity produced by a vaccine. In some embodiments, predicted vaccine performance is the expected fraction of HLA alleles in a single individual that have a minimum number of peptides (e.g., 1, 2, 3, 4, 5, 6, 7, 8, or more) with predicted peptide-HLA immunogenicity produced by a vaccine.

In some embodiments, a vaccine is designed by the iterative selection of peptides from the heteroclitic base set (also referred to as Expanded set as shown in FIGS. 1-2) at progressively less stringent criteria for predicted peptide immunogenicity or display. In some embodiments, a peptide is retained if at least one of its peptide-HLA scores is not eliminated by the thresholds employed. In some embodiments, OptiVax is first used to design a vaccine with a desired vaccine performance with specific peptide qualification criteria (e.g., seed HLA-peptide scores from the candidate set must bind to MHC molecules at 500 nM or stronger, and peptide-HLA scores from the expanded set must bind to MHC molecules at 50 nM or stronger). The vaccine that results from this application of OptiVax is then used as the foundation for vaccine augmentation with less stringent criteria (e.g., seed peptide-HLA scores from the candidate set must bind to MHC molecules at 1000 nM or stronger, and peptide-HLA scores from the expanded set must bind to MHC molecules at 100 nM or stronger) to further improve the desired vaccine performance. Methods for vaccine augmentation are described in Liu et al. (2020b), incorporated by reference in its entirety herein. In some embodiments, multiple rounds of vaccine augmentation may be utilized. In some embodiments, the final augmented vaccine is the one selected.

In some embodiments, selection of peptide sets to meet a desired predicted vaccine performance can be accomplished by computational algorithms other than OptiVax. In some embodiments, integer linear programming or mixed-integer linear programming is employed for selecting peptide sets instead of OptiVax. One example of an integer programming method for peptide set selection is described by Toussaint et al., 2008, incorporated by reference in its entirety herein. An example solver for mixed-integer linear programming is Python-MIP than can be used in conjunction with Toussaint et al., 2008. A second example of methods for vaccine peptide selection is described in "Maximum n-times Coverage for Vaccine Design" by Liu et al., 2021, incorporated by reference in its entirety herein.

Predicted vaccine performance refers to a metric. Predicted vaccine performance can be expressed as a single numerical value, a plurality of numerical values, any number of non-numerical values, and a combination thereof. The value or values can be expressed in any mathematical or symbolic term and on any scale (e.g., nominal scale, ordinal scale, interval scale, or ratio scale).

A seed (or base) peptide and all of the modified peptides that are derived from that seed (or base) peptide comprise a single peptide family. In some embodiments, in the component of vaccine performance that is based on peptide-HLA immunogenicity for a given HLA allele, a maximum number of peptides (e.g., 1, 2, 3, 4, 5, 6, 7, 8, or more) that are in the same peptide family are given computational immunogenicity credit for that HLA allele. This limit on peptide family immunogenicity limits the credit caused by many modified versions of the same base peptide. In some embodiments, the methods described herein are included for running OptiVax with an EvalVax objective function that corresponds to a desired metric of predicted vaccine performance. In some embodiments, population coverage means the proportion of a subject population that presents one or more immunogenic peptides that activate T cells responsive to a seed (or base) target peptide. The metric of population coverage is computed using the HLA haplotype frequency in a given population such as a representative human population. In some embodiments, the metric of population coverage is computed using marginal HLA frequencies in a population. Maximizing population coverage means selecting a peptide set (either a base peptide set, a modified peptide set, or a combination of base and modified peptides; e.g., a first peptide set, second peptide set, or third peptide set) that collectively results in the greatest fraction of the population that has at least a minimum number (e.g., 1, 2, 3, 4, 5, 6, 7, 8, or more) of immunogenic peptide-HLA bindings based on proportions of HLA haplotypes in a given population (e.g., representative human population). In some embodiments, this process includes the OptiVax selection of heteroclitic peptides (as described in this disclosure) that activate T cells that respond to their corresponding seed (or base) peptide and the heteroclitic base peptides to improve population coverage. In some embodiments, the seed (or base) target peptides are always included in the final vaccine design. In some embodiments, peptides are only considered as candidates for a vaccine design (e.g., included in a first, second, and/or third peptide set) if they have been observed to be immunogenic in clinical data, animal models, or tissue culture models.

Although heteroclitic peptides are used as exemplary embodiments in this disclosure, any modified peptide could be used in place of a heteroclitic peptide. A modified peptide is a peptide that has one or more amino acid substitutions of a target base/seed peptide. The amino acid substitution could be located at an anchor position or any other non-anchor position.

In some embodiments, a candidate vaccine peptide (e.g., a base peptide or a modified peptide) is eliminated from vaccine inclusion if it activates T cells that recognize self-peptides (e.g., this can be achieved at the first and/or second round of Peptide Filtering and Sorting as shown in FIGS. 1-2). In some embodiments, a candidate vaccine peptide (e.g., a base peptide or a modified peptide) is computationally eliminated from vaccine inclusion if its outward facing amino acids when bound by an HLA allele are similar to outward facing self-peptide residues that are presented by the same HLA allele, where similarity can be defined by identity or defined similarity metrics such as BLOSUM matrices (BLOSUM matrices are known in the art). Testing a vaccine peptide for its ability to activate T cells that recognize self-peptides can be experimentally accomplished by the vaccination of animal models followed by ELISPOT or other immunogenicity assay or with human tissue protocols. In both cases, models with HLA alleles that present the vaccine peptide are used. In some embodiments, human primary blood mononuclear cells (PBMCs) are stimulated with a vaccine peptide, the T cells are allowed to grow, and then T cell activation with a self-peptide is assayed as described in Tapia-Calle et al. (2019) or other methods as known in the art. In some embodiments, the vaccine peptide is excluded from vaccine inclusion if the T cells are activated by the self-peptide. In some embodiments, computational predictions of the ability of a peptide to activate T cells that also recognize self-peptides can be utilized. These predictions can be based upon the modeling of the outward facing residues from the peptide-HLA complex and their interactions with other peptide residues. In some embodiments, a candidate vaccine peptide (e.g., a base peptide or a modified peptide) is eliminated from vaccine inclusion or experimentally tested for cross-reactivity if it is predicted to activate T cells that also recognize self-peptides based upon the structural similarity of the peptide-MHC complex of the candidate peptide (e.g., a base peptide or a modified peptide) and the peptide-MHC complex of a self-peptide. One method for the prediction of peptide-MHC structure is described by Park et al. (2013).

In some embodiments, the peptide-HLA binding score or peptide-HLA immunogenicity metric for a candidate heteroclitic vaccine peptide (e.g., a modified peptide) and HLA allele is eliminated from consideration during vaccine design if the candidate heteroclitic vaccine peptide does not activate T cells that recognize its corresponding base/seed target peptide (second round of Peptide Scoring and Score Filtering, FIGS. 1-2) for the given HLA allele. In some embodiments, a heteroclitic vaccine peptide (e.g., a modified peptide) is eliminated from a vaccine design if the candidate heteroclitic vaccine peptide does not activate T cells that recognize its corresponding base/seed target peptide (second round of Peptide Scoring and Score Filtering, FIGS. 1-2) for a given HLA allele. Testing a candidate heteroclitic peptide (e.g., a modified peptide) for its ability to activate T cells that recognize its corresponding seed (or base) target peptide with respect to the same HLA allele can be experimentally accomplished by the vaccination of animal models followed by ELISPOT or other immunogenicity assay or with human tissue protocols. In both cases, models with HLA alleles that present the heteroclitic peptide are used. In some embodiments, human PBMCs are stimulated with the heteroclitic peptide, the T cells are allowed to grow, and then T cell activation with the seed (or base) target peptide is assayed as described in Tapia-Calle et al. (2019) or using other methods known in the art. In some embodiments, computational predictions of the ability of a heteroclitic peptide to activate T cells that also recognize the corresponding seed (or base) target peptide can be utilized. These predictions can be based upon the modeling of the outward facing residues from the peptide-HLA complex and their interactions with other peptide residues. In some embodiments, the structural similarity of the peptide-HLA complex of a heteroclitic peptide and the peptide-HLA complex of the corresponding seed (or base) target is used to qualify heteroclitic peptides for vaccine inclusion or to require experimental immunogenicity testing before vaccine inclusion.

TCR Interface Divergence (TCRID) is the Least Root Mean Square Deviation of the difference between a first peptide's TCR facing residues' 3D positions and the corresponding residue positions of a second peptide with respect to a specific HLA allele. In some embodiments, other metrics are used for the TCRID instead of Least Root Mean Square Deviation. In some embodiments, other metrics are used for the TCRID that include position deviations in non-TCR facing residues and MEW residues from the specific HLA allele. In some embodiments, TCRID is used to predict if two peptides when displayed by a given HLA allele will activate the same T cell clonotypes. In some embodiments, FlexPepDock (London et al., 2011, incorporated by reference in its entirety herein) or DINC (Antunes et al., 2018, incorporated by reference in its entirety herein) in conjunction with the crystal structures of HLA molecules can be used to compute TCRID metrics for pairs of peptides given an HLA molecule. In some embodiments, TCRID is computed by (1) determining the 3D peptide-HLA structures for two different peptides bound by a specific HLA allele, (2) aligning the HLA alpha helices of the peptide-HLA structures, and (3) computing the Least Root Mean Square Deviation of the difference between the TCR facing residues of the two peptides with respect to the aligned alpha helix reference frame.

In some embodiments, the second Peptide Scoring and Score Filtering step in FIGS. 1 and 2 will eliminate the peptide-HLA binding or immunogenicity score for a heteroclitic peptide for a specific HLA allele when the HLA specific TCRID between the heteroclitic peptide and its corresponding base (or seed) peptide from which it was derived is over a first TCRID threshold. In some embodiments, the second Peptide Scoring and Score Filtering step in FIGS. 1 and 2 will eliminate all peptide-HLA binding or immunogenicity scores for a heteroclitic peptide when a HLA specific TCRID between the heteroclitic peptide and its corresponding unmutated self-peptide from which it was derived is under a second TCRID threshold. In some embodiments, the first Peptide Scoring and Score Filtering step in FIGS. 1 and 2 will eliminate all peptide-HLA binding or immunogenicity scores for a candidate peptide when the HLA specific TCRID between the peptide and its corresponding unmutated self-peptide is under a third TCRID threshold. In some embodiments, any of the TCRID thresholds are determined by experimentally observing or computationally predicting the cross-reactivity of TCR molecules to peptide-HLA complexes.

Figure 3:
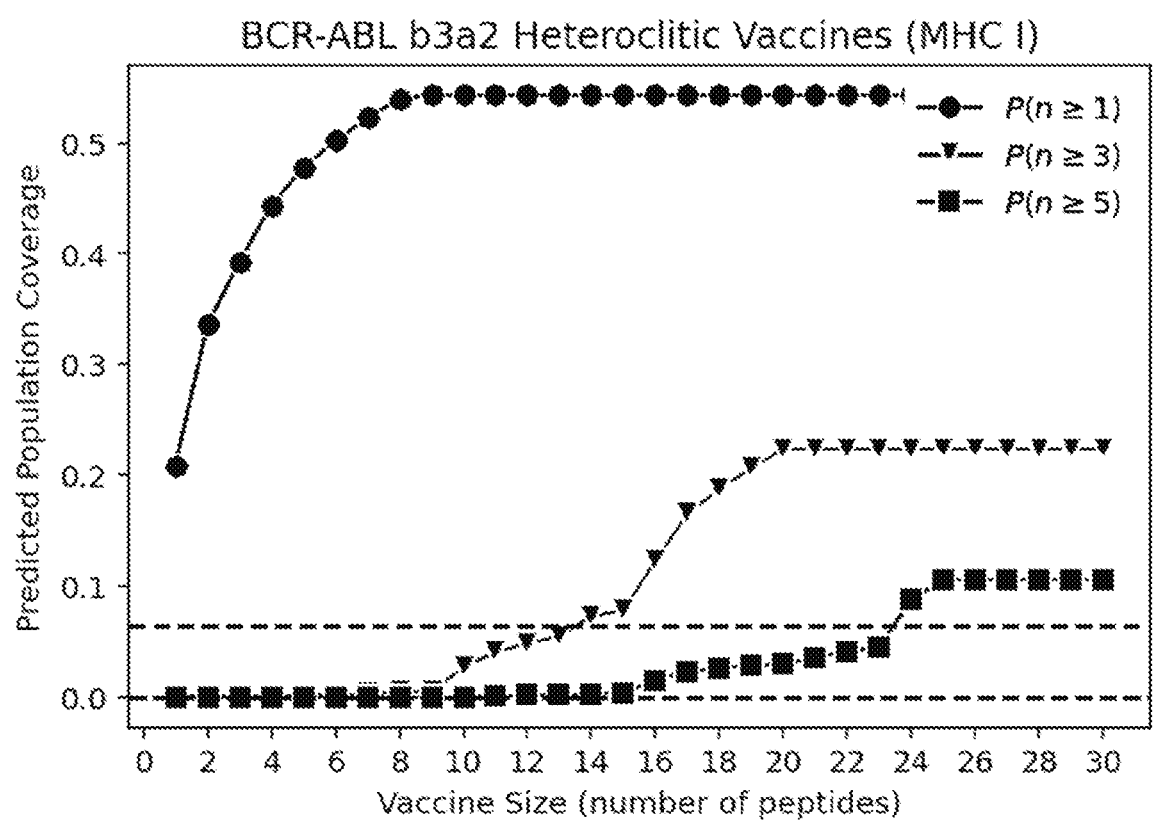
FIG. 3 is a graph showing predicted population coverage for MHC class I vaccines that include heteroclitic peptides by vaccine size for the BCR-ABL b3a2 fusion, for at least one peptide-HLA hit (circles), at least three peptide-HLA hits (triangles), and at least five peptide-HLA hits (squares). The dashed lines show the predicted population coverage of BCR-ABL b3a2 fusion vaccines without heteroclitic peptides for at least 1 (top dashed line) and 5 (bottom dashed line) peptide-HLA hits per-individual.
Figure 4:
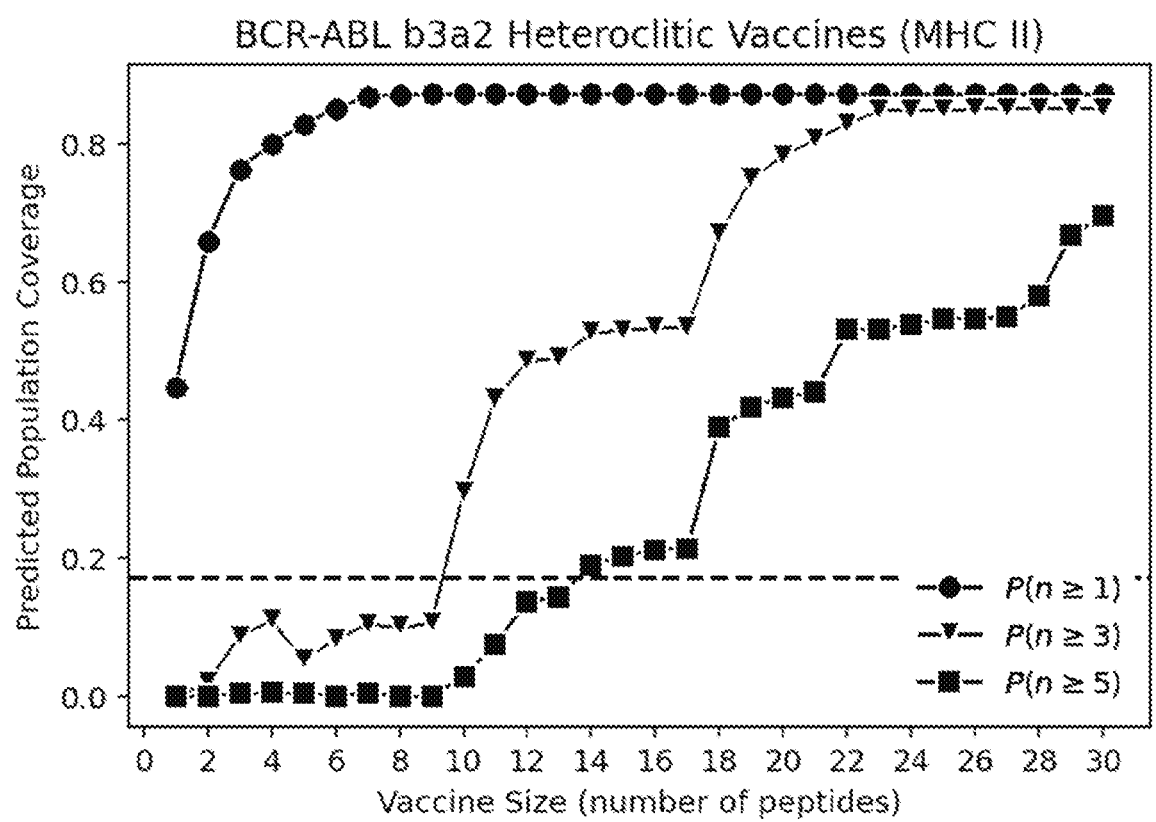
FIG. 4 is a graph showing predicted population coverage for MHC class II vaccines that include heteroclitic peptides by vaccine size for the BCR-ABL b3a2 fusion, for at least one peptide-HLA hit (circles), at least three peptide-HLA hits (triangles), and at least five peptide-HLA hits (squares). The dashed line shows the predicted population coverage of BCR-ABL b3a2 fusion vaccines without heteroclitic peptides for at least one peptide-HLA hit per-individual.
Figure 5:
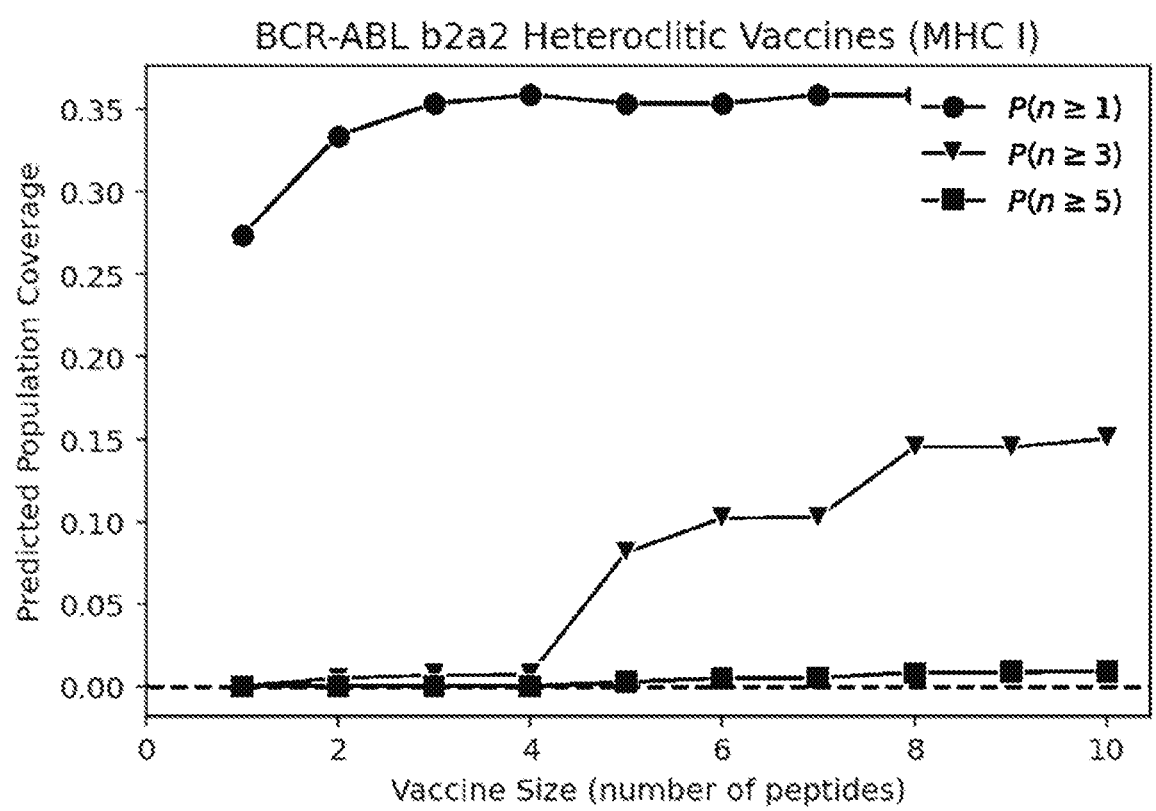
FIG. 5 is a graph showing predicted population coverage for MHC class I vaccines that include heteroclitic peptides by vaccine size for the BCR-ABL b2a2 fusion, for at least one peptide-HLA hit (circles), at least three peptide-HLA hits (triangles), and at least five peptide-HLA hits (squares). The dashed line shows the predicted population coverage of BCR-ABL b3a2 fusion vaccines without heteroclitic peptides for at least one peptide-HLA hit per-individual.
Figure 6:
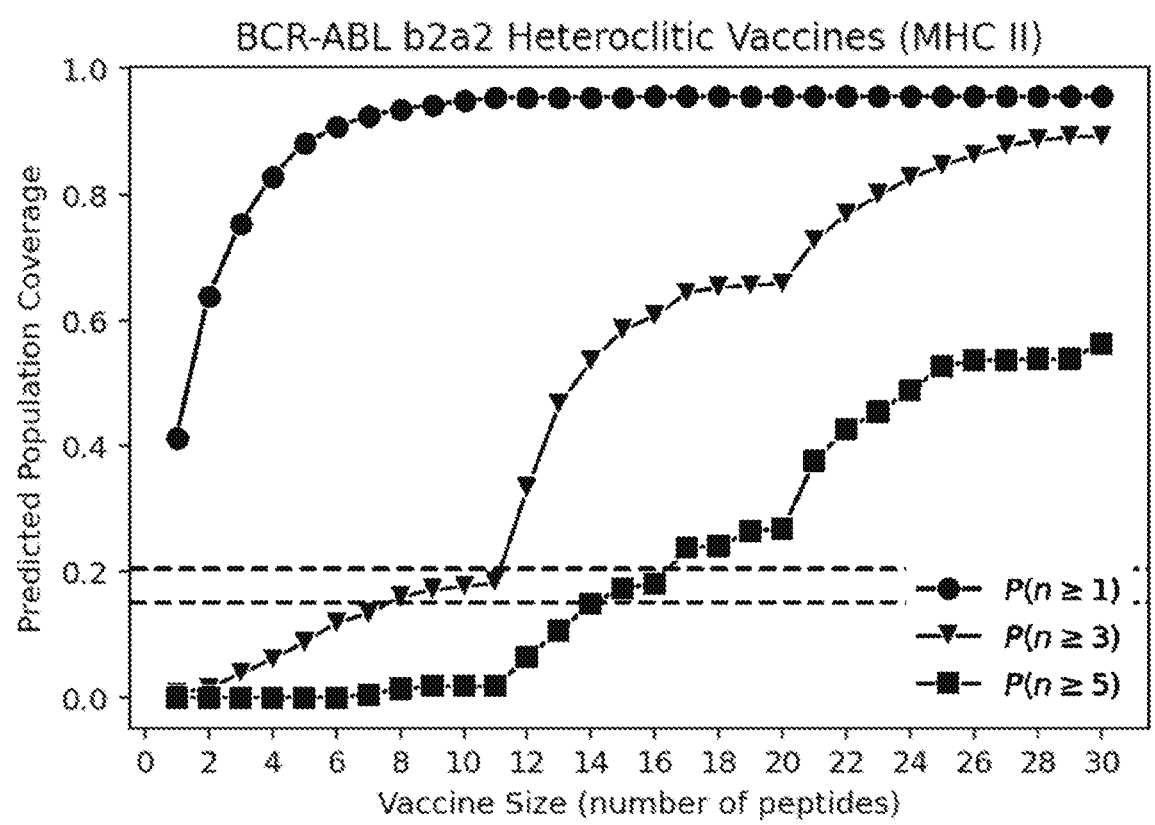
FIG. 6 is a graph showing predicted population coverage for MHC class II vaccines that include heteroclitic peptides by vaccine size for the BCR-ABL b2a2 fusion, for at least one peptide-HLA hit (circles), at least three peptide-HLA hits (triangles), and at least five peptide-HLA hits (squares). The dashed lines show the predicted population coverage of BCR-ABL b3a2 fusion vaccines without heteroclitic peptides for at least 1 (top dashed line) and 5 (bottom dashed line) peptide-HLA hits per-individual.

FIG. 3 shows predicted population coverage for MHC class I vaccines by vaccine size for the BCL-ABL fusion that produces b3a2. FIG. 4 shows predicted population coverage for MEW class II vaccines by vaccine size for the BCL-ABL fusion that produces b3a2. FIG. 5 shows predicted population coverage for MHC class I vaccines by vaccine size for the BCL-ABL fusion that produces b2a2. FIG. 6 shows predicted population coverage for MEW class II vaccines by vaccine size for the BCL-ABL fusion that produces b2a2.

OptiVax can be used to design a vaccine to maximize the fraction/proportion of the population whose HLA molecules are predicted to bind to and display at least p peptides from the vaccine. In some embodiments, this prediction (e.g., scoring) includes experimental immunogenicity data to directly predict at least p peptides will be immunogenic. The number p is input to OptiVax, and OptiVax can be run multiple times with varying values for p to obtain a predicted optimal target peptide set for different peptide counts p.

Larger values of p will increase the redundancy of a vaccine at the cost of more peptides to achieve a desired population coverage. In some embodiments, it may not be possible to achieve a given population coverage given a specific heteroclitic base set. In some embodiments, the number p is a function of the desired size of a vaccine.

The methods described herein can be used to design separate vaccine formulations for MHC class I and class II-based immunity.

In some embodiments, this procedure is used to create a vaccine for an individual. In some embodiments, the target peptides present in the individual are determined by sequencing the individual's tumor RNA or DNA and identifying mutations that produce foreign peptides. One embodiment of this method is described in U.S. Pat. No. 10,738,355, incorporated in its entirety herein. In some embodiments, peptide sequencing methods are used to identify target peptides in the individual. One embodiment of this is described in U.S. Publication No. 2011/0257890. In some embodiments, the target peptides used for the individual's vaccine are selected when a self-peptide, foreign peptide, pathogen peptide or RNA encoding a self-peptide, foreign peptide or pathogen peptide is observed in a specimen from the individual is present at a predetermined level. The target peptides in the individual are used to construct a vaccine as disclosed herein. For vaccine design, OptiVax is provided a diplotype comprising the HLA type of the individual. In an alternative embodiment, the HLA type of an individual is separated into multiple diplotypes with frequencies that sum to one, where each diplotype comprises one or more HLA alleles from the individual and a notation that the other allele positions should not be evaluated. The use of multiple diplotypes will cause OptiVax's objective function to increase the chance that immunogenic peptides will be displayed by all of the constructed diplotypes. This achieves the objective of maximizing the number of distinct HLA alleles in the individual that exhibit peptide-HLA immunogenicity and thus improves the allelic coverage of the vaccine in the individual.

Figure 7:
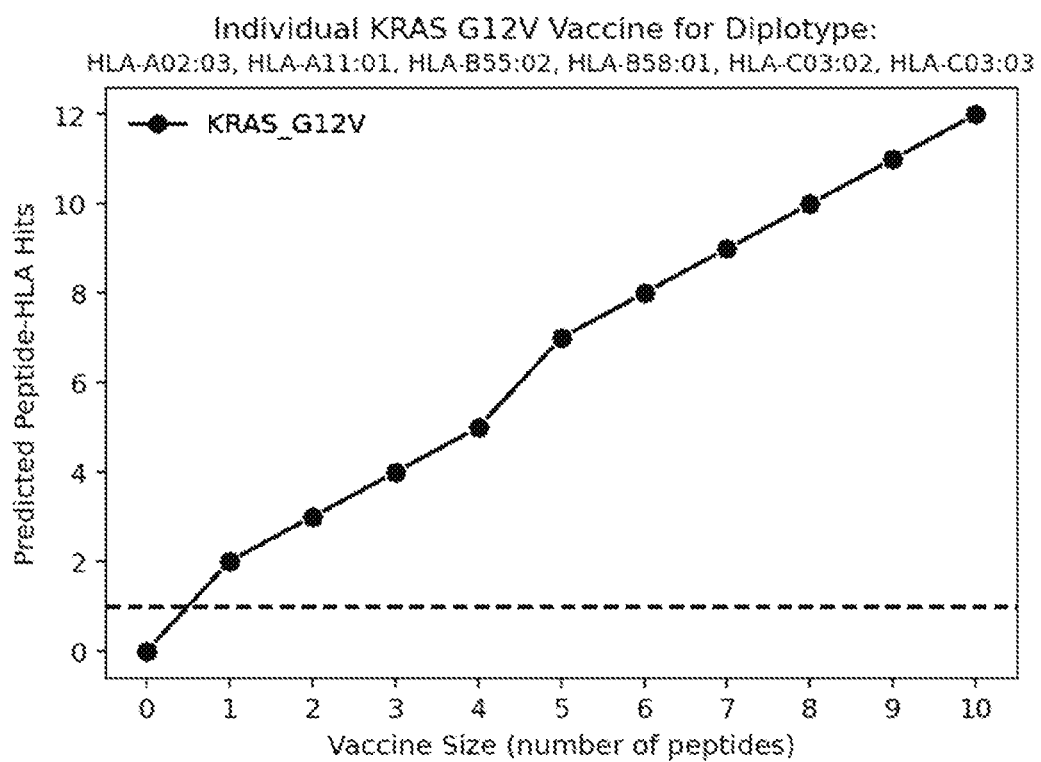
FIG. 7 is a graph showing predicted peptide-HLA hits by vaccine size for a KRAS G12V vaccine that includes heteroclitic peptides for the HLA diplotype HLA-A02:03, HLA-A11:01, HLA-B55:02, HLA-B58:01, HLA-C03:02, and HLA-C03:03. The dashed line shows predicted peptide-HLA hits by vaccine size for a KRAS G12V vaccine without heteroclitic peptides.

FIG. 7 shows the predicted vaccine performance (predicted number of peptide-HLA hits) of ten example G12V MHC class I vaccines for a single individual with the MHC class I HLA diplotype HLA-A02:03, HLA-A11:01, HLA-B55:02, HLA-B58:01, HLA-C03:02, and HLA-C03:03. OptiVax was used to design ten G12V MHC class I vaccines for this HLA diplotype with peptide counts ranging from 1 to 10. For the results in FIG. 7, OptiVax was run with six synthetic diplotypes, each equally weighted, each with one HLA allele from the individual's HLA diplotype, and the other allele positions marked to not be evaluated.

MHC Class I Vaccine Design Procedure

In some embodiments, MHC class I vaccine design procedures consist of the following computational steps.

In some embodiments, the inputs for the computation are:
Peptide sequence (length n) containing the neoantigen or pathogenic target(s) of interest (e.g., KRAS G12D, KRAS G12V, KRAS G12R, KRAS G12C, KRAS G13D, BCR-ABL b3a2, BCR-ABL b2a2). $P_i$ denotes the amino acid at position i.
t; Position of target mutation in P, $t \in [1, \ldots n]$ (e.g., t=12 for KRAS G12D).
s: Substitution mutations E [true, false] is true if the mutation is a substitution, and false if the mutation is a deletion or insertion or the peptide does not contain a mutation (such as in pathogen targets). When the mutation is a deletion or insertion then t indicates the position immediately before the deletion or insertion.

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\vec{\mathcal{H}}$ : Set of HLA alleles (for HLA-A, HLA-B, HLA-C loci)

F: $\vec{\mathcal{H}}^3 \to \mathbb{R}$ : Population haplotype frequencies (for OptiVax optimization and coverage evaluation).

N; Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \vec{\mathcal{H}} \to \mathbb{R}$ : Scoring function mapping a (peptide, HLA allele) pair to a prediction of peptide-HLA display. If predicted affinity$\leq \tau_1$, then returns 1, else returns 0. Options include MHCflurry, NetMHCpan, PUFFIN, ensembles, or alternative metrics or software may be used, including models calibrated against immunogenicity data.

ScoreDisplay: $P \times \vec{\mathcal{H}} \to \mathbb{R}$ : Scoring function mapping a (peptide, HLA allele) pair to a prediction of peptide-HLA display. If predicted affinity$\leq$r', then returns 1, else returns 0. Options include MHCflurry, NetMHCpan, PUFFIN, ensembles, or alternative metrics or software may be used, including models calibrated against immunogenicity data.

Next, from the seed protein sequence (P), a set $\mathcal{P}$ of windowed native peptides spanning the protein sequence(s) is constructed. $P_{j \ldots j+(k-1)}$ only produces set members when the subscripts are within the range of the defined seed protein P. In some embodiments, 8-mers, 9-mers, 10-mers, and 11-mers are produced, but this process can be performed with any desired window lengths and the resulting peptide sets combined. In some embodiments, only 9-mers are produced.

$$\mathcal{P} = \bigcup_{k \in [8, \ldots, 11]} \mathcal{P}_k$$

$$\mathcal{P}_k = \{P_{j \ldots j+(k-1)} \mid j \in [t-(k-1), \ldots, t],$$

$$\text{if } s \text{ then } j \neq \{t-(k-1), t-1\}\}$$

The second condition $j \neq \{t-(k-1), t-1\}$ excludes peptides where the mutation at t is in positions P2 or Pk of the windowed k-mer peptide (i.e., the anchor positions) and the mutation is a substitution.

MHC Class I Vaccine Design Procedure with Defined Peptide Set $\mathcal{P}$

Next, each peptide sequence in $\mathcal{P}$ is scored against all HLA alleles in $\vec{\mathcal{H}}$ for potential presentation using SCOREPOTENTIAL (with threshold $\tau_1$=500 nM) and store results in a $|\mathcal{P}| \times |\vec{\mathcal{H}}|$ matrix S:

$$S[p,h] = \text{ScorePotential}(p,h) \forall p \in \mathcal{P}, h \in \vec{\mathcal{H}}$$

Note that S is a binary matrix where 1 indicates the HLA is predicted to potentially present the peptide, and 0 indicates no potential presentation.

Define Base Set of Peptides B⊆$\mathcal{P}$:

$$B=\{p\in \mathcal{P} \mid \exists h \ s.t. S[p,h]=1\}$$

Thus, B contains the native peptides that are predicted to be potentially presented by at least 1 HLA.

Create a Set of all Heteroclitic Peptides B' Stemming from Peptides in B:

$$B' = \bigcup_{b\in B} A_{NCHOR} - M_{ODIFIED}(b)$$

where ANCHOR-MODIFIED(b) returns a set of all 399 anchor-modified peptides stemming from b (with all possible modifications to the amino acids at P2 and P9).

Next, all heteroclitic candidate peptides (e.g., modified peptides) in B' are scored against all HLA alleles in $\vec{\mathcal{H}}$ for predicted display using SCOREDISPLAY (with threshold $\tau_2$=50 nM), and store results in binary $|B'|\times|\vec{\mathcal{H}}|$ matrix $S'_1$:

$$S'_1[b',h]=\text{SCOREDISPLAY}(b',h) \forall b' \in B', h \in \vec{\mathcal{H}}$$

Next, an updated scoring matrix $S'_2$ is computed for heteroclitic peptides conditioned on the potential presentation of the corresponding base peptides by each HLA:

$$S'_2[b', h] = \begin{cases} S'_1[b', h], & \text{if } S[b, h] = 1 \\ 0, & \text{otherwise} \end{cases} \forall b' \in B', h \in \mathcal{H}$$

where each heteroclitic peptide b'∈B' is a mutation of base peptide b∈B. This condition enforces that if h was not predicted to potentially present b, then all heteroclitic peptides b' derived from b will not be displayed by h (even if h would otherwise be predicted to display b').

In some embodiments, OptiVax-Robust is used to design a final peptide set (e.g., third peptide set) from the union of base peptides and heteroclitic peptides B U B' (with corresponding scoring matrices S and $S'_2$ for B and B', respectively). OptiVax will output m sets $\mathcal{V}_s$ for s∈[1, . . . , m] where m is the largest vaccine size requested from OptiVax. Let $\mathcal{V}_k$ denote the compact set of vaccine peptides output by OptiVax containing k peptides. Note that $\mathcal{V}_{k+1}$ is not necessarily a superset of $\mathcal{V}_k$. In alternate embodiments, OptiVax can be used to augment the base set B with peptides from B' using scoring matrix $S'_2$ to have OptiVax return set $\mathcal{A}_k$, and the final vaccine set $\mathcal{V}_{k+|B|}$ consists of peptides B∪$\mathcal{A}_k$.

In some embodiments, this procedure is repeated independently for each target of interest, and the resulting independent vaccine sets can be merged into a combined vaccine as described below.

WIC Class II Vaccine Design Procedure

In some embodiments, WIC class II vaccine design procedures consist of the following computational steps.

In some embodiments, the inputs for the computation are:

$P_{1 \ldots n}$: Peptide sequence(s) (length n) containing the neoantigen(s) of interest (e.g., KRAS G12D, KRAS G12V, KRAS G12R, KRAS G12C, KRAS G13D, BCR-ABL b3a2, BCR-ABL b2a2). $P_i$ denotes the amino acid at position i.

t: Position of target mutation in P, t∈[1, . . . ,n] (e.g., t=12 for KRAS G12D).

s: Substitution mutations ∈[true, false] is true if the mutation is a substitution, and false if the mutation is a deletion or insertion or the peptide does not contain a mutation (such as for pathogen targets). When the mutation is a deletion or insertion then t indicates the position immediately before the deletion or insertion.

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\vec{\mathcal{H}}$ : Set of HLA alleles (for HLA-DR, HLA-DQ, HLA-DP loci)

F: $\vec{\mathcal{H}}^3 \to \mathbb{R}$ : Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes P(n≥1) population coverage).

In some embodiments, Peptide-HLA Scoring Functions used are:

SCOREPOTENTIAL: P×$\vec{\mathcal{H}} \to \mathbb{R}$ : Scoring function mapping a (peptide, HLA allele) pair to a prediction of display. If predicted affinity ≤$\tau_1$, then returns 1, else returns 0. Options include NetMHCIIpan, PUFFIN, ensembles, or alternative metrics or software may be used, including models calibrated against immunogenicity data.

SCOREDISPLAY: P×$\vec{\mathcal{H}} \to \mathbb{R}$ : Scoring function mapping a (peptide, HLA allele) pair to a prediction of peptide-HLA display. If predicted affinity≤$\tau_1$, then returns 1, else returns 0. Options include NetMHCIIpan, PUFFIN, ensembles, or alternative metrics or software may be used, including models calibrated against immunogenicity data.

FindCore: P×$\vec{\mathcal{H}} \to$[1, . . . ,n]; Function mapping a (peptide, HLA allele) pair to a prediction of the 9-mer binding core. The core may be specified as the offset position (index) into the peptide where the core begins.

Next, from the seed protein sequence (P), a set $\mathcal{P}$ of peptides spanning the protein sequence are constructed. $P_{j \ldots j+(k-1)}$ only produces set members when the subscripts are within the range of the defined seed protein P. Here, we extract all windowed peptides of length 13-25 spanning the target mutation, but this process can be performed using any desired window lengths (e.g., only 15-mers).

$$\mathcal{P} = \bigcup_{k\in[13,\ldots,25]} \mathcal{P}_k$$

$$\mathcal{P}_k = \{P_{j\ldots j+(k-1)} \mid j \in [t-(k-1), \ldots, t]\}$$

where $\mathcal{P}_k$ contains all sliding windows of length k, which are combined to form $\mathcal{P}$. Note that here (unlike MHC class I), no peptides are excluded based on binding core or anchor residue positions (for MHC class II, filtering is performed as described in this disclosure).

MHC Class II Vaccine Design Procedure with Defined Peptide Set $\mathcal{P}$

Next, each peptide sequence in $\mathcal{P}$ is scored against all HLA alleles in $\vec{\mathcal{H}}$ for potential presentation using SCOREPOTENTIAL (with threshold $\tau_1$=500 nM) and store results in $|\mathcal{P}|\times|\vec{\mathcal{H}}|$ matrix $S_1$:

$$S_1[p,h]=\text{SCOREPOTENTIAL}(p,h) \forall p\in \mathcal{P}, h\in \vec{\mathcal{H}}$$

Note that $S_1$ is a binary matrix where 1 indicates the HLA is predicted to potentially present the peptide, and 0 indicates no potential presentation.

For each (peptide, HLA allele) pair (p, h), identify/predict the 9-mer binding core using FINDCORE. The predicted binding core is recorded in a matrix C:

$$C[p,h] = \text{FindCore}(p,h) \forall p \in \mathcal{P}, h \in \vec{\mathcal{H}}$$

Next, if not(s) then $S_2[p, h] = S_1[p, h]$ otherwise an updated scoring matrix $S_2$ is computed for native peptides in P:

$$S_2[p, h] = \begin{cases} S_1[p, h], & \text{if } C[p, h] \text{ specifies } P_t \text{ at a non-anchor position inside core} \\ 0, & \text{otherwise} \end{cases}$$

$$\forall p \in \mathcal{P}, h \in \mathcal{H}.$$

where $P_t$ is the target residue of interest (e.g., the mutation site of KRAS G12D). This condition enforces the target residue to fall within the binding core at a non-anchor position for all (peptide, HLA allele) pairs with non-zero scores in $S_2$, and allows the binding core to vary by allele per peptide (as the binding cores of a particular peptide may differ based on the HLA allele presenting the peptide). Thus, for each pair (p, h), if the predicted binding core C[p, h] specifies the target residue $P_t$ at an anchor position (P1, P4, P6, or P9 of the 9-mer core), or if $P_t$ is not contained within the binding core, then $S_2$ [p, h]=0. In an alternate embodiment, $P_t$ can be located outside of the core or inside the core in a non-anchor position. In some embodiments, $P_t$ can only be located at specific positions inside and/or outside of the core. In some embodiments, the binding core predictions in C are accompanied by prediction confidences. In some embodiments, if the confidence for predicted core C[p, h] is below a desired threshold (e.g., 0.5, 0.6, 0.7, 0.8, or 0.9), then $S_2$ [p, h]=0.

Next, OptiVax-Robust is run with peptides $\mathcal{P}$ and scoring matrix $S_2$ to identify a non-redundant base set of peptides $B \subseteq \mathcal{P}$. (In alternate embodiments, B can be chosen as the entire set $\mathcal{P}$ rather than identifying a non-redundant base set.)

Next, a set of all heteroclitic peptides B' is created stemming from peptides in B:

$$B' = \bigcup_{b \in B} \{A_{NCHOR} - M_{ODIFIED}(b, c) \forall c \mid \exists h \text{ s.t. } S_2[b, h] = 1\}$$

where ANCHOR-MODIFIED(b,c) returns a set of all $20^4$-1 anchor-modified peptides stemming from b with all possible modifications to the amino acids at P1, P4, P6, and P9 of the 9-mer binding core c. Thus, for each base peptide b, the heteroclitic set B' contains all anchor-modified peptides b' with modifications to all unique cores of b identified for any HLA alleles that potentially present b with a valid core position as indicated by scoring matrix $S_2$.

Next, all heteroclitic candidate peptides (e.g., modified peptides) in B' are scored against all HLA alleles in $\vec{\mathcal{H}}$ for predicted display using SCOREDISPLAY (with threshold $\tau_2$=50 nM), and store results in binary $|B'| \times \vec{\mathcal{H}}|$ matrix $S'_1$:

$$S'_1[b',h] = \text{ScoreDisplay}(b',h) \forall b' \in B', h \in \vec{\mathcal{H}}$$

For each (heteroclitic peptide, HLA allele) pair (b',h), identify/predict the 9-mer binding core using FINDCORE. The predicted binding core is recorded in a matrix C':

$$C'[b',h] = \text{FindCore}(b',h) \forall b' \in B', h \in \vec{\mathcal{H}}$$

An updated scoring matrix $S'_2$ is computed for heteroclitic peptides conditioned on the identified binding cores of a heteroclitic and base peptides occurring at the same offset by a particular HLA:

$$S'_2[b', h] = \begin{cases} S'_1[b', h], & \text{if } C'[b', h] = C[b, h] \\ 0, & \text{otherwise} \end{cases} \forall b' \in B', h \in \mathcal{H}$$

where each heteroclitic peptide b'∈ B' is a mutation of base peptide b∈ B. This condition enforces the binding core of the heteroclitic peptide b' to be at the same relative position as the base peptide b, and, implicitly, enforces that the target residue $P_t$ still falls in a non-anchor position within the 9-mer binding core (Step 3).

An updated scoring matrix $S'_3$ is computed for heteroclitic peptides conditioned on the potential presentation of the corresponding base peptides by each HLA:

$$S'_3[b', h] = \begin{cases} S'_2[b', h], & \text{if } S[b, h] = 1 \\ 0, & \text{otherwise} \end{cases} \forall b' \in B', h \in \mathcal{H}$$

where each heteroclitic peptide b'∈ B' is a mutation of base peptide b∈ B. This condition enforces that if h was not predicted to display b, then all heteroclitic peptides b' derived from b will not be displayed by h (even if h would otherwise be predicted to display b').

OptiVax-Robust is used to design a final peptide set (e.g., third peptide set) from the union of base peptides and heteroclitic peptides B∪B' (with corresponding scoring matrices $S_2$ and $S'_3$ for B and B', respectively). OptiVax will output m sets $\mathcal{V}_s$ for s∈[1, . . . , m] where m is the largest vaccine size requested from OptiVax. Let $\mathcal{V}_k$ denote the compact set of vaccine peptides output by OptiVax containing k peptides. Note that $\mathcal{V}_{k+1}$ is not necessarily a superset of $\mathcal{V}_k$. In alternate embodiments, OptiVax can be used to augment the base set B with peptides from B' using scoring matrix $S'_2$ to have OptiVax return set $\mathcal{A}_k$, and the final vaccine set $\mathcal{V}_{k+|B|}$ consists of peptides B∪$\mathcal{A}_k$.

In some embodiments, this procedure is repeated independently for each single target of interest, and the resulting independent vaccine sets can be merged into a combined vaccine as described below.

MEW Class I or Class II Vaccine Design Method Prioritizing Peptide Conservation

In some embodiments, peptide sequences that are more conserved across strains, species, or other protein sources of interest are prioritized for vaccine inclusion. In some embodiments, a set of related protein sequences called protein variants are considered for vaccine design. A protein variant is one instance of a family of protein sequences, and protein variants can be sequences from various species, pathogen strains, viral strains, or other variations considered for vaccine design. In some embodiments, each protein variant has an associated probability called a protein variant probability, where the sum of all protein variant probabilities for the supplied set of protein variants is one. In some embodiments, multiple proteins of interest can be considered for the design of a single vaccine using an MEW Class I or Class II vaccine design method prioritizing peptide conservation. In these embodiments, protein variants for all proteins of interest are collectively considered for generating candidate peptides. In some embodiments, the protein variant probabilities across all of the considered multiple proteins sum to one.

A set of candidate peptides are created from each protein variant using a sliding window method that parses the protein variant into peptide sequences. In some embodiments, for MEW Class I 8-mers, 9-mers, 10-mers, and/or 11-mers are produced, but this process can be performed with any desired window lengths and the resulting peptide sets combined. In some embodiments, for MEW Class I, only 9-mers are produced. In some embodiments, for MEW Class II, all windowed peptides of length 13-25 are produced, but this process can be performed using any desired window lengths (e.g., only 15-mers). In some embodiments, peptides that are predicted to be glycosylated in a given protein variant are removed and not considered for that variant as described in Liu et al. 2020 which is incorporated by reference herein in its entirety.

In some embodiments, for each generated peptide sequence (MHC Class I or Class II) conservation is defined as the fraction of input protein variants where the peptide sequence occurs. For example, if a given 9-mer peptide sequence occurs in the peptides generated from 90% of the protein variants provided as input, its conservation is 0.90. In some embodiments, conservation is defined for each generated peptide sequence (MHC Class I or Class II) as the sum of the protein variant frequencies where the peptide sequence occurs. For example, if a given 9-mer peptide sequence occurs in the peptides generated from protein variants with protein variant probabilities of 0.10 and 0.20, its conservation is 0.30. In some embodiments, this functionality is implemented by a ComputeConservation function that computes the sum of the frequencies of the protein variants that contain a peptide sequence. In some embodiments, when sufficient protein variants are not sufficient for computing expected future conservation a method of predicting conservation can be used to implement ComputeConservation, such as the one found in Hie et al., 2021 which is incorporated by reference herein in its entirety.

In some embodiments, vaccine design considers conservation by prioritizing peptides for vaccine inclusion that are more conserved than others to meet a desired vaccine performance metric. In some embodiments, the vaccine design method attempts to first design a vaccine with candidate peptides that all meet a first conservation threshold, and if the desired vaccine performance is not met, it iteratively adds additional peptides with less stringent conservation to attempt to meet the desired vaccine performance metric. In some embodiments, vaccine design prioritizing conservation proceeds by setting a vaccine design D to be an empty set, and then performing the steps of: (1) selecting candidate peptides in which each peptide passes a conservation threshold to create a candidate peptide set and is not in D, (2) selecting vaccine designs having varying peptide numbers/combinations from this candidate set to optimize a vaccine performance metric using methods disclosed herein for MHC Class I or Class II vaccine design to augment the vaccine design contained in D (one implementation of vaccine augmentation is described in (Liu et al., 2021), incorporated by reference in its entirety herein), (3) selecting the smallest vaccine peptide set design from Step 2 that either meets the desired vaccine performance metric or where adding one more peptide to the selected set does not provide a desired minimum improvement in the vaccine performance metric, (4) if a vaccine peptide set was found in Step 3, adding the vaccine peptide set design from Step 3 to the vaccine design D, and (5) determining whether the vaccine design D meets a desired vaccine performance metric objective, and if so, return vaccine design D as the final vaccine design. If at Step 6, the vaccine design D fails to meet the desired vaccine performance metric objective, the computation continues with the following steps: (6) setting an updated conservation threshold to be lower than the current conservation threshold (less constrained) and (7) repeating the process starting at Step 1 retaining the current vaccine design D and current candidate set until either a desired vaccine performance metric objective is reached at Step 6, or the updated conservation threshold is lower than a minimum desired conservation threshold. If on any iteration, the updated conservation threshold is lower than a minimum desired conservation threshold, the latest version of vaccine design D will be used as the final vaccine design. When the process completes, the final vaccine design D includes all of the peptides that can be used in a vaccine.

In some embodiments, MEW class I or class II vaccine design procedures consist of the following computational steps.

In some embodiments, the inputs for the computation are:

$P_{j,1 \ldots n_j}$: Peptide sequence of protein variant j of length $n_j$. $P_{j,i}$ denotes the amino acid at position i of protein variant j; where $j \in [1, \ldots \alpha]$ and a is the number of protein variants $O_j$: Protein variant probability of protein variant $P_j$ $t_j$: Position in protein variant $P_j$ of the target mutation $t \in [1 \ldots n]$ D: The vaccine design, initialized to the empty set $\emptyset$ s: Substitution mutations $s \in [\text{true, false}]$ is true if the mutation is a substitution, and false if the mutation is a deletion or insertion or the peptide does not contain a mutation. When the mutation is a deletion or insertion then t indicates the position immediately before the deletion or insertion.

$c_1$: Initial conservation level of peptides $c_c$: Current conservation threshold $c_2$: Change in conservation level on each iteration $c_m$: Minimum final conservation v: Target vaccine performance metric $v_d$: Minimum change in vaccine performance metric to increase vaccine size N: Parameter for EvalVax and OptiVax objective function. Specifies minimum number of predicted per-individual hits for population coverage objective to consider the individual covered. Default=1 (computes $P(n \geq 1)$ population coverage).

COMPUTECONSERAVTION: $S \times X \times 0 \rightarrow \mathbb{R}$: In some embodiments, computes the fraction of sets $X_j$ that contain sequence S. In some embodiments, sums all the $O_j$ where sequence S appears in $X_j$ The protein variant sequences $P_i$ are used to produce windowed peptides that span the protein sequence(s) starting at each location m with a peptide length of k residues. The result is the set $X_j$ that contains all of the peptide sequences in protein variant $P_j$. $P_{j,m \ldots m+(k-1)}$ only produces a sequence when the subscripts are within the range of the defined protein $P_j$. In some embodiments for MEW Class I, k is chosen to produce 8-mers, 9-mers, 10-mers, and 11-mers, but this process can be performed with any desired window lengths and the resulting peptide sets combined. In some embodiments for MEW Class I, only 9-mers are produced. In some embodiments for MEW Class II, we extract all windowed peptides of length 13-25, but this process can be performed using any desired window lengths (e.g., only 15-mers).

$$X_j = \bigcup_{\substack{t \in [1 \ldots n_j] \\ k \in \left[\substack{8-11 MHC\ Class\ I \\ 13-25 MHC\ Class\ II}\right]}} \left\{ \begin{array}{l} P_{j,m \ldots m+(k-1)} \mid m \in [t-(k-1), \ldots, t], \\ \text{if } s \text{ and } MHC\ Class\ I \text{ then} \\ m \neq \{t-(k-1), t-1\} \end{array} \right\}$$

In some embodiments for MEW Class I, the second condition $m \neq \{t-(k-1), t-1\}$ excludes peptides where the mutation at t is in positions P2 or Pk of the windowed k-mer peptide (i.e., the anchor positions) and the mutation is a substitution and if for MHC Class I design. MHC Class II anchor positions are filtered in the MHC Class II design method.

Create the set of all peptides B that occur in any input protein variant.

$$B = \bigcup_{j \in [1, \ldots a]} X_j$$

$$z = |B|$$

For each peptide $B_w$ in B its conservation metric $C_w$ is computed using COMPUTECONSERVATION $$C_w = \text{ComputeConservation}[B_w, X, O]$$

The current conservation threshold is then set to the initial conservation threshold $$c_c = c_1$$

At Step 1, candidate peptides are selected where each peptide passes a conservation threshold to create a candidate peptide set and is not in D. A set of peptide candidates $\mathcal{P}$ is defined such that each candidate peptide meets the current conservation threshold $c_c$ and the peptide candidate is not already in D. D is set to empty (0 peptides) on the first iteration of the computational steps.

$$\mathcal{P} = U_{w \in [1, \ldots, z]} B_w \text{ where } C_w \geq c_c \text{ and } B_w \notin D$$

At Step 2, vaccine designs are selected having varying peptide numbers/combinations from the candidate set to optimize a vaccine performance metric using methods disclosed herein for MHC Class I or Class II vaccine design to augment the vaccine design contained in D. The peptide set $\mathcal{P}$ is provided to "MHC Class I Vaccine Design Procedure with Defined Peptide Set $\mathcal{P}$" for MHC Class I and "MHC Class II Vaccine Design Procedure with Defined Peptide Set $\mathcal{P}$" for MHC Class II. The peptide set $\mathcal{P}$ is provided as the set of candidates to augment the set D. Both the set $\mathcal{P}$ and D are provided to OptiVax which uses D as the fixed starting set and augments D with peptides from the set $\mathcal{P}$ using vaccine augmentation as described in (Liu et al., 2021), incorporated by reference in its entirety herein. OptiVax-Robust is used to augment the set D with peptides from $\mathcal{P}$ using the scoring matrices as defined in "MHC Class I Vaccine Design Procedure with Defined Peptide Set $\mathcal{P}$" for MHC Class I and "MHC Class II Vaccine Design Procedure with Defined Peptide Set $\mathcal{P}$" for MHC Class II, and returns sets $\mathcal{A}_s$ where each set $\mathcal{A}_s$ is a compact set of vaccine peptides output by OptiVax containing s peptides. In some embodiments, the steps to modify anchor positions are not utilized in the MHC Class I or MHC Class II vaccine design methods and only the base peptides B are utilized for vaccine design. In some embodiments, positions in addition to anchor positions are modified in the MHC Class I or MHC Class II vaccine design methods utilized to create B'.

At Step 3, the smallest vaccine peptide set design is selected from Step 2 that either meets the desired vaccine performance metric or where adding one more peptide to the selected set does not provide a desired minimum improvement in the vaccine performance metric. A vaccine design $\mathcal{A}_s$ is chosen that meets minimum requirements. In some embodiments, the vaccine design $\mathcal{A}_s$ is chosen with the value s chosen to be the minimum value of s such that the difference in vaccine performance between $D \cup \mathcal{A}_s$ and $D \cup \mathcal{A}_{s+1}$ is less than $v_d$. In some embodiments, the value s is chosen to be the minimum value such that the vaccine performance metric of $D \cup \mathcal{A}_s$ meets the final vaccine performance metric v. In some embodiments, $\mathcal{A}_{s+1}$ is not necessarily a superset of $\mathcal{A}_s$.

At Step 4, if a vaccine peptide set was found in Step 3, it is added to the vaccine peptide set design D. If an acceptable vaccine design $\mathcal{A}_s$ was found in Step 4, the vaccine design set D is updated to consist of $D \cup \mathcal{A}_s$.

At Step 5, it is determined whether the vaccine design D meets a desired vaccine performance metric objective. If the vaccine design set D meets the final vaccine performance design metric v, return D as the final design.

At Step 6, the conservation threshold is updated to be lower than the current conservation threshold (less constrained). If the vaccine design set D does not meet the final vaccine performance design metric v, reduce $c_c$ $$c_c = c_c - c_2$$

At Step 7, repeat the process starting at Step 1 retaining the current vaccine design D and current candidate set until either a desired vaccine performance metric objective is reached at Step 5, or the updated conservation threshold is lower than a minimum desired conservation threshold. If $c_c < c_m$ then return design set D as the final vaccine. If not, return to Step 1 and repeat all subsequent steps.

In some embodiments, this procedure is repeated independently for each single BCL-ABL gene fusion of interest, and the resulting independent vaccine sets can be merged into a combined vaccine.

Methods for Combining Multiple Vaccines

The above-described methods will produce an optimized target peptide set (e.g., third peptide set) for one or more individual targets. In some embodiments, a method is provided for designing separate vaccines for MEW class I and class II-based immunity for multiple targets (e.g., two or more targets such as KRAS G12D and KRAS G12V).

In some embodiments, a method is disclosed for producing a combined peptide vaccine for multiple targets by using a table of presentations for a disease that is based upon empirical data from sources such as the Cancer Genome Atlas (TCGA). FIG. 8 shows one embodiment for factoring disease presentation type probabilities (e.g., pancreatic cancer, colorectal cancer, and skin cancer) by probability, for each disease presentation, of target presented for various mutation targets (e.g., KRAS G12D, KRAS G12V, and KRAS G12R). A presentation is a unique set of targets that are presented by one form of a disease (e.g., distinct type of cancer or cancer indication as shown in FIG. 8). For each presentation, FIG. 8 shows an example of the probability of that presentation, and the probability that a given target is observed. For a given presentation, there can be one or more targets, each having a probability. In some embodiments, the method for multi-target vaccine design will allocate peptide resources for inducing disease immunity based on the presentation and respective target probabilities as shown in FIG. 8, for example. In some embodiments, presentations correspond to the prevalence of targets in different human populations or different risk groups. The probability of a target in a population is computed by summing for each possible presentation the probability of that presentation times the probability of the target in that presentation. FIG. 8 shows weights used for merging individual vaccines for each target (row) into combined vaccines for each disease indication (column). Values indicate the observed fraction of cases containing each target mutation. Data are from The Cancer Genome Atlas (TCGA). For each disease indication, TCGA data are filtered to cases where the Primary Site is the indication.

In some embodiments, the same vaccine design will be generated for mutations to different proteins when the base peptides generated by the mutations to the different proteins are identical. For example, in some embodiments of base peptide selection the following mutations have identical vaccine designs because they share the same set of base peptides: HRAS Q61K, NRAS Q61K, and KRAS Q61K; HRAS Q61L, NRAS Q61L, and KRAS Q61L; HRAS Q61R, NRAS Q61R, and KRAS Q61R. Referring to FIG. 8, in some embodiments, when two mutations have identical individual vaccine designs, their presentation specific probabilities are added when weighting the individual vaccine design for inclusion in a combined vaccine as described below (e.g., for Thyroid Cancer NRAS Q61R and HRAS Q61R).

Figure 9:
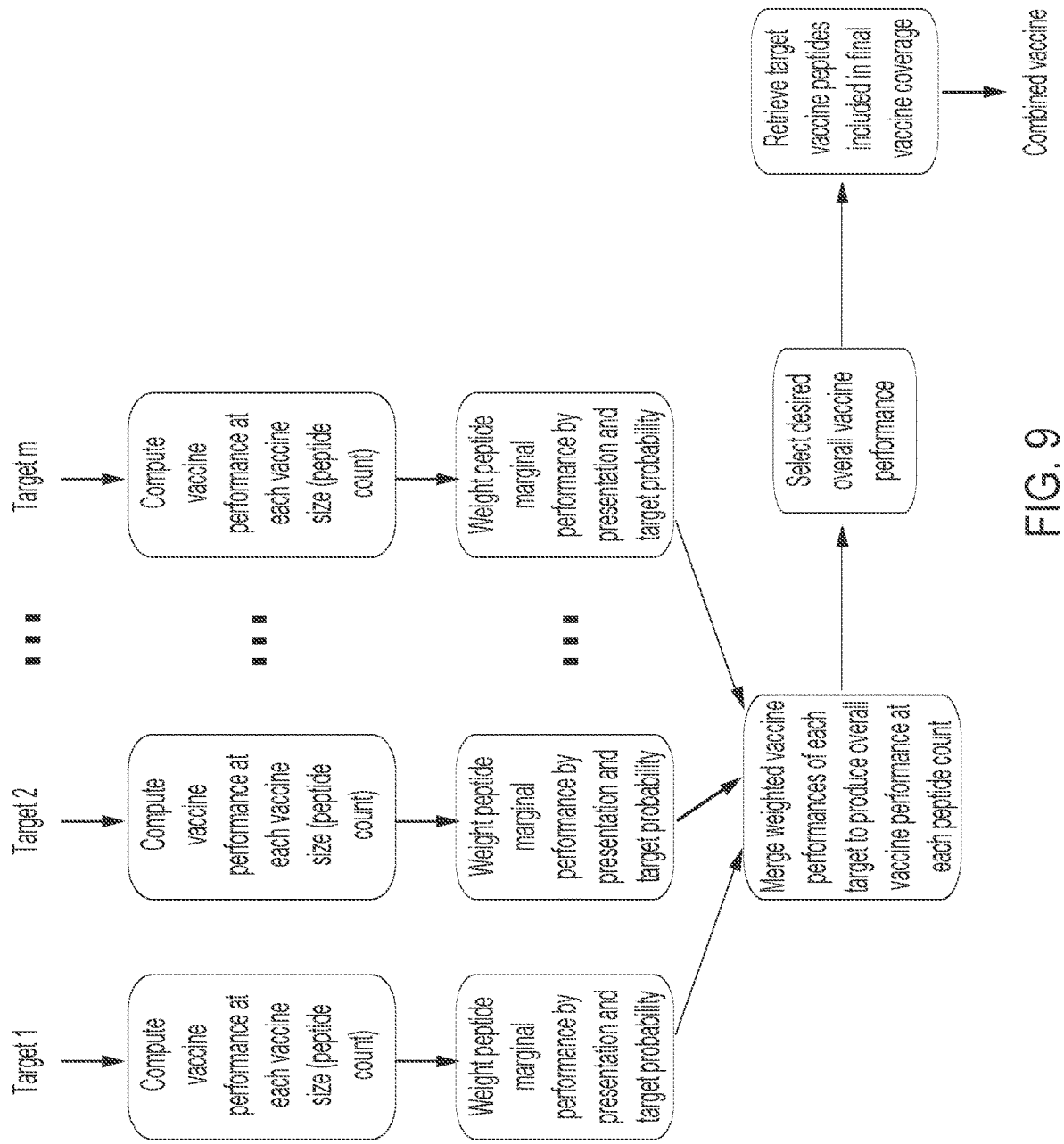
FIG. 9 is a flow chart showing a multiple target (combined) vaccine optimization method.

Referring to FIG. 9, in some embodiments, the method first includes designing an individual peptide vaccine for each target to create a combined vaccine design for multiple targets. This initially results in sets of target-specific vaccine designs. In some embodiments, the marginal predicted vaccine performance of each target-specific vaccine at size k is defined by predicted vaccine performance at size k minus the predicted vaccine performance of the vaccine at size k minus one. The composition of a vaccine may change as the number of peptides used in the vaccine increases, and thus for computing contributions to a combined vaccine, the marginal predicted vaccine performance of each target-specific vaccine is used instead of a specific set of peptides.

In some embodiments, the weighted marginal predicted vaccine performance of a target-specific vaccine design for each target specific vaccine size is computed as shown in FIG. 9. For a given target specific vaccine size, its weighted predicted vaccine performance is computed by multiplying its predicted vaccine performance times the probability of the target in the population (e.g., by using values as shown in FIG. 8). The marginal weighted predicted vaccine performance for a target specific vaccine is its weighted coverage at size k minus its coverage a size k minus one. The marginal weighted predicted vaccine performance of a target specific vaccine of size one is its weighted predicted vaccine performance. The marginal weighted predicted vaccine performances for all vaccines are combined into a single list, and the combined list is sorted from largest to least by the weighted marginal predicted vaccine performances of the target specific vaccines as shown in FIG. 9. The combined vaccine of size n is then determined by the first n elements of this list. The peptides for the combined vaccine are determined by the individual peptide target vaccines whose sizes add to n and whose weighted predicted vaccine performances sums to the same sum as the first n elements of the sorted list. This maximizes the predicted vaccine performance of the combined vaccine of size n.

In some embodiments, the combined multiple target vaccine can be designed on its overall predicted coverage for the disease described depending on the presentation table used (e.g., see FIG. 8), by its predicted coverage for a specific indication, and/or by its predicted coverage for a specific target by adjusting the weighting used for predicted vaccine performance accordingly. Once a desired level of coverage is selected, the peptides of the combined vaccine are determined by the contributions of target-specific designs. For example, if the combined vaccine includes a target-specific vaccine of size k, then the vaccine peptides for this target at size k are used in the combined vaccine.

As an example of one embodiment, FIG. 8 shows mutations (e.g., KRAS G12D, G12V, and G12R) and their respective probabilities of occurring in an individual with different cancer indications (e.g., pancreatic cancer). The marginal population coverage of each target-specific vaccine at a given vaccine size is the improvement in coverage at that size and the size minus one. The coverage with no peptides is zero. The marginal coverage of each target-specific vaccine is multiplied by the probability of the target in the population as determined by the proportions as shown in FIG. 8 for a selected indication (e.g., pancreatic cancer). These weighted marginal coverages of all target-specific vaccines are sorted to determine the best target-specific compositions, and the resulting list describes the composition of a combined vaccine for the selected indication at each size k by taking the first k elements of the list. At each combined vaccine size, different components of the target-specific vaccines are utilized for the indication illustrated.

Combined Vaccine Design Procedure

In some embodiments, the procedure described herein is used to combine individual compact vaccines optimized for different targets into a single optimized combined vaccine.

In some embodiments, the computational inputs for the procedure are:

$\mathcal{T}$: Set of neoantigen or pathogenic targets of interest (e.g., KRAS G12D, KRAS G12V, KRAS G12R, BCR-ABL b3a2, BCR-ABL b2a2)

$\mathcal{V}$: Vaccine sets optimized individually for each target. Let $\mathcal{V}_{t,k}$ denote the optimal vaccine set of exactly k peptides for target t ET (e.g., as computed by the procedures describe above). Note that $\mathcal{V}_{t,k+1}$ may not necessarily be a superset of $\mathcal{V}_{t,k}$.

W: $\mathcal{T} \rightarrow [0,1]$: Target weighting function mapping each target t∈$\mathcal{T}$ to a probability or weight of t in a particular presentation of interest (e.g., pancreatic cancer; see Exhibit A, Table 1 for example).

POPULATIONCOVERAGE: $\mathcal{V} \rightarrow [0,1]$: Function mapping a peptide set into population coverage (e.g., EvalVax). This function may also take as input additional parameters, including HLA haplotype frequencies and a minimum per-individual number of peptide-HLA hits N (here, we compute coverage as $P(n \geq 1)$ using EvalVax-Robust).

At Step 1, for each target t (individually) compute optimized vaccines of sizes 1 to m as the sets $\mathcal{V}_{t,k}$ where k denotes the size of the vaccine and then compute their vaccine performance at each vaccine size. For each target t (individually) and vaccine size (peptide count) k, the unweighted population coverage $c_{t,k}$ is computed:

$$c_{t,k} = \text{PopulationCoverage}(\mathcal{V}_{t,k}) \forall t \in \mathcal{T}, k$$

In some embodiments, for each target, t, $c_{t,k}$ is generally monotonically increasing and concave down for increasing values of k (each additional peptide increases coverage but with decreasing returns).

At Step 2, vaccine marginal performance is computed and weighted by each target's prevalence weight. For each target t (individually), the marginal coverage $m_{t,k}$ is computed of the k-th peptide added to the vaccine set:

$$m_{t,k} = \begin{cases} c_{t,k} & \text{if } k = 1 \\ c_{t,k} - c_{t,k-1}, & \text{otherwise} \end{cases} \forall t \in \mathcal{T}, k$$

In some embodiments, for each target t, $m_{t,k}$ should be a monotonically decreasing function in k (by Step 1 above).

The weighted marginal population coverage $\tilde{m}_{t,k}$ is computed using weights of each target in W:

$$\tilde{m}_{t,k} = W(t) \cdot m_{t,k} \forall t \in \mathcal{T}, k$$

The weighted marginal population coverage gives the effective marginal coverage of the k-th peptide in the vaccine weighted by the prevalence of the target in the presentation (by multiplication with the probability/weight of the target in the presentation).

At Step 3, the weighted vaccine performances are merged for all targets to produce combined vaccine designs at each peptide count. The individual vaccines are combined into a combined vaccine via the MERGEMULTI procedure called on the weighted marginal population coverage lists $\tilde{m}_t = [\tilde{m}_{t,k} \in 1, 2, \ldots]$. FIG. 10 shows an example Python implementation of the MERGEMULTI function. This procedure takes as input multiple sorted (descending) lists and merges them into a single sorted (descending) list. Let M indicate the output of MERGEMULTI where each element $M_k$ contains both the marginal weighted coverage and source (target) of the k-th peptide in the combined vaccine. The combined vaccine contains peptides from different targets. In particular, the combined vaccine with k peptides contains $C_{t,k} = \Sigma_{j \leq k} \mathbb{1}\{M_k \text{ from } t\}$ peptides from target t. $C_{t,k} \in [0, \ldots, k]$ and $\Sigma_t C_{t,k} = k$ ($C_{t,k}$ gives the distribution of the k peptides in the combined vaccine across the targets).

At Step 4, a vaccine with a desired performance is selected. The final vaccine size k can vary based upon the specific population coverage goals of the vaccine. The marginal weighted coverage values of the combined vaccine $M_k$ can be cumulatively summed over k to give the overall effective (target-weighted) population coverage of the combined vaccine containing k peptides as $\Sigma_{j \leq K} M_k$ (taking into account both the probabilities/weights of the targets in the presentation and the expected population coverage of peptides based on HLA display).

At Step 5, the vaccine peptides corresponding to the target coverage is retrieved for the final vaccine size k. The optimal combined vaccine set $\hat{V}_k$ for the final vaccine size k is defined as:

$$\hat{V}_k = \bigcup_{t \in \mathcal{T}} V_{t,C_{t,k}}$$

Thus, the combined vaccine with k peptides is the combination of the optimal individual ($C_{t,k}$)-peptide vaccines.

mRNA and DNA Vaccines

In some embodiments, vaccine peptides are encoded as mRNA or DNA molecules and are administered for expression in vivo. One example of the delivery of vaccines by mRNA is found in Kranz et al. (2016), incorporated by reference in its entirety herein. In some embodiments, vaccine peptides are encoded in more than one mRNA or DNA molecule as is disclosed in Sahin et. al. (2017), incorporated by reference in its entirety herein. In one embodiment, a construct comprises 20 peptides, including a ten-peptide MHC class I BCR-ABL b3a2 vaccine and a ten-peptide MHC class II BCR-ABL b3a2 vaccine, as optimized by the procedure described herein. Peptides are prepended with a secretion signal sequence at the N-terminus and followed by an MHC class I trafficking signal (MITD) (See Kreiter et al., 2008; Sahin et al., 2017, incorporated by reference in their entireties herein). The MITD has been shown to route antigens to pathways for HLA class I and class II presentation (Kreiter et al., 2008). Here we combine all peptides of each MHC class into a single construct using non-immunogenic glycine/serine linkers from Sahin et al. (2017), though it is also plausible to construct individual constructs containing single peptides with the same secretion and MITD signals as demonstrated by Kreiter et al. (2008).

In some embodiments, the amino acid sequence encoded by the mRNA vaccine comprises SEQ ID NO: 62113. Underlined amino acids correspond to the signal peptide (or leader) sequence. Bolded amino acids correspond to MHC class I (8-11 amino acids in length; 10 peptides) and MHC class II (13-25 amino acids in length; 10 peptides) peptide sequences. Italicized amino acids correspond to the trafficking signal. In alternate embodiments, any number and variation of peptide sequences disclosed herein can be included in an mRNA vaccine comprising the signal peptide sequence and the trafficking signal as shown in SEQ ID NO: 62113 below.

(SEQ ID NO: 62113)
MRVTAPRTLILLLSGALALTETWAGSGGSGGGGSGGA

MGFKQSSKGGSGGGGSGGGYKQSSKAMGGSGGGGSG

GKQLQRPVASDYGGSGGGGSGGKTLQRPVASDWGGS

GGGGSGGKYSSKALQRGGSGGGGSGGSAKALQRPMG

GSGGGGSGGSAKALQRPYGGSGGGGSGGSTKALQRP

LGGSGGGGSGGSTTGFKQSSKGGSGGGGSGGSTTGF

KQSSRGGSGGGGSGGLNVIVHSATGIKQISAALIRP

VASDGGSGGGGSGGLNVIVHSATGIKQISSALIRPV

ASDGGSGGGGSGGSATGFFQSKKFLQVPVASDFGGS

GGGGSGGSATGFKQFSIALRRPVASDFGGSGGGGSG

GSATGFKQISRALSRPVASDFGGSGGGGSGGSATGF

KQSSFALIRPVASDFGGSGGGGSGGSATGFKQSSRA

LSRAVANDFGGSGGGGSGGSATGFNQSAKVLQAPVA

SDFGGSGGGGSGGYGFLNVIVHSATGFKQTSFALNR

PVGGSGGGGSGGYGFLNVIVHSATGIKQASNALARP

VGGSLGGGGSGIVG*IVAGLAVLAVWIGAWATVMCRR*

*KSSGGKGGSYSQAASSDSAQGSDVSLTA*.

In some embodiments, the vaccine is an mRNA vaccine comprising a nucleic acids sequence encoding the amino acid sequence consisting of SEQ ID NO: 62113. In some embodiments, the nucleic acid sequence of the mRNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 62113.

In some embodiments, the vaccine is a DNA vaccine comprising a nucleic acids sequence encoding the amino acid sequence consisting of SEQ ID NO: 62113. In some embodiments, the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 62113.

In some embodiments, one or more MHC class I and/or MHC class II peptides disclosed herein (SEQ ID NO: 1 to 62113) can be encoded in one or more mRNA or DNA molecules and administered for expression in vivo. In some embodiments, between about 2 and about 40 peptide sequences are encoded in one or more mRNA constructs. In some embodiments, between about 2 and about 40 peptide sequences are encoded in one or more DNA constructs (i.e., nucleic acids encoding the amino acids sequences comprising on or more of SEQ ID NOs: 1 to 62113). In some embodiments, the amino acid sequence of the mRNA vaccine or the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to any of SEQ ID NOs: 1 to 62113.

In some embodiments, mRNA encoded vaccine peptides are used as the payload of a self-amplifying RNA vaccine. In one embodiment, the mRNA sequence encoding the vaccine peptides replaces one or more structural proteins of an infectious alphavirus particle as described in Geall et al. (2012) that is incorporated herein by reference. As is described by Geall et al. (2012), self-amplifying RNA vaccines can increase the efficiency of antigen production in vivo.

Non-Limiting Embodiments of the Subject Matter

In one aspect, described herein is a composition comprising nucleic acid sequences encoding at least two amino acid sequences selected from the group consisting of SEQ ID NOs: 1 to 8, SEQ ID NOs: 10 to 17, and SEQ ID NOs: 19 to 44.

In some embodiments, the nucleic acid sequences are contained in a construct for in vivo expression of the nucleic acid sequences.

In some embodiments, an administration of the nucleic acid sequences causes one or more peptides encoded by the nucleic acid sequences to be displayed by an HLA class I molecule in a subject.

In some embodiments, the nucleic acid sequences are contained in a construct for in vivo expression of at least two peptides encoded by the nucleic acid sequences, wherein an administration of the nucleic acid sequences causes: a first peptide of the at least two peptides to be displayed by a first plurality of HLA class I alleles in the subject; and a second peptide of the at least two peptides to be displayed by a second plurality of HLA class I alleles in the subject, wherein the first plurality of HLA class I alleles and the second plurality of HLA class I alleles differ by at least one HLA class I allele.

In some embodiments, the one or more peptides is a modified or an unmodified fragment of a BCL-ABL gene fusion. In some embodiments, the BCR-ABL gene fusion is b3a2 or b2a2. In some embodiments, the two or more amino acid sequences are selected based on a prevalence of the BCR-ABL gene fusion in a risk group that the subject belongs to, and wherein the composition is administered in an effective amount to the subject to promote an immune response against cancer or to treat cancer, and wherein the cancer is associated with the BCR-ABL gene fusion.

In some embodiments, the nucleic acid sequences are configured for administration in an effective amount to the subject to treat cancer.

In another aspect, described herein is a peptide composition comprising at least two peptides selected from the group consisting of SEQ ID NOs: 1 to 8, SEQ ID NOs: 10 to 17, and SEQ ID NOs: 19 to 44.

In some embodiments, a peptide in the peptide composition is configured for display by a HLA class I molecule in a subject.

In some embodiments, an administration of a first peptide of the at least two peptides causes: the first peptide to be displayed by a first plurality of HLA class I alleles in a subject; and a second peptide of the at least two peptides to be displayed by a second plurality of HLA class I alleles in a subject, wherein the first plurality of HLA class I alleles and the second plurality of HLA class I alleles differ by at least one HLA class I allele.

In some embodiments, a peptide in the peptide composition is a modified or an unmodified fragment of a BCL-ABL gene fusion. In some embodiments, the BCR-ABL gene fusion is b3a2 or b2a2. In some embodiments, the at least two peptides are selected based on a prevalence of the BCR-ABL gene fusion in a risk group that the subject belongs to, and wherein the peptide composition is administered in an effective amount to the subject to promote an immune response against cancer or to treat cancer, and wherein the cancer is associated with the BCR-ABL gene fusion.

In some embodiments, the peptide composition is configured for administration in an effective amount to a subject to treat cancer.

In another aspect, described herein are nucleic acid sequences encoding one or more amino acid sequences selected from the group consisting of SEQ ID NOs: 46 to 112.

In some embodiments, the nucleic acid sequence are contained in a construct for in vivo expression of the nucleic acid sequences.

In some embodiments, an administration of the nucleic acid sequences causes one or more peptides encoded by the nucleic acid sequences to be displayed by an HLA class II molecule in a subject.

In some embodiments, the one or more amino acid sequences are derived from a modified or an unmodified fragment of a BCL-ABL gene fusion. In some embodiments, the BCR-ABL gene fusion is b3a2 or b2a2. In some embodiments, the one or more amino acid sequences are selected based on a prevalence of the BCR-ABL gene fusion in a risk group that the subject belongs to, and wherein the composition is administered in an effective amount to the subject to promote an immune response against cancer or to treat cancer, and wherein the cancer is associated with the BCR-ABL gene fusion.

In some embodiments, the composition is configured for administration in an effective amount to a subject to treat cancer.

In some embodiments, the nucleic acid sequences encode at least two amino acid sequences selected from the group consisting of SEQ ID NOs: 46 to 112.

In another aspect, described herein is a peptide composition comprising one or more peptides selected from the group consisting of SEQ ID NOs: 46 to 112.

In some embodiments, a peptide in the peptide composition is configured for display by an HLA class II molecule in a subject.

In some embodiments, a peptide in the peptide composition is a modified or an unmodified fragment of a BCL-ABL gene fusion. In some embodiments, the BCR-ABL gene fusion is b3a2 or b2a2. In some embodiments, the one or more peptides are selected based on a prevalence of the BCR-ABL gene fusion in a risk group that the subject belongs to, and wherein the peptide composition is administered in an effective amount to the subject to promote an immune response against cancer or to treat cancer, and wherein the cancer is associated with the BCR-ABL gene fusion.

In some embodiments, the peptide composition is configured for administration in an effective amount to a subject to treat cancer.

MHC Class I Peptide Sequences

In some embodiments, a peptide vaccine (single target or combined multiple target vaccine) comprises about 1 to 40 MHC class I peptides with each peptide consisting of 8 or more amino acids. In some embodiments, an MHC class I peptide vaccine is intended for a BCR-ABL gene fusion. In some embodiments, the BCR-ABL gene fusion is selected from the group consisting of b3a2 and b2a2. In some embodiments, an MHC class I peptide vaccine is intended to prevent cancer. In some embodiments, an MHC class I peptide vaccine is intended to treat cancer. In some embodiments, an MHC class I peptide vaccine is intended to prevent chronic myelogenous leukemia (CML), acute lymphoblastic leukemia (ALL), acute myelogenous leukemia (AML), or breast invasive ductal carcinoma. In some embodiments, an MHC class I peptide vaccine is intended to treat chronic myelogenous leukemia (CIVIL), acute lymphoblastic leukemia (ALL), acute myelogenous leukemia (AML), or breast invasive ductal carcinoma.

In some embodiments, the amino acid sequence vaccine for a MHC class I peptide vaccine for BCR-ABL comprises one or more of the SEQ ID NOs: 1 to 45. In some embodiments, any one of the peptides in the BCR-ABL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 45.

In some embodiments, the amino acid sequence vaccine for a MHC class I peptide vaccine for BCR-ABL comprises two or more of the SEQ ID NOs: 1 to 45. In some embodiments, any one of the peptides in the BCR-ABL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 45.

Table 1 shows MHC class I peptide sequences described herein including the respective SEQ ID NO, amino acid sequence corresponding to the SEQ ID NO, the seed amino acid sequence (i.e., the amino acid sequence of the wild type BCR-ABL protein fusion fragment), the amino acid substitution (if any) for heteroclitic peptides at positions 2 and C (carboxyl terminus), and notes detailing embodiments in which the peptide may be included in a combined peptide vaccine as described herein. SEQ ID NOs: 1-33, and 45 are derived from BCR-ABL b3a2, while SEQ ID NOs: 34-44 are derived from BCR-ABL b2a2. In some embodiments, any combination of peptides listed in Table 1 (SEQ ID NOs: 1 to 45) may be used to create a combined peptide vaccine having between about 1 and about 40 peptides. In some embodiments, any one of the peptides (peptides 1 to 45; SEQ ID NOs: 1 to 45) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1 to 45.

In some embodiments, any combination of the peptides listed in Table 1 in the "b3a2 Vaccine" column (SEQ ID NOs: 1 to 33 and SEQ ID NO: 45) may be used to create a combined peptide vaccine having between about 1 and about 40 peptides. In some embodiments, any one of these peptides in the combined vaccine comprises an amino acid sequence 80, 81, 82, 83, 84, 85, 86, 87, 88, 89, 90, 91, 92, 93, 94, 95, 96, 97, 98 or 99% identical to the peptides listed in Table 1 in the "b3a2 Vaccine" column (SEQ ID NOs: 1 to 33 and SEQ ID NO: 45).

In some embodiments, any combination of the peptides listed in Table 1 in the "b2a2 Vaccine" column (SEQ ID NOs: 34 to 44) may be used to create a combined peptide vaccine having between about 1 and about 40 peptides. In some embodiments, any one of these peptides in the combined vaccine comprises an amino acid sequence 80, 81, 82, 83, 84, 85, 86, 87, 88, 89, 90, 91, 92, 93, 94, 95, 96, 97, 98 or 99% identical to the peptides listed in Table 1 in the "b2a2 Vaccine" column (SEQ ID NOs: 34 to 44).

Additional amino acid sequences of MHC class I vaccine peptides are provided in Sequence Listings (SEQ ID NOs: 113 to 700). In some embodiments, any combination of MHC class I peptides disclosed herein (SEQ ID NOs: 1 to 45 and SEQ ID NOs: 113 to 700) may be used to create a combined peptide vaccine having between about 1 and about 40 peptides. In some embodiments, any one of the peptides (SEQ ID NOs: 1 to 45 and SEQ ID NOs: 113 to 700) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1 to 45 or SEQ ID NOs: 113 to 700.

TABLE 1

Example Vaccine Peptides (MHC class 1)

| SEQ ID NO | Sequence corresponding to SEQ ID | Seed | Heteroclitic Modification P2 | Heteroclitic Modification C-term | Present in b3a2 Vaccine Sizes | Present in b2a2 Vaccine Sizes |
|---|---|---|---|---|---|---|
| SEQ ID NO: 1 | STTGFKQSSK | SATGFKQSSK | A2T | — | 1-30 | |
| SEQ ID NO: 2 | STKALQRPV | SSKALQRPV | S2T | — | 11-19, 23-30 | |
| SEQ ID NO: 3 | KQLQRPVASDF | KALQRPVASDF | A2Q | — | 12-30 | |
| SEQ ID NO: 4 | SVTGFKQSSR | SATGFKQSSK | A2V | K10R | 13-30 | |
| SEQ ID NO: 5 | GYKQSSKAL | GFKQSSKAL | F2Y | — | 14-30 | |
| SEQ ID NO: 6 | KVSSKALQR | KQSSKALQR | Q2V | — | 15-30 | |

TABLE 1-continued

Example Vaccine Peptides (MHC class 1)

| SEQ ID NO | Sequence | Sequence corresponding to SEQ ID Seed | Heteroclitic Modifi-P2 | Heteroclitic Modifi-C-term | Present in b3a2 Vaccine Sizes | Present in b2a2 Vaccine Sizes |
|---|---|---|---|---|---|---|
| SEQ ID NO: 7 | SAKALQRPF | SSKALQRPV | S2A | V9F | 16-30 | |
| SEQ ID NO: 8 | SSKALQRPA | SSKALQRPV | — | V9A | 17-19, 23-30 | |
| SEQ ID NO: 9 | SATGFKQSSR | SATGFKQSSK | — | K10R | 18-30 | |
| SEQ ID NO: 10 | GYKQSSKAF | GFKQSSKAL | F2Y | L9F | 19-30 | |
| SEQ ID NO: 11 | AMGFKQSSK | ATGFKQSSK | T2M | — | 2-30 | |
| SEQ ID NO: 12 | SGKALQRPK | SSKALQRPV | S2G | V9K | 20-22 | |
| SEQ ID NO: 13 | SIKALQRPA | SSKALQRPV | S2I | V9A | 20-22 | |
| SEQ ID NO: 14 | KSSSKALQR | KQSSKALQR | Q2S | — | 20-30 | |
| SEQ ID NO: 15 | STKALQRPK | SSKALQRPV | S2T | V9K | 21-22, 29-30 | |
| SEQ ID NO: 16 | HTATGFKQSSR | HSATGFKQSSK | S2T | K11R | 22-30 | |
| SEQ ID NO: 17 | KMSSKALQR | KQSSKALQR | Q2M | — | 23-30 | |
| SEQ ID NO: 18 | STKALQRPVK | SSKALQRPVA | S2T | A10K | 23-30 | |
| SEQ ID NO: 19 | SQKALQRPK | SSKALQRPV | S2Q | V9K | 24-30 | |
| SEQ ID NO: 20 | KTSSKALQR | KQSSKALQR | Q2T | — | 25-30 | |
| SEQ ID NO: 21 | KLSSKALQR | KQSSKALQR | Q2L | — | 27-30 | |
| SEQ ID NO: 22 | SVKALQRPV | SSKALQRPV | S2V | — | 28 | |
| SEQ ID NO: 23 | KISSKALQR | KQSSKALQR | Q2I | — | 29-30 | |
| SEQ ID NO: 24 | SAKALQRPY | SSKALQRPV | S2A | V9Y | 3-7, 10-30 | |
| SEQ ID NO: 25 | SVKALQRPK | SSKALQRPV | S2V | V9K | 30 | |
| SEQ ID NO: 26 | STKALQRPS | SSKALQRPV | S2T | V9S | 4-7, 26, 29-30 | |
| SEQ ID NO: 27 | KQLQRPVASDY | KALQRPVASDF | A2Q | F11Y | 5-30 | |
| SEQ ID NO: 28 | STTGFKQSSR | SATGFKQSSK | A2T | K10R | 6-30 | |
| SEQ ID NO: 29 | GYKQSSKAM | GFKQSSKAL | F2Y | L9M | 7-30 | |
| SEQ ID NO: 30 | STKALQRPL | SSKALQRPV | S2T | V9L | 8-19, 23-30 | |
| SEQ ID NO: 31 | KYSSKALQR | KQSSKALQR | Q2Y | — | 8-30 | |
| SEQ ID NO: 32 | SAKALQRPM | SSKALQRPV | S2A | V9M | 8-30 | |
| SEQ ID NO: 33 | KTLQRPVASDW | KALQRPVASDF | A2T | F11W | 9-30 | |
| SEQ ID NO: 34 | LAINKEEAM | LTINKEEAL | T2A | L9M | | 1-10 |
| SEQ ID NO: 35 | KEEALQRPVL | KEEALQRPVA | — | A10L | | 10 |
| SEQ ID NO: 36 | LSINKEEAW | LTINKEEAL | T2S | L9W | | 10 |
| SEQ ID NO: 37 | KEEALQRPL | KEEALQRPV | — | V9L | | 2-10 |
| SEQ ID NO: 38 | KEEALQRPA | KEEALQRPV | — | V9A | | 3-10 |
| SEQ ID NO: 39 | LTINKEEAW | LTINKEEAL | — | L9W | | 4, 7-10 |
| SEQ ID NO: 40 | LAINKEEAL | LTINKEEAL | T2A | — | | 5-10 |
| SEQ ID NO: 41 | KEEALQRPM | KEEALQRPV | — | V9M | | 5-6, 9 |
| SEQ ID NO: 42 | LAINKEEAY | LTINKEEAL | T2A | L9Y | | 6-10 |

TABLE 1-continued

Example Vaccine Peptides (MHC class 1)

| SEQ ID NO | Sequence corresponding to SEQ ID | Seed | Heteroclitic Modification P2 | Heteroclitic Modification C-term | Present in b3a2 Vaccine Sizes | Present in b2a2 Vaccine Sizes |
|---|---|---|---|---|---|---|
| SEQ ID NO: 43 | LTINKEEAF | LTINKEEAL | — | L9F | | 7-10 |
| SEQ ID NO: 44 | LAINKEEAF | LTINKEEAL | T2A | L9F | | 8-10 |
| SEQ ID NO: 45 | SSKALQRPVA | SSKALQRPVA | — | | 20-22, 27-28 | |

MHC Class II Peptide Sequences

In some embodiments, a peptide vaccine (single target or combined multiple target vaccine) comprises about 1 to 40 MHC class II peptides with each peptide consisting of about 20 amino acids. In some embodiments, an MHC class II peptide vaccine is intended for a BCR-ABL gene fusion. In some embodiments, the BCR-ABL gene fusion is selected from the group consisting of b3a2 and b2a2. In some embodiments, an MHC class II peptide vaccine is intended to prevent cancer. In some embodiments, an MHC class II peptide vaccine is intended to treat cancer. In some embodiments, an MHC class I peptide vaccine is intended to prevent chronic myelogenous leukemia (CML), acute lymphoblastic leukemia (ALL), acute myelogenous leukemia (AML), or breast invasive ductal carcinoma. In some embodiments, an MHC class I peptide vaccine is intended to treat chronic myelogenous leukemia (CIVIL), acute lymphoblastic leukemia (ALL), acute myelogenous leukemia (AML), or breast invasive ductal carcinoma.

In some embodiments, the amino acid sequence vaccine for a MHC class II peptide vaccine for BCR-ABL comprises one or more of the SEQ ID NOs: 46 to 112. In some embodiments, any one of the peptides in the BCR-ABL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 46 to 112.

In some embodiments, the amino acid sequence vaccine for a MHC class II peptide vaccine for BCR-ABL comprises two or more of the SEQ ID NOs: 46 to 112. In some embodiments, any one of the peptides in the BCR-ABL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 46 to 112.

Table 2 summarizes MHC class II peptide sequences described herein including the respective SEQ ID NO, amino acid sequence corresponding to the SEQ ID NO, the amino acid sequence corresponding to the peptide's binding core, the seed amino acid sequence (i.e., the amino acid sequence of the wild type BCR-ABL protein fusion fragment), the seed amino acid sequence of the binding core, and the amino acid substitution (if any) for heteroclitic peptides at positions 1, 4, 6, and 9. Table 2 includes peptide sequences comprising SEQ ID NOs: 46 to 112. SEQ ID NOs: 46 to 112 (Table 2) encode for recombinant peptides. SEQ ID NOs: 46-78 are derived from BCR-ABL b3a2, while SEQ IS NOs: 79-112 are derived from BCR-ABL b2a2. In some embodiments, any combination of peptides listed in Table 2 (SEQ ID NOs: 46 to 112) may be used to create a single target (individual) or combined peptide vaccine having between about 1 and about 40 peptides. In some embodiments, any one of the peptides (peptides 46 to 112; SEQ ID NOs: 46 to 112) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 46 to 112.

In some embodiments, any combination of the peptides listed in Table 2 in the "b3a2 Vaccine" column (SEQ ID NOs: 46 to 78) may be used to create a combined peptide vaccine having between about 1 and about 40 peptides. In some embodiments, any one of these peptides in the combined vaccine comprises an amino acid sequence 80, 81, 82, 83, 84, 85, 86, 87, 88, 89, 90, 91, 92, 93, 94, 95, 96, 97, 98 or 99% identical to the peptides listed in Table 2 in the "b3a2 Vaccine" column (SEQ ID NOs: 46 to 78).

In some embodiments, any combination of the peptides listed in Table 2 in the "b2a2 Vaccine" column (SEQ ID NOs: 79 to 112) may be used to create a combined peptide vaccine having between about 1 and about 40 peptides. In some embodiments, any one of these peptides in the combined vaccine comprises an amino acid sequence 80, 81, 82, 83, 84, 85, 86, 87, 88, 89, 90, 91, 92, 93, 94, 95, 96, 97, 98 or 99% identical to the peptides listed in Table 2 in the "b2a2 Vaccine" column (SEQ ID NOs: 79 to 112).

Additional amino acid sequences of MHC class II vaccine peptides are provided in Sequence Listings (SEQ ID NOs: 701 to 62112). In some embodiments, any combination of MHC class II peptides disclosed herein (SEQ ID NOs: 46 to 112 and SEQ ID NOs: 701 to 62112) may be used to create a combined peptide vaccine having between about 1 and about 40 peptides. In some embodiments, any one of the peptides (SEQ ID NOs: 46 to 112 and SEQ ID NOs: 701 to 62112) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 46 to 112 or SEQ ID NOs: 701 to 62112.

In some embodiments, any combination of WIC class I and/or MEW class II peptides disclosed herein (SEQ ID NOs: 1 to 62113) may be used to create a single target (individual) or combined peptide vaccine having between about 2 and about 40 peptides. In some embodiments, any one of the peptides (peptides 1 to 62113; SEQ ID NOs: 1 to 62113) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1 to 62113.

TABLE 2

Example Vaccine Peptides (MHC class II)

| SEQ ID NO | Sequence corresponding to SEQ ID | Core | Seed | Seed Core | Heteroclitic Modification P1 | Heteroclitic Modification P4 | Heteroclitic Modification P6 | Heteroclitic Modification P9 | Present in b3a2 Vaccine Sizes | Present in b2a2 Vaccine Sizes |
|---|---|---|---|---|---|---|---|---|---|---|
| SEQ ID NO: 46 | LNVIVHSATGFKQIS AALARPVASD | FKQIS AALA | LNVIVHSATGFKQS SKALQRPVASD | FKQSS KALQ | — | S4I | K6A | Q9A | 1-2, 18-30 | |
| SEQ ID NO: 47 | LNVIVHSATGIKQISA ALIRPVASD | IKQISA ALI | LNVIVHSATGFKQS SKALQRPVASD | FKQSS KALQ | F1I | S4I | K6A | Q9I | 10-30 | |
| SEQ ID NO: 48 | SATGFKQISRALARP VASDF | FKQISR ALA | SATGFKQSSKALQR PVASDF | FKQSS KALQ | — | S4I | K6R | Q9A | 12-30 | |
| SEQ ID NO: 49 | YGFLNVIVHSATGYK QFSWALMRPV | YKQFS WALM | YGFLNVIVHSATGF KQSSKALQRPV | FKQSS KALQ | F1Y | S4F | K6W | Q9M | 13-14, 16-17 | |
| SEQ ID NO: 50 | SATGFKQTSFALIRPV ASDF | FKQTS FALI | SATGFKQSSKALQR PVASDF | FKQSS KALQ | — | S4T | K6F | Q9I | 13-30 | |
| SEQ ID NO: 51 | YGFLNVIVHSATGFK QNSTALARPV | FKQNS TALA | YGFLNVIVHSATGF KQSSKALQRPV | FKQSS KALQ | — | S4N | K6T | Q9A | 14-30 | |
| SEQ ID NO: 52 | SATGFKQSSRALARA VAADF | RALAR AVAA | SATGFKQSSKALQR PVASDF | KALQR PVAS | K1R | Q4A | P6A | S9A | 15-30 | |
| SEQ ID NO: 53 | LNVIVHSATGMKQFS AALVRPVASD | MKQFS AALV | LNVIVHSATGFKQS SKALQRPVASD | FKQSS KALQ | F1M | S4F | K6A | Q9V | 16-17, 22 | |
| SEQ ID NO: 54 | SATGFNQSAKVLQGP VASDF | NQSAK VLQG | SATGFKQSSKALQR PVASDF | KQSSK ALQR | K1N | S4A | A6V | R9G | 17-30 | |
| SEQ ID NO: 55 | LNVIVHSATGYKQFS AALTRPVASD | YKQFS AALT | LNVIVHSATGFKQS SKALQRPVASD | FKQSS KALQ | F1Y | S4F | K6A | Q9T | 18-21, 23-30 | |
| SEQ ID NO: 56 | SATGFKQFSLALRRP VASDF | FKQFS LALR | SATGFKQSSKALQR PVASDF | FKQSS KALQ | — | S4F | K6L | Q9R | 19-30 | |
| SEQ ID NO: 57 | SATGFKQFSVALRRP VASDF | FKQFS VALR | SATGFKQSSKALQR PVASDF | FKQSS KALQ | — | S4F | K6V | Q9R | 2-4, 11-30 | |
| SEQ ID NO: 58 | SATGFKQISYALIRPV ASDF | FKQIS YALI | SATGFKQSSKALQR PVASDF | FKQSS KALQ | — | S4I | K6Y | Q9I | 20-30 | |
| SEQ ID NO: 59 | YGFLNVIVHSATGFK QISTALARPV | FKQIST ALA | YGFLNVIVHSATGF KQSSKALQRPV | FKQSS KALQ | — | S4I | K6T | Q9A | 21-30 | |
| SEQ ID NO: 60 | LNVIVHSATGIKQISR ALARPVASD | IKQISR ALA | LNVIVHSATGFKQS SKALQRPVASD | FKQSS KALQ | F1I | S4I | K6R | Q9A | 22-30 | |
| SEQ ID NO: 61 | SATGFKQSSRALIRPV ATDF | RALIRP VAT | SATGFKQSSKALQR PVASDF | KALQR PVAS | K1R | Q4I | — | S9T | 23-30 | |
| SEQ ID NO: 62 | LNVIVHSATGYKQIS AALARPVASD | YKQIS AALA | LNVIVHSATGFKQS SKALQRPVASD | FKQSS KALQ | F1Y | S4I | K6A | Q9A | 24, 29-30 | |
| SEQ ID NO: 63 | LNVIVHSATGWKQFS AALVRPVASD | WKQFS AALV | LNVIVHSATGFKQS SKALQRPVASD | FKQSS KALQ | F1W | S4F | K6A | Q9V | 25-30 | |
| SEQ ID NO: 64 | SATGFKQFSLALKRP VASDF | FKQFS LALK | SATGFKQSSKALQR PVASDF | FKQSS KALQ | — | S4F | K6L | Q9K | 25-30 | |
| SEQ ID NO: 65 | SATGFKQESFALIRPV ASDF | FKQES FALI | SATGFKQSSKALQR PVASDF | FKQSS KALQ | — | S4E | K6F | Q9I | 26-30 | |
| SEQ ID NO: 66 | SATGFKQISRALTRP VASDF | FKQISR ALT | SATGFKQSSKALQR PVASDF | FKQSS KALQ | — | S4I | K6R | Q9T | 27-30 | |
| SEQ ID NO: 67 | YGFLNVIVHSATGFK QNSNALARPV | FKQNS NALA | YGFLNVIVHSATGF KQSSKALQRPV | FKQSS KALQ | — | S4N | K6N | Q9A | 28-30 | |
| SEQ ID NO: 68 | LNVIVHSATGIKQISS ALIRPVASD | IKQISS ALI | LNVIVHSATGFKQS SKALQRPVASD | FKQSS KALQ | F1I | S4I | K6S | Q9I | 3-30 | |
| SEQ ID NO: 69 | SATGFKQISRALSRPV ASDF | FKQISR ALS | SATGFKQSSKALQR PVASDF | FKQSS KALQ | — | S4I | K6R | Q9S | 3-30 | |

TABLE 2-continued

Example Vaccine Peptides (MHC class II)

| SEQ ID NO | Sequence corresponding to SEQ ID | Core | Seed | Seed Core | Heteroclitic Modification P1 | Heteroclitic Modification P4 | Heteroclitic Modification P6 | Heteroclitic Modification P9 | Present in b3a2 Vaccine Sizes | Present in b2a2 Vaccine Sizes |
|---|---|---|---|---|---|---|---|---|---|---|
| SEQ ID NO: 70 | SATGFKQASFALVRP VASDF | FKQAS FALV | SATGFKQSSKALQR PVASDF | FKQSS KALQ | — | S4A | K6F | Q9V | 30 | |
| SEQ ID NO: 71 | SATGFKQSSFALIRPV ASDF | FKQSS FALI | SATGFKQSSKALQR PVASDF | FKQSS KALQ | — | | K6F | Q9I | 4-30 | |
| SEQ ID NO: 72 | YGFLNVIVHSATGFK QISAALARPV | FKQIS AALA | YGFLNVIVHSATGF KQSSKALQRPV | FKQSS KALQ | — | S4I | K6A | Q9A | 5, 7 | |
| SEQ ID NO: 73 | SATGFKQFSIALRRPV ASDF | FKQFSI ALR | SATGFKQSSKALQR PVASDF | FKQSS KALQ | — | S4F | K6I | Q9R | 5-30 | |
| SEQ ID NO: 74 | YGFLNVIVHSATGIK QASNALARPV | IKQAS NALA | YGFLNVIVHSATGF KQSSKALQRPV | FKQSS KALQ | F1I | S4A | K6N | Q9A | 6, 8-30 | |
| SEQ ID NO: 75 | SATGFKQSSRALSRA VANDF | RALSR AVAN | SATGFKQSSKALQR PVASDF | KALQR PVAS | K1R | Q4S | P6A | S9N | 6-30 | |
| SEQ ID NO: 76 | SATGFNQSAKVLQAP VASDF | NQSAK VLQA | SATGFKQSSKALQR PVASDF | KQSSK ALQR | K1N | S4A | A6V | R9A | 7-30 | |
| SEQ ID NO: 77 | SATGFFQSKKFLQVP VASDF | FQSKK FLQV | SATGFKQSSKALQR PVASDF | KQSSK ALQR | K1F | S4K | A6F | R9V | 8-30 | |
| SEQ ID NO: 78 | YGFLNVIVHSATGFK QTSFALNRPV | FKQTS FALN | YGFLNVIVHSATGF KQSSKALQRPV | FKQSS KALQ | — | S4T | K6F | Q9N | 9-12, 15, 18-30 | |
| SEQ ID NO: 79 | NSCVKLQTVHSIPFTI NKFEAIQRP | FTINKF EAI | NSCVKLQTVHSIPL TINKEEALQRP | LTINK EEAL | L1F | — | E6F | L9I | 1-30 | |
| SEQ ID NO: 80 | VKLQTVHSIPLTINKI ETLQAPVAS | INKIET LQA | VKLQTVHSIPLT INKEEALQRPVAS | INKEE ALQR | — | E4I | A6T | R9A | 10-30 | |
| SEQ ID NO: 81 | QTVHSIPLTINKEFAL MRPVANDFE | FALMR PVAN | QTVHSIPLTINK EEALQRPVASDFE | EALQR PVAS | E1F | Q4M | — | S9N | 11-30 | |
| SEQ ID NO: 82 | NSCVKLQTVHSIPFTI SKFEALQRP | FTISKF EAL | NSCVKLQTVHSIPL TINKEEALQRP | LTINK EEAL | L1F | N4S | E6F | — | 12-30 | |
| SEQ ID NO: 83 | VKLQTVHSIPITIIK AEAYQRPVAS | ITIIKA EAY | VKLQTVHSIPLT INKEEALQRPVAS | LTINK EEAL | L1I | N4I | E6A | L9Y | 12-30 | |
| SEQ ID NO: 84 | LQTVHSIPFTITKAEA IQR | FTITKA EAI | LQTVHSIPLTIN KEEALQRP | LTINK EEAL | L1F | N4T | E6A | L9I | 13, 21-22, 25-30 | |
| SEQ ID NO: 85 | LQTVHSIPFTIIKA EAIQR | FTIIKA EAI | LQTVHSIPLTINK EEALQR | LTINK EEAL | L1F | N4I | E6A | L9I | 14-30 | |
| SEQ ID NO: 86 | VKLQTVHSIPLTINKF ESLQIPVAS | INKFES LQI | VKLQTVHSIPLT INKEEALQRPVAS | INKEE ALQR | — | E4F | A6S | R9I | 14-30 | |
| SEQ ID NO: 87 | NSCVKLQTVHSIPFTI IKNEAVQRP | FTIIKN EAV | NSCVKLQTVHSIPL TINKEEALQRP | LTINK EEAL | L1F | N4I | E6N | L9V | 15-30 | |
| SEQ ID NO: 88 | VKLQTVHSIPLTFNK FESLQAPVAS | FNKFE SLQA | VKLQTVHSIPLT INKEEALQRPVAS | INKEE ALQR | I1F | E4F | A6S | R9A | 16-30 | |
| SEQ ID NO: 89 | NSCVKLQTVHSIP ITIIKAEALQRP | ITIIKA EAL | NSCVKLQTVHSIPL TINKEEALQRP | LTINK EEAL | L1I | N4I | E6A | — | 17-30 | |
| SEQ ID NO: 90 | VKLQTVHSIPLTIFKS EAVQRPVAS | LITFKS EAV | VKLQTVHSIPLT INKEEALQRPVAS | LTINK EEAL | — | N4F | E6S | L9V | 18 | |
| SEQ ID NO: 91 | NSCVKLQTVHSIPITI FKNEALQRP | ITIFKN EAL | NSCVKLQTVHSIPL TINKEEALQRP | LTINK EEAL | L1I | N4F | E6N | — | 19-30 | |
| SEQ ID NO: 92 | VKLQTVHSIPITIF KSEAIQRPVAS | ITIFKS EAI | VKLQTVHSIPLT INKEEALQRPVAS | LTINK EEAL | LII | N4F | E6S | L9I | 19-30 | |

TABLE 2-continued

Example Vaccine Peptides (MHC class II)

| SEQ ID NO | Sequence corresponding to SEQ ID | Core | Seed | Seed Core | Heteroclitic Modification P1 | Heteroclitic Modification P4 | Heteroclitic Modification P6 | Heteroclitic Modification P9 | Present in b3a2 Vaccine Sizes | Present in b2a2 Vaccine Sizes |
|---|---|---|---|---|---|---|---|---|---|---|
| SEQ ID NO: 93 | VKLQTVHSIPLTFNKFESLQVPVAS | FNKFESLQV | VKLQTVHSIPLTINKEEALQRPVAS | INKEEALQR | I1F | E4F | A6S | R9V | | 2-30 |
| SEQ ID NO: 94 | VKLQTVHSIPITILKSEAFQRPVAS | ITILKSEAF | VKLQTVHSIPLTINKEEALQRPVAS | LTINKEEAL | L1I | N4L | E6S | L9F | | 20 |
| SEQ ID NO: 95 | NSCVKLQTVHSIPITILKSEAFQRP | ITILKSEAF | NSCVKLQTVHSIPLTINKEEALQRP | LTINKEEAL | L1I | N4L | E6S | L9F | | 21-24, 26-30 |
| SEQ ID NO: 96 | VKLQTVHSIPLTINKFEALQIPVAS | INKFEALQI | VKLQTVHSIPLTINKEEALQRPVAS | INKEEALQR | — | E4F | — | R9I | | 22-30 |
| SEQ ID NO: 97 | LQTVHSIPFTIIKAEAVQR | FTIIKAEAV | LQTVHSIPLTINKEEALQR | LTINKEEAL | L1F | N4I | E6A | L9V | | 23-24, 30 |
| SEQ ID NO: 98 | NSCVKLQTVHSIPFTIMKSEAAQRP | FTIMKSEAA | NSCVKLQTVHSIPLTINKEEALQRP | LTINKEEAL | L1F | N4M | E6S | L9A | | 23-30 |
| SEQ ID NO: 99 | VKLQTVHSIPLTFNKLESLQAPVAS | FNKLESLQA | VKLQTVHSIPLTINKEEALQRPVAS | INKEEALQR | I1F | E4L | A6S | R9A | | 24-30 |
| SEQ ID NO: 100 | VKLQTVHSIPITILKNEAFQRPVAS | ITILKNEAF | VKLQTVHSIPLTINKEEALQRPVAS | LTINKEEAL | L1I | N4L | E6N | L9F | | 25 |
| SEQ ID NO: 101 | NSCVKLQTVHSIPFTINKFEALQRP | FTINKFEAL | NSCVKLQTVHSIPLTINKEEALQRP | LTINKEEAL | L1F | — | E6F | — | | 25-30 |
| SEQ ID NO: 102 | VKLQTVHSIPLTINKIERLQKPVAS | INKIERLQK | VKLQTVHSIPLTINKEEALQRPVAS | INKEEALQR | — | E4I | A6R | R9K | | 26-30 |
| SEQ ID NO: 103 | VKLQTVHSIPFTIFKSEALQRPVAS | FTIFKSEAL | VKLQTVHSIPLTINKEEALQRPVAS | LTINKEEAL | L1F | N4F | E6S | — | | 27-30 |
| SEQ ID NO: 104 | NSCVKLQTVHSIPITIFKSEALQRP | ITIFKSEAL | NSCVKLQTVHSIPLTINKEEALQRP | LTINKEEAL | L1I | N4F | E6S | — | | 28-30 |
| SEQ ID NO: 105 | VKLQTVHSIPLTILKSEAYQRPVAS | LTILKSEAY | VKLQTVHSIPLTINKEEALQRPVAS | LTINKEEAL | — | N4L | E6S | L9Y | | 29-30 |
| SEQ ID NO: 106 | LQTVHSIPFTITKSEAIQR | FTITKSEAI | LQTVHSIPLTINKEEALQR | LTINKEEAL | L1F | N4T | E6S | L9I | | 3-30 |
| SEQ ID NO: 107 | QTVHSIPLTINKDEPLQFPVASDFE | INKDEPLQF | QTVHSIPLTINKEEALQRPVASDFE | INKEEALQR | — | E4D | A6P | R9F | | 4-30 |
| SEQ ID NO: 108 | NSCVKLQTVHSIPFTIMKSEAVQRP | FTIMKSEAV | NSCVKLQTVHSIPLTINKEEALQRP | LTINKEEAL | L1F | N4M | E6S | L9V | | 5-30 |
| SEQ ID NO: 109 | VKLQTVHSIPLTINKIERLQRPVAS | INKIERLQR | VKLQTVHSIPLTINKEEALQRPVAS | INKEEALQR | — | E4I | A6R | — | | 6-30 |
| SEQ ID NO: 110 | VKLQTVHSIPITIFKSEALQRPVAS | ITIFKSEAL | VKLQTVHSIPLTINKEEALQRPVAS | LTINKEEAL | L1I | N4F | E6S | — | | 7-30 |
| SEQ ID NO: 111 | NSCVKLQTVHSIPITIYKAEALQRP | ITIYKAEAL | NSCVKLQTVHSIPLTINKEEALQRP | LTINKEEAL | L1I | N4Y | E6A | — | | 8-30 |
| SEQ ID NO: 112 | NSCVKLQTVHSIPITILKAEAFQRP | ITILKAEAF | NSCVKLQTVHSIPLTINKEEALQRP | LTINKEEAL | L1I | N4L | E6A | L9F | | 9-11 |

Compositions

In some embodiments, a peptide vaccine comprises one or more peptides of this disclosure and is administered in a pharmaceutical composition that includes a pharmaceutically acceptable carrier. In some embodiments, the peptide vaccine is comprised of the third peptide set, as described in this disclosure. In some embodiments, the pharmaceutical composition is in the form of a spray, aerosol, gel, solution, emulsion, lipid nanoparticle, nanoparticle, or suspension. In some embodiments, the pharmaceutical composition is in the form of a cationic nanoemulsion, one example of which is described by Brito et al. (2014) that is incorporated herein by reference.

The composition is preferably administered to a subject with a pharmaceutically acceptable carrier. Typically, in some embodiments, an appropriate amount of a pharmaceutically acceptable salt is used in the formulation, which in some embodiments can render the formulation isotonic.

In certain embodiments, the peptides are provided as an immunogenic composition comprising any one of the peptides described herein and a pharmaceutically acceptable carrier. In certain embodiments, the immunogenic composition further comprises an adjuvant. In certain embodiments, the peptides are conjugated with other molecules to increase their effectiveness as is known by those practiced in the art. For example, peptides can be coupled to antibodies that recognize cell surface proteins on antigen presenting cells to enhance vaccine effectiveness. One such method for increasing the effectiveness of peptide delivery is described in Woodham, et al. (2018). In certain embodiments for the treatment of autoimmune disorders, the peptides are delivered with a composition and protocol designed to induce tolerance as is known in the art. Example methods for using peptides for immune tolerization are described in Alhadj Ali, et al. (2017) and Gibson, et al. (2015).

In some embodiments, the pharmaceutically acceptable carrier is selected from the group consisting of saline, Ringer's solution, dextrose solution, and a combination thereof. Other suitable pharmaceutically acceptable carriers known in the art are contemplated. Suitable carriers and their formulations are described in Remington's Pharmaceutical Sciences, 2005, Mack Publishing Co. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of peptides being administered.

The phrase pharmaceutically acceptable carrier as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier is acceptable in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency. The composition may also include additional agents such as an isotonicity agent, a preservative, a surfactant, and, a divalent cation, preferably, zinc.

The composition can also include an excipient, or an agent for stabilization of a peptide composition, such as a buffer, a reducing agent, a bulk protein, amino acids (such as e.g., glycine or praline) or a carbohydrate. Bulk proteins useful in formulating peptide compositions include albumin. Typical carbohydrates useful in formulating peptides include but are not limited to sucrose, mannitol, lactose, trehalose, or glucose.

Surfactants may also be used to prevent soluble and insoluble aggregation and/or precipitation of peptides or proteins included in the composition. Suitable surfactants include but are not limited to sorbitan trioleate, soya lecithin, and oleic acid. In certain cases, solution aerosols are preferred using solvents such as ethanol. Thus, formulations including peptides can also include a surfactant that can reduce or prevent surface-induced aggregation of peptides by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. In some embodiments, surfactants used with the present disclosure are polyoxyethylene sorbitan mono-oleate, polysorbate 80, polysorbate 20. Additional agents known in the art can also be included in the composition.

In some embodiments, the pharmaceutical compositions and dosage forms further comprise one or more compounds that reduce the rate by which an active ingredient will decay, or the composition will change in character. So called stabilizers or preservatives may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

The present invention also teaches the stabilization (preventing or minimizing thermally or mechanically induced soluble or insoluble aggregation and/or precipitation of an inhibitor protein) of liquid solutions containing peptides at neutral pH or less than neutral pH by the use of amino acids including proline or glycine, with or without divalent cations resulting in clear or nearly clear solutions that are stable at room temperature or preferred for pharmaceutical administration.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

In some embodiments, the pharmaceutical compositions and dosage forms comprise anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for administration may be in the form of powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention (e.g., peptides) as an active ingredient.

A liquid composition herein can be used as such with a delivery device, or they can be used for the preparation of pharmaceutically acceptable formulations comprising peptides that are prepared for example by the method of spray drying. The methods of spray freeze-drying peptides/proteins for pharmaceutical administration disclosed in Maa et al., Curr. Pharm. Biotechnol., 2001, 1, 283-302, are incorporated herein. In another embodiment, the liquid solutions herein are freeze spray dried and the spray-dried product is collected as a dispersible peptide-containing powder that is therapeutically effective when administered to an individual.

The compounds and pharmaceutical compositions of the present invention can be employed in combination therapies, that is, the compounds and pharmaceutical compositions can be administered concurrently with, prior to, or subsequent to, one or more other desired therapeutics or medical procedures (e.g., peptide vaccine can be used in combination therapy with another treatment such as chemotherapy, radiation, pharmaceutical agents, and/or another treatment). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another therapeutic or prophylactic).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The current invention provides for dosage forms comprising peptides suitable for treating cancer or other diseases. The dosage forms can be formulated, e.g., as sprays, aerosols, nanoparticles, liposomes, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C., Ansel et al., Lippincott Williams & Wilkins; 7th edition (Oct. 1, 1999).

Generally, a dosage form used in the acute treatment of a disease may contain larger amounts of one or more of the active ingredients it comprises than a dosage form used in the chronic treatment of the same disease. In addition, the prophylactically and therapeutically effective dosage form may vary among different conditions. For example, a therapeutically effective dosage form may contain peptides that has an appropriate immunogenic action when intending to treat cancer or other disease. On the other hand, a different effective dosage may contain peptides that has an appropriate immunogenic action when intending to use the peptides of the invention as a prophylactic (e.g., vaccine) against cancer or another disease/condition. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery enhancing or penetration-enhancing agent. Different salts, hydrates, or solvates of the active ingredients can be used to adjust further the properties of the resulting composition.

Compositions can be formulated with appropriate carriers and adjuvants using techniques to yield compositions suitable for immunization. The compositions can include an adjuvant, such as, for example but not limited to, alum, poly IC, MF-59, squalene-based adjuvants, or liposomal based adjuvants suitable for immunization.

In some embodiments, the compositions and methods comprise any suitable agent or immune modulation which could modulate mechanisms of host immune tolerance and release of the induced antibodies. In certain embodiments, an immunomodulatory agent is administered in at time and in an amount sufficient for transient modulation of the subject's immune response so as to induce an immune response which comprises antibodies against for example tumor neoantigens (i.e., tumor-specific antigens (TSA)).

Expression Systems

In certain aspects, the invention provides culturing a cell line that expresses any one of the peptides of the invention in a culture medium comprising any of the peptides described herein.

Various expression systems for producing recombinant proteins/peptides are known in the art, and include, prokaryotic (e.g., bacteria), plant, insect, yeast, and mammalian expression systems. Suitable cell lines, can be transformed, transduced, or transfected with nucleic acids containing coding sequences for the peptides of the invention in order to produce the molecule of interest. Expression vectors containing such a nucleic acid sequence, which can be linked to at least one regulatory sequence in a manner that allows expression of the nucleotide sequence in a host cell, can be introduced via methods known in the art. Practitioners in the art understand that designing an expression vector can depend on factors, such as the choice of host cell to be transfected and/or the type and/or amount of desired protein to be expressed. Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication. For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells), resulting in the stable expression of transfected genes. A gene that encodes a selectable marker (for example, resistance to antibiotics or drugs) can be introduced into host cells along with the gene of interest in order to identify and select clones that stably express a gene encoding a protein of interest. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of peptide/protein products may be important for the function of the peptide/protein. Different host cell strains have characteristic and specific mechanisms for the post-translational processing and modification of proteins and gene products. As such, appropriate host systems or cell lines can be chosen to ensure the correct modification and processing of the target protein expressed. Thus, eukaryotic host cells possessing the cellular machinery for proper processing of the primary transcript, glycosylation, and phosphorylation of the gene product may be used.

Various culturing parameters can be used with respect to the host cell being cultured. Appropriate culture conditions for mammalian cells are well known in the art (Cleveland W L, et al., J Immunol Methods, 1983, 56(2): 221-234) or can be determined by the skilled artisan (see, for example, Animal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized.

Peptides of the invention can be purified from any human or non-human cell which expresses the polypeptide, including those which have been transfected with expression constructs that express peptides of the invention. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anionexchange resins, in which the more acidic fraction(s) is/are collected.

Methods of Treatment

In one embodiment, the subject matter disclosed herein relates to a preventive medical treatment started after following diagnosis of cancer in order to prevent the disease from worsening or curing the disease. In one embodiment, the subject matter disclosed herein relates to prophylaxis of subjects who are believed to be at risk for cancer or have previously been diagnosed with cancer (or another disease). In one embodiment, said subjects can be administered the peptide vaccine described herein or pharmaceutical compositions thereof. The invention contemplates using any of the peptides produced by the systems and methods described herein. In one embodiment, the peptide vaccines described herein can be administered subcutaneously via syringe or any other suitable method know in the art.

The compound(s) or combination of compounds disclosed herein, or pharmaceutical compositions may be administered to a cell, mammal, or human by any suitable means. Non-limiting examples of methods of administration include, among others, (a) administration though oral pathways, which includes administration in capsule, tablet, granule, spray, syrup, or other such forms; (b) administration through non-oral pathways such as intraocular, intranasal, intraauricular, rectal, vaginal, intraurethral, transmucosal, buccal, or transdermal, which includes administration as an aqueous suspension, an oily preparation or the like or as a drip, spray, suppository, salve, ointment or the like; (c) administration via injection, including subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; (e) administration topically; as deemed appropriate by those of skill in the art for bringing the compound or combination of compounds disclosed herein into contact with living tissue; (f) administration via inhalation, including through aerosolized, nebulized, and powdered formulations; and (g) administration through implantation.

As will be readily apparent to one skilled in the art, the effective in vivo dose to be administered and the particular mode of administration will vary depending upon the age, weight and species treated, and the specific use for which the compound or combination of compounds disclosed herein are employed. The determination of effective dose levels, that is the dose levels necessary to achieve the desired result, can be accomplished by one skilled in the art using routine pharmacological methods. Typically, human clinical applications of products are commenced at lower dose levels, with dose level being increased until the desired effect is achieved. Alternatively, acceptable in vitro studies can be used to establish useful doses and routes of administration of the compositions identified by the present methods using established pharmacological methods. Effective animal doses from in vivo studies can be converted to appropriate human doses using conversion methods known in the art (e.g., see Nair A B, Jacob S. A simple practice guide for dose conversion between animals and human. Journal of basic and clinical pharmacy. 2016 March; 7(2):27.)

Methods of Prevention

In some embodiments, the peptides prepared using methods of the invention can be used as a vaccine to promote an immune response against cancer (e.g., against tumor neoantigens). In some embodiments, the invention provides compositions and methods for induction of immune response, for example induction of antibodies to tumor neoantigens. In some embodiments, the antibodies are broadly neutralizing antibodies. In some embodiments, the peptides prepared using methods of the invention can be used as a vaccine to promote an immune response against a pathogen. In some embodiments, the peptides prepared using methods of the invention can be used to promote immune tolerance as an autoimmune disease therapeutic.

In some embodiments, the peptides prepared using methods of the invention can be combined with additional vaccine components. In some embodiments, these combined vaccines can be encoded in one or more nucleic acids that encode the peptides produced with the methods described herein and additional vaccine components (e.g. peptides or proteins) that are known in the art. In some embodiments, these combined vaccines are created by adding the peptides or proteins that encode the additional vaccine components of the peptides that result from the methods described here for combined formulation and packaging. An example of the combination of vaccine components is the creation of BCL-ABL vaccines that use one or more nucleic acids to encode the components of vaccines for BCL-ABL b2a2 and b3a2 and packaging the nucleic acids in a mRNA-LNP or DNA formulation, or separately formulating different components as mRNA-LNP or DNA and then combining them for packaging or immediately before administration to a person.

The compositions, systems, and methods disclosed herein are not to be limited in scope to the specific embodiments described herein. Indeed, various modifications of the compositions, systems, and methods in addition to those described will become apparent to those of skill in the art from the foregoing description.

SEQUENCE LISTING

The patent contains a lengthy sequence listing. A copy of the sequence listing is available in electronic form from the USPTO web site (https://seqdata.uspto.gov/?pageRequest=docDetail&DocID=US12290554B2). An electronic copy of the sequence listing will also be available from the USPTO upon request and payment of the fee set forth in 37 CFR 1.19(b)(3).

What is claimed is:

1. A composition comprising one or more polynucleotides encoding at least two amino acid sequences, wherein the at least two amino acid sequences are selected from the group consisting of SEQ ID NOs: 1 to 8, SEQ ID NOs: 10 to 17, and SEQ ID NOs: 19 to 44.

2. The composition of claim 1, wherein the one or more polynucleotides are contained in a construct for in vivo expression of the one or more polynucleotides.

3. The composition of claim 2, wherein an administration of the one or more polynucleotides causes one or more peptides encoded by the or more polynucleotides to be displayed by an HLA class I molecule present in a subject.

4. The composition of claim 3, wherein the one or more polynucleotides are contained in a construct for in vivo expression of at least two peptides encoded by the one or more polynucleotides, wherein an administration of the one or more polynucleotides to the subject causes:

a first peptide of the at least two peptides to be displayed by a first plurality of HLA class I alleles present in the subject; and a second peptide of the at least two peptides to be displayed by a second plurality of HLA class I alleles present in the subject, wherein the first plurality of HLA class I alleles and the second plurality of HLA class I alleles differ by at least one HLA class I allele.

5. The composition of claim 3, wherein the one or more peptides is a modified or an unmodified fragment of a BCL-ABL gene fusion.

6. The composition of claim 5, wherein the BCR-ABL gene fusion is b3a2 or b2a2.

7. The composition of claim 5, wherein the two or more amino acid sequences are selected based on a prevalence of the BCR-ABL gene fusion in a risk group that the subject belongs to, and wherein the composition is configured for administration in an effective amount to the subject to promote an immune response against cancer, and wherein the cancer is associated with the BCR-ABL gene fusion.

8. The composition of claim 3, wherein the one or more polynucleotides are configured for administration in an effective amount to the subject to treat cancer.

9. A composition comprising one or more polynucleotides encoding one or more amino acid sequences selected from the group consisting of SEQ ID NOs: 46 to 112.

10. The composition of claim 9, wherein the one or more polynucleotides are contained in a construct for in vivo expression of the one or more polynucleotides.

11. The composition of claim 10, wherein an administration of the one or more polynucleotides causes one or more peptides encoded by the one or more polynucleotides to be displayed by an HLA class II molecule present in a subject.

12. The composition of claim 11, wherein the one or more amino acid sequences are derived from a modified or an unmodified fragment of a BCL-ABL gene fusion.

13. The composition of claim 12, wherein the BCR-ABL gene fusion is b3a2 or b2a2.

14. The composition of claim 12, wherein the one or more amino acid sequences are selected based on a prevalence of the BCR-ABL gene fusion in a risk group that the subject belongs to, and wherein the composition is configured for administration in an effective amount to the subject to promote an immune response against cancer, and wherein the cancer is associated with the BCR-ABL gene fusion.

15. The composition of claim 11, wherein the composition is configured for administration in an effective amount to the subject to treat cancer, wherein the cancer is associated with the BCR-ABL gene fusion.

16. The composition of claim 9, wherein the one or more polynucleotides encode at least two amino acid sequences selected from the group consisting of SEQ ID NOs: 46 to 112.

* * * * *